(12) United States Patent
Pulici et al.

(10) Patent No.: US 8,524,707 B2
(45) Date of Patent: Sep. 3, 2013

(54) BICYCLIC PYRAZOLES AS PROTEIN KINASE INHIBITORS

(75) Inventors: Maurizio Pulici, Caponago (IT); Chiara Marchionni, Milan (IT); Claudia Piutti, Nerviano (IT); Fabio Gasparri, Parabiago (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 168 days.

(21) Appl. No.: 13/140,915

(22) PCT Filed: Dec. 17, 2009

(86) PCT No.: PCT/EP2009/067438
§ 371 (c)(1),
(2), (4) Date: Jun. 20, 2011

(87) PCT Pub. No.: WO2010/070060
PCT Pub. Date: Jun. 24, 2010

(65) Prior Publication Data
US 2011/0257165 A1    Oct. 20, 2011

(30) Foreign Application Priority Data
Dec. 19, 2008   (EP) .................................... 08172429

(51) Int. Cl.
C07D 513/04    (2006.01)
A61K 31/429    (2006.01)

(52) U.S. Cl.
USPC ........ 514/224.2; 514/339; 544/48; 546/275.7

(58) Field of Classification Search
USPC ..................... 544/48; 546/275.7; 514/224.2, 514/339
See application file for complete search history.

(56) References Cited

FOREIGN PATENT DOCUMENTS
WO       WO 0212250 A2 *   2/2002
WO       WO 2007105058 A2 *   9/2007
WO       WO 2008015340 A2 *   2/2008

* cited by examiner

*Primary Examiner* — Kahsay Habte
(74) *Attorney, Agent, or Firm* — Scully, Scott, Murphy & Presser, P.C.

(57) ABSTRACT

3,4-diaryl-bicyclicpyrazole derivatives of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

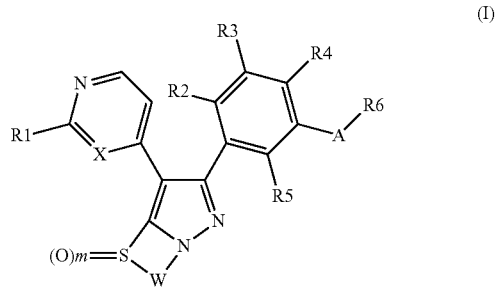

15 Claims, No Drawings

BICYCLIC PYRAZOLES AS PROTEIN KINASE INHIBITORS

The present invention relates to certain substituted 3,4-diaryl-bicyclicpyrazole compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The classical Ras, Raf, MEK (mitogen activated protein kinase/extracellular signal -regulated kinase kinase), ERK (extracellular signal-regulated kinase) pathway plays a central role in the regulation of a variety of cellular functions dependent upon cellular context, including cellular proliferation, differentiation, survival, immortalization and angiogenesis (reviewed in Peyssonnaux and Eychene, Biology of the Cell, 2001, 93,3-62). In this pathway, Raf family members are recruited to the plasma membrane upon binding to guanosine triphosphate (GTP) loaded Ras resulting in the phosphorylation and activation of Raf proteins. Activated Rafs then phosphorylate and activate MEKs, which in turn phosphorylate and activate ERKs. Upon activation, ERKs translocate from the cytoplasm to the nucleus resulting in the phosphorylation and regulation of activity of transcription factors such as Elk-I and Myc. The Ras/Raf/MEK/ERK pathway has been reported to contribute to the tumorigenic phenotype by inducing immortalisation, growth factor-independent growth, insensitivity to growth-inhibitory signals, ability to invade and metastasize, by stimulating angiogenesis and by inhibiting apoptosis (reviewed in Kolch et al., Exp. Rev. Mol. Med., 2002, 4, 1-18). In fact, ERK phosphorylation is enhanced in approximately 30% of all human tumours (Hoshino et al., Oncogene, 1999, 18, 813-822). This may be a result of overexpression and/or mutation of key members of the pathway.

Three Raf serine/threonine protein kinase isoforms have been reported Raf-1 /c-Raf, B-Raf and A-Raf (reviewed in Mercer and Pritchard, Biochim. Biophys. Acta, 2003, 1653, 25-40), the genes for which are thought to have arisen from gene duplication. All three Raf genes are expressed in most tissues but with differences: c-Raf is expressed ubiquitously at high levels, whereas B-Raf high-level expression is found in neuronal tissue and A-Raf in urogenital tissue. The highly homologous Raf family members have overlapping but distinct biochemical activities and biological functions (Hagemann and Rapp, Expt. Cell Res. 1999, 253, 34-46). Expression of all three Raf genes is required for normal murine development however both c-Raf and B-Raf are required to complete gestation. B-Raf –/– mice die at E12.5 due to vascular haemorrhaging caused by increased apoptosis of endothelial cells (Wojnowski et al, Nature Genet., 1997, 16, 293-297). B-Raf is reportedly the major isoform involved in cell proliferation and the primary target of oncogenic Ras. Activating 5 somatic missense mutations have been identified exclusively for B-Raf, occurring with a frequency of 66% in malignant cutaneous melanomas (Davies et al., Nature, 2002, 417, 949-954) and also present in a wide range of human cancers, including but not limited to papillary thyroid tumours (Cohen et al., J. Natl. Cancer Inst., 2003, 95, 625-627), cholangiocarcinomas (Tannapfel et al., Gut, 2003, 52, 706-712), colon and ovarian cancers (Davies et al., Nature, 10 2002, 417, 949-954). The most frequent mutation in B-Raf (80%) is a glutamic acid for valine substitution at position 600. These mutations increase the basal kinase activity of B-Raf and are thought to uncouple Raf/MEK/ERK signalling from upstream proliferation drives including Ras and growth factor receptor activation resulting in constitutive activation of ERK. Mutated B-Raf proteins are transforming in NIH3T3 cells (Davies et al., Nature, 2002, 15 417, 949-954) and melanocytes (Wellbrock et al., Cancer Res., 2004, 64, 2338-2342) and have also been shown to be essential for melanoma cell viability and transformation (Hingorani et al., Cancer Res., 2003, 63, 5198-5202). As a key driver of the Raf/MEK/ERK signalling cascade, B-Raf represents a likely point of intervention in tumours dependent on this pathway.

Substituted pyrazolo-thiazoles and pyrazolo-thiazines and their preparation have been disclosed in DD103006 and DD157803 (Peseke, Klaus), no specific use for such derivatives is therein indicated.

Substituted 3-aryl-pyrazolo-thiazoles and their activity as herbicides have been disclosed in WO9315074 (du Pont de Nemours, E. I., and Co., USA).

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a compound represented by formula (I),

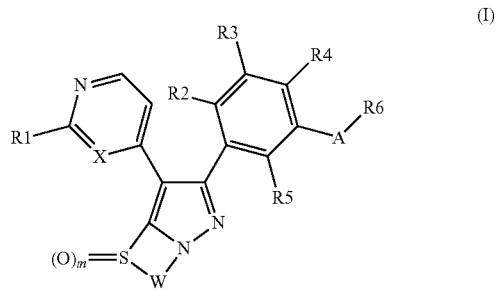

wherein:

X is CH or N;

R1 is hydrogen, halogen, NR7R8, NHCOR9, SR10 or SO$_2$R10, wherein:
   R7 and R8 are, each independently one from the other, hydrogen, or a group optionally substituted selected from straight or branched (C$_1$-C$_8$) alkyl, (C$_3$-C$_8$) cycloalkyl, heterocyclyl, aryl and heteroaryl, or R7 and R8 taken together may form a phthalyl group,
   R9 is OR10, NR11R12 or a group optionally substituted selected from straight or branched (C$_1$-C$_6$) alkyl, (C$_2$-C$_8$) alkenyl or (C$_2$-C$_8$) alkynyl, (C$_3$-C$_8$) cycloalkyl, heterocyclyl, aryl and heteroaryl,
   R10 is a group optionally substituted selected from straight or branched (C$_1$-C$_8$) alkyl, (C$_3$-C$_8$) cycloalkyl, heterocyclyl, aryl and heteroaryl,
   R11 and R12 are, each independently one from the other, hydrogen or a group optionally substituted selected from straight or branched (C$_1$-C$_8$) alkyl, (C$_3$-C$_8$) cycloalkyl, heterocyclyl, aryl and heteroaryl, or taken together with the nitrogen atom to which they are bonded R11 and R12 may form an optionally substituted 3 to 8 membered heterocyclyl or heteroaryl, optionally containing one additional heteroatom or heteroatomic group selected from S, O, N or NH;

R2, R3, R4 and R5 are, each independently one from the other, hydrogen, halogen, trifluoromethyl, trichloromethyl, cyano, OR13 or a group optionally substituted selected from straight or branched ($C_1$-$C_8$) alkyl, and ($C_3$-$C_8$) cycloalkyl, wherein:
R13 is hydrogen or a group optionally substituted selected from straight or branched ($C_1$-$C_8$) alkyl and ($C_3$-$C_8$) cycloalkyl;
A is —O—, —CON(Y)—, —CON(Y)O—, —CON(Y)N(Y)—, —CON(Y)SO$_2$—, —SO$_2$N(Y)—, —SO$_2$N(Y)O—, —SO$_2$N(Y)N(Y)—, —SO$_2$N(Y)CO—, —SO$_2$N(Y)CON(Y)—, —SO$_2$N(Y)SO$_2$—, —N(Y)CO—, —N(Y)SO$_2$—, —N(Y)CON(Y)—, —N(Y)CSN(Y)—, —N(Y)CON(Y)N(Y)—, —N(Y)COO—, —N(Y)CON(Y)SO$_2$—, —N(Y)SO$_2$N(Y)—, —C(R'R")CON(Y)—, —C(R'R")CSN(Y)—, —C(R'R")CON(Y)O—, —C(R'R")CON(Y)N(Y)—, —C(R'R")CON(Y)SO$_2$—, —C(R'R")SO$_2$N(Y)—, —C(R'R")SO$_2$N(Y)O—, —C(R'R")SO$_2$N(Y)N(Y)—, —C(R'R")SO$_2$N(Y)CO—, —C(R'R")SO$_2$N(Y)SO$_2$—, —C(R'R")N(Y)CO, —C(R'R")N(Y)SO$_2$—, —C(R'R")N(Y)CON(Y)—, —C(R'R")N(Y)CSN(Y)—, —C(R'R")N(Y)COO— or —C(R'R")N(Y)SO$_2$N(Y)—, wherein:
Y is hydrogen or an optionally substituted straight or branched ($C_1$-$C_3$) alkyl;
and R' and R" are, each independently one from the other, hydrogen or an optionally substituted straight or branched ($C_1$-$C_6$) alkyl, or taken together with the carbon atom to which they are bonded R' and R" may form an optionally substituted ($C_3$-$C_8$) cycloalkyl;
R6 is hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
m is an integer from 0 to 2;
W is (CH$_2$)n, wherein n is an integer from 2 to 4, CH(R14)-CH(R15) or C(R14)=C(R15), wherein
R14 and R15 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl, or R14 is hydrogen and R15 is COR16, or R15 is hydrogen and R14 is COR16, wherein:
R16 is OR17, NR18R19 or a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, heterocyclyl, aryl and heteroaryl, wherein:
R17 is hydrogen or a group optionally substituted selected from straight or branched ($C_1$-$C_8$) alkyl, ($C_3$-$C_8$) cycloalkyl, heterocyclyl, aryl and heteroaryl;
R18 and R19 are, each independently one from the other, hydrogen, a group optionally substituted selected from straight or branched ($C_1$-$C_8$) alkyl, ($C_3$-$C_8$) cycloalkyl, heterocyclyl, aryl and heteroaryl, or taken together with the nitrogen atom to which they are bonded R18 and R19 may form an optionally substituted 3 to 8 membered heterocyclyl or heteroaryl, optionally containing one additional heteroatom or heteroatomic group selected from S, O, N or NH;
and pharmaceutically acceptable salts thereof.

The present invention also provides methods of preparing the substituted 3,4-diaryl-bicyclicpyrazole compounds, represented by formula (I), prepared through a process consisting of standard synthetic transformations.

The present invention also provides a method for treating diseases caused by and/or associated with dysregulated protein kinase activity, particularly RAF family, protein kinase C in different isoforms, Met, PAK-4, PAK-5, ZC-1, STLK-2, DDR-2, Aurora A, Aurora B, Aurora C, Bub-1, Chk1, Chk2, HER2, MEK1, MAPK, EGF-R, PDGF-R, FGF-R, IGF-R, PI3K, wee1 kinase, Src, Abl, Akt, MAPK, ILK, MK-2, IKK-2, Cdc7, Nek, Cdk/cyclin kinase family, including PLK-1 and PLK-3, which comprises administering to a mammal, in need thereof, an effective amount of a substituted 3,4-diarylpyrazole compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent.

Moreover the invention provides an in vitro method for inhibiting the RAF family protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like. Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxigen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

With the term "straight or branched $C_1$-$C_8$ alkyl", we intend any of the groups such as, for instance, methyl, ethyl, n-propyl, isopropyl, n-butyl, isobutyl, tert-butyl, sec-butyl, n-pentyl, n-hexyl, n-heptyl, n-octyl and the like.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_1$-$C_3$ alkyl", we intend any of the groups such as, for instance, methyl, ethyl, n-propyl, isopropyl.

With the term "$C_3$-$C_8$ cycloalkyl" we intend, unless otherwise provided, 3- to 8-membered all-carbon monocyclic ring, which may contain one or more double bonds but does not have a completely conjugated 7-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_2$-$C_8$ alkenyl" we intend an aliphatic $C_2$-$C_8$ hydrocarbon chain containing at least one carbon-carbon double dond and which can be straight or branched. Representative examples include, but are not limited to, ethenyl, 1-propenyl, 2-propenyl, 1- or 2-butenyl, and the like.

With the term "$C_2$-$C_8$ alkynyl" we intend an aliphatic $C_2$-$C_8$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated 7-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

The term "phthalyl" means

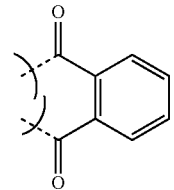

According to the present invention and unless otherwise provided, the phrase "optionally substituted" applied to any of the groups defined above, means that such groups may be optionally substituted, in any of their free positions, by one or more groups, for instance 1 to 6 groups, independently selected from: halogen, nitro, oxo groups (=O), cyano, $C_1$-$C_8$ alkyl, polyfluorinated alkyl, polyfluorinated alkoxy, $C_2$-$C_8$ alkenyl, $C_2$-$C_8$ alkynyl, hydroxyalkyl, aryl, arylalkyl, heteroaryl, heteroarylalkyl, heterocyclyl, heterocyclylalkyl, $C_3$-$C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term halogen atom we intend a fluorine, chlorine, bromine or iodine atom.

With the term polyfluorinated alkyl or polyfluorinated alkoxy we intend any of the above straight or branched $C_1$-$C_8$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_8$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_8$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:
A is —O—, —CON(Y)—, —CON(Y)O—, —CON(Y)N(Y)—, —CON(Y)SO$_2$—, —SO$_2$N(Y)—, —N(Y)CO—, —N(Y)SO$_2$—, —N(Y)CON(Y)—, —N(Y)CSN(Y)—, —N(Y)COO—, —C(R'R")CON(Y)—, —C(R'R")N(Y)CO or —C(R'R")N(Y)CON(Y)—,
wherein:
Y, R' and R" are as defined above.

Another preferred class of compounds of formula (I) are the compounds wherein:
A is —O—, —CON(Y)—, —CON(Y)SO$_2$—, —SO$_2$N(Y)—, —N(Y)CO—, —N(Y)SO$_2$—, —N(Y)CON(Y)—, —N(Y)CSN(Y)—,
wherein:
Y, R' and R" are as defined above.

A further preferred class of compounds of formula (I) are the compounds wherein:
R1 is hydrogen or NR7R8, wherein:
R7 and R8 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl.

Another further preferred class of compounds of formula (I) are the compounds wherein:
R2, R3, R4 and R5 are, each independently one from the other, hydrogen, halogen, trifluoromethyl, trichloromethyl or cyano.

Another further preferred class of compounds of formula (I) are the compounds wherein:
R6 is an optionally substituted group selected from straight or branched ($C_1$-$C_8$) alkyl, ($C_3$-$C_8$) cylcoalkyl, heterocyclyl, aryl and heteroaryl.

Preferred compounds of formula (I) are the compounds listed below:
1) 1-(4-chloro-phenyl)-3-[3-(3-pyridin-4-yl-6,7-dihydro-5H-pyrazolo[5,1-b][1,3]thiazin-2-yl)-phenyl]-urea,
2) 1-[3-(3-pyridin-4-yl-6,7-dihydro-5H-pyrazolo[5,1-b][1,3]thiazin-2-yl)-phenyl]-3-p-tolyl-urea,
3) 1-[3-(3-pyridin-4-yl-6,7-dihydro-5H-pyrazolo[5,1-b][1,3]thiazin-2-yl)-phenyl]-3-(4-trifluoromethyl-phenyl)-urea,
4) 3-fluoro-N-[3-(3-pyridin-4-yl-6,7-dihydro-5H-pyrazolo[5,1-b][1,3]thiazin-2-yl)-phenyl]-enzenesulfonamide,
5) 1-[3-(7-pyridin-4-yl-2,3-dihydro-pyrazolo[5,1-b]thiazol-6-yl)-phenyl]-3-(4-trifluoromethyl-phenyl)-urea,
6) 1-(4-chloro-phenyl)-3-[3-(7-pyridin-4-yl-2,3-dihydro-pyrazolo[5,1-b]thiazol-6-yl)-phenyl]-urea,
7) 3-(7-pyridin-4-yl-2,3-dihydro-pyrazolo[5,1-b]thiazol-6-yl)-phenol,
8) 3-(3-pyridin-4-yl-6,7-dihydro-5H-pyrazolo[5,1-b][1,3]thiazin-2-yl)-phenol,
9) 2,5-difluoro-N-[3-(3-pyridin-4-yl-6,7-dihydro-5H-pyrazolo[5,1-b][1,3]thiazin-2-yl)-phenyl]-benzenesulfonamide,
10) 3-(1,1-dioxo-7-pyridin-4-yl-2,3-dihydro-pyrazolo[5,1-b]thiazol-6-yl)-phenol,
11) 2,5-difluoro-N-[3-(7-pyridin-4-yl-2,3-dihydro-pyrazolo[5,1-b]thiazol-6-yl)-phenyl]-benzenesulfonamide,
12) N-[3-(3-pyridin-4-yl-6,7-dihydro-5H-pyrazolo[5,1-b][1,3]thiazin-2-yl)-phenyl]-2-(4-trifluoromethyl-phenyl)-acetamide,
13) furan-2-sulfonic acid [3-(3-pyridin-4-yl-6,7-dihydro-5H-pyrazolo[5,1-b][1,3]thiazin-2-yl)-phenyl]-amide,
14) thiophene-3-sulfonic acid [3-(3-pyridin-4-yl-6,7-dihydro-5H-pyrazolo[5,1-b][1,3]thiazin-2-yl)-phenyl]-amide, 15) N-(4-tert-butyl-phenyl)-3-(7-pyridin-4-yl-2,3-dihydro-pyrazolo[5,1-b]thiazol-6-yl)-benzamide,
16) 7-pyridin-4-yl-6-{3-[3-(4-trifluoromethyl-phenyl)-ureido]-phenyl}-pyrazolo[5,1-b]thiazole-3-carboxylic acid amide,
17) 6-[3-(2,5-difluoro-benzenesulfonylamino)-phenyl]-7-pyridin-4-yl-pyrazolo[5,1-b]thiazole-3-carboxylic acid amide,
18) 1-(4-tert-butyl-phenyl)-3-[3-(7-pyridin-4-yl-2,3-dihydro-pyrazolo[5,1-b]thiazol-6-yl)-phenyl]-urea,
19) 1-[3-(1-oxo-7-pyridin-4-yl-2,3-dihydro-pyrazolo[5,1-b]thiazol-6-yl)-phenyl]-3-(4-trifluoromethyl-phenyl)-urea,
20) 3-(7-pyridin-4-yl-pyrazolo[5,1-b]thiazol-6-yl)-phenol,
21) 2,5-difluoro-N-[3-(7-pyridin-4-yl-pyrazolo[5,1-b]thiazol-6-yl)-phenyl]-benzenesulfonamide,
22) 1-[3-(7-pyridin-4-yl-pyrazolo[5,1-b]thiazol-6-yl)-phenyl]-3-(4-trifluoromethyl-phenyl)-urea,
23) N-[2,4-difluoro-3-(7-pyridin-4-yl-2,3-dihydro-pyrazolo[5,1-b]thiazol-6-yl)-phenyl]-2,5-difluoro-benzenesulfonamide,
24) 3-(7-pyridin-4-yl-2,3-dihydro-pyrazolo[5,1-b]thiazol-6-yl)-N-(4-trifluoro-methyl-phenyl)-benzamide,
25) 2,6-dibromo-3-(7-pyridin-4-yl-pyrazolo[5,1-b]thiazol-6-yl)-phenol,
26) N-{4-[6-(3-Hydroxy-phenyl)-pyrazolo[5,1-b]thiazol-7-yl]-pyridin-2-yl}-acetamide,
27) 3-[7-(2-amino-pyrimidin-4-yl)-pyrazolo[5,1-b]thiazol-6-yl]-phenol,
28) N-[2,4-difluoro-3-(7-pyridin-4-yl-pyrazolo[5,1-b]thiazol-6-yl)-phenyl]-2,5-difluoro-benzenesulfonamide,
29) N-(4-{6-[3-(2,5-difluoro-benzenesulfonylamino)-phenyl]-2,3-dihydro-pyrazolo[5,1-b]thiazol-7-yl}-pyridin-2-yl)-acetamide,
30) N-[4-(6-{3-[3-(4-trifluoromethyl-phenyl)-ureido]-phenyl}-2,3-dihydro-pyrazolo[5,1-b]thiazol-7-yl)-pyridin-2-yl]-acetamide,
31) 1-[3-(7-pyrimidin-4-yl-2,3-dihydro-pyrazolo[5,1-b]thiazol-6-yl)-phenyl]-3-(4-trifluoromethyl-phenyl)-urea,
32) 1-{3-[7-(2-amino-pyrimidin-4-yl)-2,3-dihydro-pyrazolo[5,1-b]thiazol-6-yl]-phenyl}-3-(4-trifluoromethyl-phenyl)-urea,
33) N-(4-{6-[3-(2,5-difluoro-benzenesulfonylamino)-phenyl]-pyrazolo[5,1N-thiazol-7-yl}-pyridin-2-yl)-acetamide,
34) N-[4-(6-{3-[3-(4-trifluoromethyl-phenyl)-ureido]-phenyl}-pyrazolo[5,1-b]-thiazol-7-yl)-pyridin-2-yl]-acetamide,
35) 1-[3-(7-pyrimidin-4-yl-pyrazolo[5,1-b]thiazol-6-yl)-phenyl]-3-(4-trifluoro-methyl-phenyl)-urea,
36) 1-{3-[7-(2-amino-pyrimidin-4-yl)-pyrazolo[5,1-b]thiazol-6-yl]-phenyl}-3-(4-trifluoromethyl-phenyl)-urea,
37) N-(4-{6-[3-(2,5-difluoro-benzenesulfonylamino)-2,6-difluoro-phenyl]-2,3-dihydro-pyrazolo[5,1-b]thiazol-7-yl}-pyridin-2-yl)-acetamide,
38) N-(4-{6-[3-(2,5-difluoro-benzenesulfonylamino)-2,6-difluoro-phenyl]-pyrazolo[5,1-b]thiazol-7-yl}-pyridin-2-yl)-acetamide,
39) N-[2,4-difluoro-3-(7-pyrimidin-4-yl-pyrazolo[5,1-b]thiazol-6-yl)-phenyl]-2,5-difluoro-benzenesulfonamide,
40) N-{3-[7-(2-amino-pyrimidin-4-yl)-pyrazolo[5,1-b]thiazol-6-yl]-2,4-difluoro-phenyl}-2,5-difluoro-benzenesulfonamide,
41) 3-(7-pyridin-4-yl-pyrazolo[5,1-b]thiazol-6-yl)-N-(4-trifluoromethyl-phenyl)-benzamide,
42) 3-(7-pyrimidin-4-yl-pyrazolo[5,1-b]thiazol-6-yl)-N-(4-trifluoromethyl-phenyl)-benzamide,
43) 3-[7-(2-amino-pyrimidin-4-yl)-pyrazolo[5,1-b]thiazol-6-yl]-N-(4-trifluoro-methyl-phenyl)-benzamide and
44) 3-(7-pyrimidin-4-yl-pyrazolo[5,1-b]thiazol-6-yl)-phenol.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis may be performed by simple modifications apparent to those skilled in the art, for instance by appropriately protecting interfering groups, by using suitable reagents known in the art, or by making routine modifications of reaction conditions. Alternatively other reactions referred to herein or known in the art will be recognized as having adaptability for preparing the compounds of the invention.

The reported Scheme 1 shows the preparation of a compound of formula (I).

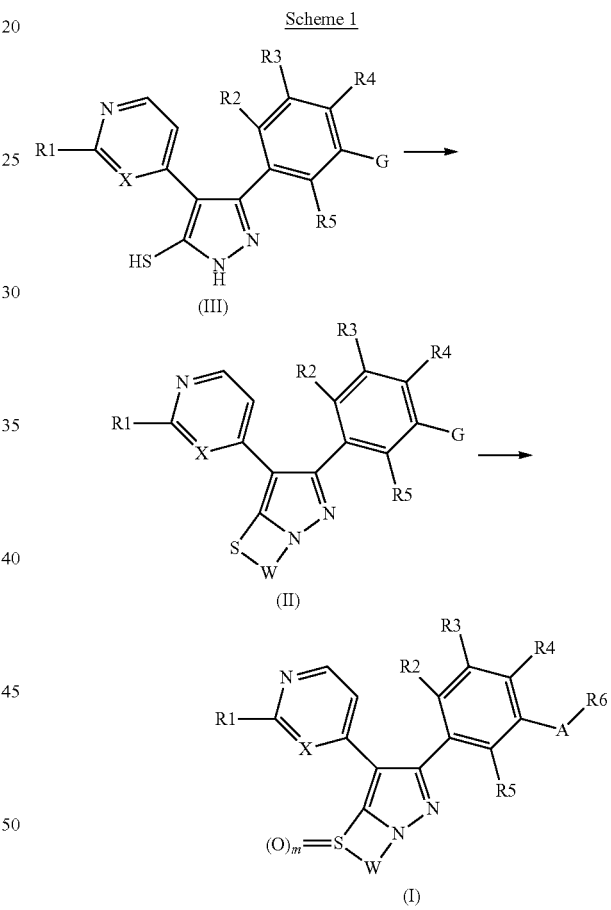

wherein
G is an optionally protected amino or hydroxyl group, a nitro group, a halogen, preferably bromine, a cyano group or a suitable carboxylic ester, and
X, R1, R2, R3, R4, R5 and W are as defined above.
The intermediate compound of formula (III) is prepared according to method A described below.
The intermediate compound of formula (II) is prepared according to method B described below.
A compound of formula (II) can be optionally converted into another compound of formula (II) according to any of the methods C and D described below.
A compound of formula (I) is prepared according to any of the method E, F, G and H described below.

A compound of formula (I) can be optionally converted into another compound of formula (I) according to any of the methods J, K, L and I described below.

According to step "a" of method A, the condensation between an aromatic aldehyde of formula 1 with a dialkyl phosphite can be accomplished in a variety of ways according

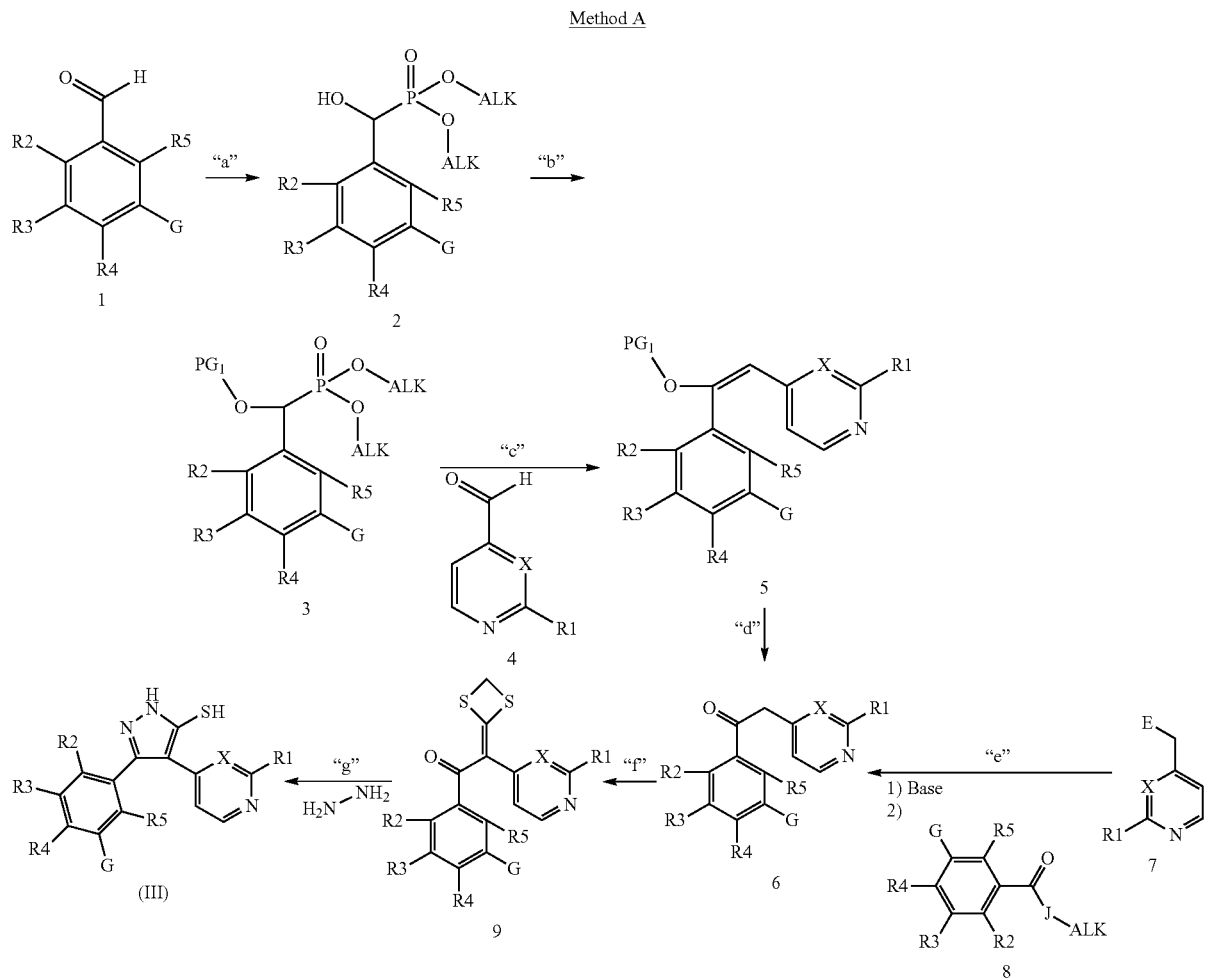

Method A

In the above scheme, X, R1, R2, R3, R4, R5 and G are as defined above, J is oxigen or a group —N(CH3)O—, $PG_1$ is a protecting group such as silyl or acyl derivatives or tetrahydropyranyl, Alk is $C_1$-$C_6$ alkyl and E is hydrogen or alkoxycarbonyl.

In a synthetic process for the preparation of a compound of formula (III), which is described in method A, in step "a" a compound of formula 1 is reacted with a dialkylphosphite to yield a hydroxyalkyl phosphonate of formula 2. In steps "b" and "c" protection of the alcoholic function followed by Wittig-type reaction with a suitable 4-pyridyl or 4-pyrimidinyl carboxaldehyde of formula 4 yields a compound of formula 5 that in step "d" is conveniently hydrolyzed to yield a ketone represented by formula 6. In step "e" the latter may be obtained also starting from a compound of formula 7 which is transformed in the corresponding metal anion and reacted with an aromatic alkyl carboxylate or Weinreb amide of formula 8. In step "f" transformation of a compound of formula 6 to a dithioketal of formula 9 is accomplished by the reaction with carbon disulfide in the presence of a dihalomethane derivative. The latter is eventually condensed with hydrazine to give a pyrazole derivative of formula (III).

to conventional methods. Preferably it is carried out in presence of a base, such as triethylamine (TEA) 1,8-diazabicyclo [5.4.0]undec-7ene (DBU), lithium diisopropylamide (LDA), sodium methoxide or the like, preferably in a solvent such as, for instance, ethylacetate, dichloromethane, toluene, tetrahydrofuran, 1,4-dioxane, 1,2-dimethoxyethane, acetonitrile at a temperature ranging from 0° C. to reflux and for a time ranging from 30 minutes to about 24 hours.

According to step "b" of method A, the protection of the alcoholic function can be accomplished in a variety of ways according to conventional methods that can be readily appreciated by all those skilled in the art. For instance, such alcoholic group can be protected as silyl derivatives by treatment with a suitable silylating agent, such as any alkylsilyl halide or azide in the presence of a base, such as, for instance, 1,8-diazabicyclo[5.4.0]undec-7ene (DBU), or by treatment with 1,1,1,3,3,3-hexamethyldisilazane in the presence of submolar amounts of iodine or of a suitable acid, such as, for instance, sulphuric acid. Such reactions can be performed using a variety of solvents such as dichloromethane, toluene, tetrahydrofuran, 1,4-dioxane, 1,2-dimethoxyethane, acetonitrile at a temperature ranging from 0° C. to reflux and for a time ranging from 30 minutes to about 24 hours. Again, said protection can be accomplished by acylation following treatment with a suitable acylating agent such as chloride acid or anhydride in the presence of a base using a variety of solvents such as dichloromethane, toluene, tetrahydrofuran, 1,4-dioxane, 1,2-dimethoxyethane, N,N-dimethylformamide, N,N-dimethylacetamide, acetonitrile or the like at a temperature ranging from 0° C. to reflux and for a time ranging from 30 minutes to about 24 hours. More preferably such a protection can be accomplished using 3,4-dihydro-2H-pyran in the presence of a suitable acidic catalyst, such as, for instance, p-toluensulfonic acid (PTSA) using solvents such as toluene, tetrahydrofuran, 1,4-dioxane, 1,2-dimethoxyethane at a temperature ranging from 0° C. to reflux and for a time ranging from 30 minutes to about 24 hours.

According to step "c" of method A, the reaction of a compound of formula 3 with a compound of formula 4 can be accomplished in the presence of a suitable base such as, for instance sodium methoxide, sodium ethoxide, sodium hydride, lithium diisopropylamide or triethylamine in a variety of solvents such as tetrahydrofuran, 1,4-dioxane, 1,2-dimethoxyethane, toluene, dichloromethane, or the like at a temperature ranging from 0° C. to reflux and for a time ranging from 30 minutes to about 24 hours.

According to step "d" of method A, the conversion of a compound of formula 5 to a compound of formula 6 can be accomplished in a variety of ways known in the art depending on the nature of the protecting group itself. For example, when the protective group installed in step "b" of method A is tetrahydropyranyl, the conversion is made using any of the hydrolytic method known in the literature, for instance using an aqueous solution of hydrochloric acid in a suitable co-solvent, for instance methanol, ethanol, tetrahydrofuran, acetonitrile or the like at a temperature ranging from 0° C. to reflux and for a time ranging from 30 minutes to about 24 hours. When, for example, such a protecting group is a silyl group, deprotection can be accomplished using strong acids like trifluoroacetic acid, perchloric acid, hydrochloric acid, hydrofluoric acid, as well as tetrabutyl ammonium fluoride and derivatives thereof, in a suitable solvent such as tetrahydrofuran, 1,4-dioxane, 1,2-dimethoxyethane, methanol, ethanol, acetonitrile, dichloromethane, or the like at a temperature ranging from 0° C. to reflux and for a time ranging from 30 minutes to about 24 hours.

When, for example, such a protecting group is an acyl group, deprotection can be accomplished using aqueous alkali, such as NaOH, KOH, LiOH or the like, optionally in the presence of a suitable solvent such as ethanol, methanol, tetrahydrofuran or the like.

According to step "e" of method A, a compound of formula 7 is converted to a compound of formula 6 by reaction with a strong base such as sodium hexamethyldisilazane (NaHMDS), litium hexamethyldisilazane (LiHMDS), lithium diisopropylamide (LDA), a Grignard reagent and the like, following condensation with an aromatic alkyl carboxylate or Weinreb amide of formula 8. Said reaction is typically performed using a variety of solvents such as toluene, N,N-dimethylformamide, tetrahydrofuran, 1,4-dioxane, 1,2-dimethoxyethane, or the like at a temperature ranging from 0° C. to reflux and for a time ranging from 30 minutes to about 24 hours.

According to step "f" of method A, synthesis of the dithioketal derivative of formula 9 is accomplished using carbon disulfide and a dihalomethane derivative, such as, for instance dibromomethane, in the presence of a suitable base such as, for instance, NaH, K₂CO₃, Cs₂CO₃, NaOH, DBU, LiHMDS and the like, in a suitable solvent such as dichloromethane, tetrahydrofuran, 1,4-dioxane, 1,2-dimethoxyethane, acetonitrile, N,N-dimethylformamide, N,N-dimethylacetamide, dimethylsulfoxide and the like. Said ractions can be carried out at temperatures ranging from 0° C. to reflux and for a time ranging from 30 minutes to about 48 hours.

According to step "g" of method A, the conversion of a compound of formula 9 into a compound of formula 10 is accomplished by using hydrazine in a suitable solvent such as tetrahydrofuran, 1,4-dioxane, 1,2-dimethoxyethane, methanol, ethanol, acetonitrile, acetic acid, N,N-dimethylformamide or mixtures thereof at a temperature ranging from 0° C. to reflux and for a time ranging from 30 minutes to about 24 hours.

The intermediate compound of formula (II) can be prepared according to method B described below.

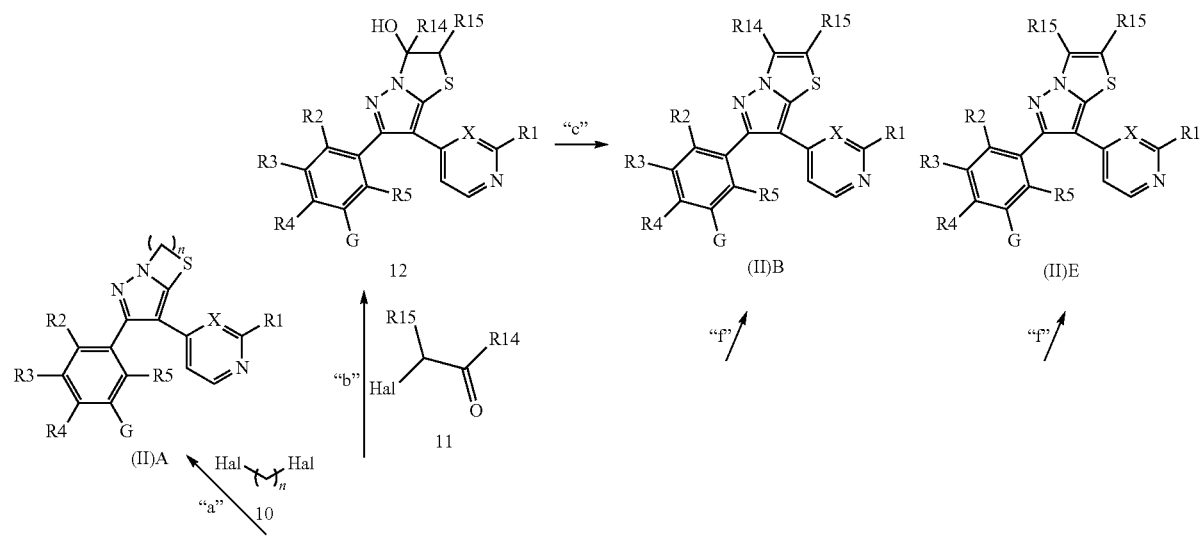

Method B

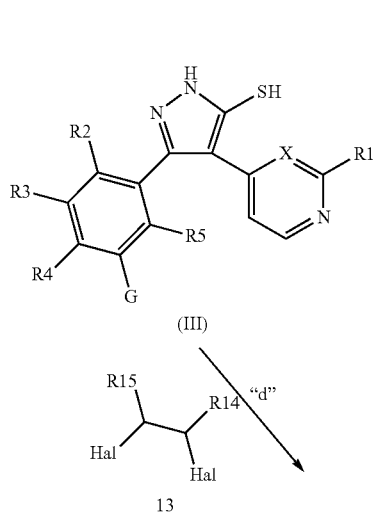

(III)

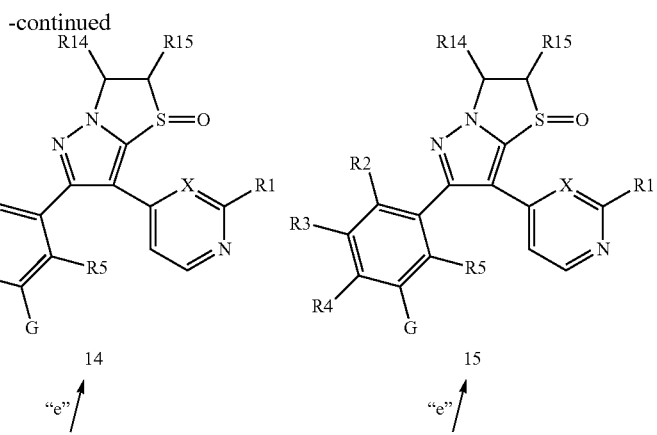

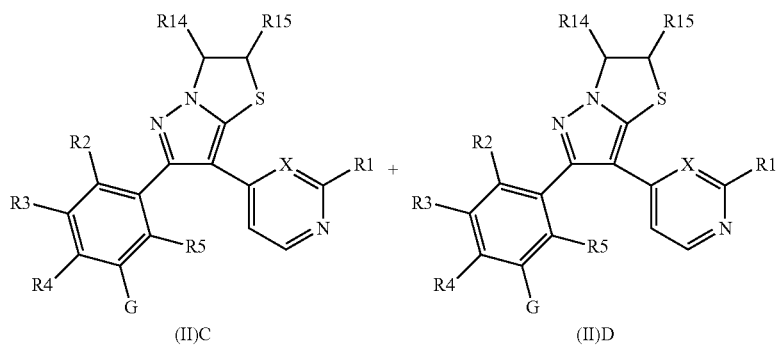

In the above scheme, X, R1, R2, R3, R4, R5, R14, R15, G and n are as defined above, and Hal is halogen.

In a synthetic process for the preparation of a compound of formula (II), which is described in method B, in step "a" a compound of formula (III) is reacted with a suitable terminal alkyl dihalide of formula 10 to form a compound of formula (II)A, i.e. a compound of formula (II) wherein W is $(CH_2)_n$ and n is as defined above. Alternatively, a compound of formula (III) is reacted with an alpha-halo ketoderivative, such as for instance an alkyl bromo pyruvate, or an alkyl 2-bromo-3-oxo-butyrate of formula 11 to give a compound of formula 12. The latter is then dehydrated to form a compound of formula (II)B, i.e. a compound of formula (II) wherein W is C(R14)=C(R15). As another alternative a compound of formula (III) is reacted with a vicinal di-halo derivative, such as, for instance an alkyl, 2,3 dibromo propionate, or 1,2,3 tribromo propane of formula 13 to form a mixture of regioisomeric compounds of formula (II)C, i.e. a compound of formula (II) wherein W is CH(R14)-CH(R15), with the carbon subsituted with R15 close to the sulfur atom of the ring, and (II)D, i.e. a compound of formula (II) wherein W is CH(R15)-CH(R14), with the carbon subsituted with R14 close to the sulfur atom of the ring, which can be conveniently separated and purified by known methods such as silica gel chromatography or preparative HPLC. Compounds (II)C and (II)D as defined above, may then be oxidized to the corresponding sulfoxides of formula 14 and 15 respectively. A compound of formula 14 and 15 respectively may undergo Pummerer rearrengement following elimination, furnishing respectively a compound of formula (II)B, and (II)E, i.e. a compound of formula (II) wherein W is C(R14)=C(R15) with the carbon subsituted with R15 close to the sulfur atom of the ring.

According to step "a" of method B, the condensation of a compound of formula (III) with an alpha-omega dihalo alkane of formula Hal-$(CH_2)$n-Hal, to give a compound of formula (II)A is accomplished using a suitable solvent such as dichloromethane, tetrahydrofuran, 1,4-dioxane, 1,2-dimethoxyethane, methanol, ethanol, isopropanol, acetonitrile, N,N-dimethylformamide, N,N-dimethylacetamide, dimethylsulfoxide and the like. Said raction can be carried out at temperatures ranging from 0° C. to reflux and for a time ranging from 30 minutes to about 48 hours.

According to step "b" of method B, the condensation of a compound of formula (III) with an alpha-halo ketoderivative is accomplished using a suitable solvent such as tetrahydrofuran, 1,4-dioxane, 1,2-dimethoxyethane, methanol, ethanol, isopropanol, acetonitrile, N,N-dimethylformamide, N,N-dimethylacetamide, dimethylsulfoxide and the like, at temperatures ranging from 20° C. to reflux and for a time ranging from 30 minutes to about 48 hours.

According to step "c" of method B, the dehydratation of a compound of formula 12 into a compound of formula (II)B is accomplished using a suitable dehydrating agent, such as, for instance, acetic anhydride, trifluoroacetic anhydride, phosphoryl chloride, and the like in a suitable solvent such as tetrahydrofuran, 1,4-dioxane, 1,2-dimethoxyethane, toluene, and the like, at temperatures ranging from 20° C. to reflux and for a time ranging from 30 minutes to about 48 hours.

According to step "d" of method B, the condensation of a compound of formula (III) with a vicinal dihalo alkane of formula 13, to give a compound of formula (II)C and (II)D is accomplished in a suitable solvent such as dichloromethane, tetrahydrofuran, 1,4-dioxane, 1,2-dimethoxyethane, methanol, ethanol, isopropanol, acetonitrile, N,N-dimethylformamide, N,N-dimethylacetamide, dimethylsulfoxide and the like. Said ractions can be carried out at temperatures ranging from 0° C. to reflux and for a time ranging from 30 minutes to about 48 hours. The compounds of formula (II)C and (II)D may be conveniently separated and purified by known methods such as silica gel chromatography or preparative HPLC.

According to step "e" of method B, the compound of formula (II)C and (II)D is oxidized to the corresponding sulfoxide by reaction with a suitable oxidizing agent, such as oxone, m-chloro perbenzoic acid, and the like. Said reaction is carried out in a suitable solvent such as dichloromethane, tetrahydrofuran, 1,4-dioxane, 1,2-dimethoxyethane, toluene and the like, at temperatures ranging from 0° C. to reflux and for a time ranging from 30 minutes to about 4 hours.

According to step "f" of method B, the compound of formula 14 or 15 is treated with a compound such as acetic anhydride, trifluoroacetic anhydride, phosphoryl chloride and the like, at room temperature in a suitable solvent such as tetrahydrofuran, 1,4-dioxane, 1,2-dimethoxyethane, toluene, and the like, following heating to reflux for a time ranging from 30 minutes to about 48 hours, to yield the compound of formula (II)B and (II)E respectively.

A compound of formula (II)B or (II)E can also be further converted into another compound of formula (II)B or (II)E, said conversion is carried out by one or more of the following reactions:

1) hydrolysis under acid or basic condition of a compound of formula (II)B or (II)E wherein one of R14 and R15 is hydrogen and the other is COR16, wherein R16 is OR17 and R17 is as defined above but not hydrogen, to give the corresponding derivative wherein R17 is hydrogen. This reaction is conducted according to standard procedures as reported in The Chemistry of Carboxylic Acids and Esters, Saul Patai, Interscience Publisher (John Wiley&Sons 1969);
2) amidation of a compound of formula (II)B or (II)E wherein one of R14 and R15 is hydrogen and the other is COR16, wherein R16 is OR17 and R17 is as defined above but not hydrogen, to give the corresponding derivative wherein R16 is NR18R19.
This reaction is conducted by direct reaction with a suitable primary or secondary amines according to standard procedures as reported in The Chemistry of Amides, Saul Patai, Interscience Publisher (John Wiley&Sons 1970);
3) amidation of a compound of formula (II)B or (II)E wherein one of R14 and R15 is hydrogen and the other is COR16, wherein R16 is OR17 and R17 is hydrogen, to give the corresponding derivative wherein R16 is NR18R19; This reaction is conducted by direct reaction with a suitable primary or secondary amines according to standard procedures as reported in The Chemistry of Amides, Saul Patai, Interscience Publisher (John Wiley&Sons 1970).

A compounds of formula (II) prepared according to method B, may be further converted in another compound of formula (II) following procedures well known to those skilled in the art.

For instance, a compound of formula (II)F, i.e. a compound of formula (II) wherein W is W1 which is C(R14)=C(R15) or C(R15)=C(R14), X is a CH group and R1 is hydrogen, or a compound of formula (II)J, i.e. a compound of formula (II) wherein W is as defined above, X is a CH group and R1 is halogen, said compound can further be transformed in another compound of formula (II)G, (II)H, (II)1 or (II)K wherein R1 is respectively NR7R8, NHR7, NH2 or NHCOR9, according to method C described below.

Method C

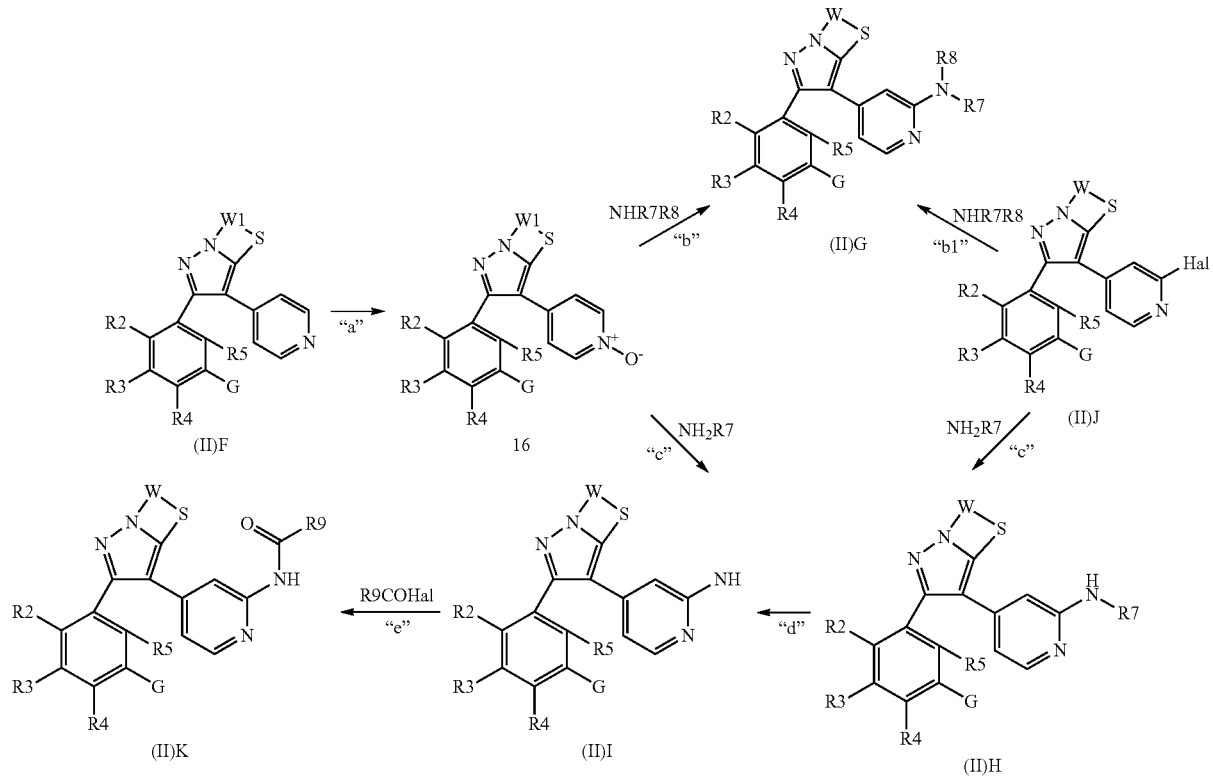

In the above scheme, W, R2, R3, R4, R5, G, R7, R8, R9 and Hal are as defined above, and W1 is C(R14)=C(R15) or C(R15)=C(R14).

In a synthetic process for the preparation of a compound of formula (II)G, (II)H, (11)1 and (II)K which is described in method C, in step "a" the pyridine nitrogen of a compound of formula (II)F is oxidized to form a N-oxide derivative of formula 16. In step "b", and "c" respectively, the reaction of the latter with a suitable electrophilic species such as tosyl anhydride in the presence or followed by treatment with a suitable nucleophile such as a secondary (NHR7R8) or a primary (NH₂R7) amine yields a compound of formula (II)G, wherein and (II)H respectively. Alternatively, in step "b1" and "c1" respectively, a compound of formula (II)J is reacted with a suitable nucleophile such as a secondary (NHR7R8) or a primary (NH₂R7) amine to yield a compound of formula (II)G and (II)H respectively. Optionally in step "d", when R7 is represented by a t-butyl group, a benzyl group or the like, said groups may be removed for instance by treatment with acid or under reductive conditions to yield a compound of formula (11)1. In step "e" the latter may optionally be acylated using a suitable electrophile such as an acyl halide to form a compound of formula (II)K.

According to step "a" of method C, the oxidation of the pyridine nitrogen is carried out using oxidizing agents well-known to those skilled in the art, such as, for instance, hydrogen peroxide in a solvent such as acetic acid or m-chloroperbenzoic acid in solvents such as dichloromethane, acetone, tetrahydrofuran or the like at temperatures ranging from 0° C. to reflux and for a time ranging from 30 minutes to about 48 hours.

According to step "b" and "c" of method C, the transformation of a compound of formula 16 into a compound of formula (II)G or (II)H is accomplished by activating the pyridine N-oxide and reacting it respectively with a secondary or primary amine. Activation is normally carried using a suitable electrophilic reagent, such as oxalyl chloride, trifluoromethanesulfonyl chloride, tosyl chloride, phosphoryl chloride (POCl₃), benzoyl chloride, acetic anhydride, tosyl anhydride and the like, in a solvent such as dichloromethane, tetrahydrofuran, acetonitrile, toluene, trifluoromethyl benzene and the like. Preferred is the use of tosyl anhydride in trifluoromethyl benzene. The reaction is normally carried out in the presence of the secondary or primary amine, and may be carried out at temperatures ranging from 20° C. to reflux and for a time ranging from 30 minutes to about 48 hours.

According to steps "b1" and "c1" of method C, the transformation of a compound of formula (II)J into a compound of formula (II)G or (II)H is accomplished by reacting it respectively with a secondary or primary amine in solvents such as N,N-dimethylformamide, N,N-dimethylacetamide, N-methyl pyrrolidone, dimethylsulfoxide, dichloromethane, tetrandrofuran, dioxane, ethanol and the like, optionally in the presence of a suitable base such as, for instance, K2003, NaOH, triethylamine at temperatures ranging from 20° C. to reflux and for a time ranging from 30 minutes to about 48 hours.

According to step "d" of method C, when a primary amine such as t-butylamine or benzylamine has been used in step b, the alkylic residue of such amine may be removed. The reaction, is normally carried out using strong acids, such as trifluoroacetic acid, optionally in the presence of suitable co-solvent, such as dichloromethane, at temperatures ranging from 20° C. to reflux and for a time ranging from 30 minutes to about 48 hours. Alternatively, said reaction is carried out using reductive conditions, such H2 in the presence of a suitable hydrogenation catalyst. The hydrogenation catalyst is usually a metal, most often palladium, which can be used as such or supported on carbon, in a suitable solvent such as, for instance, tetrahydrofuran, 1,4-dioxane, N,N-dimethylformamide, methanol, ethyl acetate, or a mixture thereof.

According to step "e" of method C, a compound of formula (II)I is converted into the corresponding carboxamide of formula (II)K. It is clear to the skilled person that this reaction can be accomplished in a variety of ways and operative conditions, which are widely known in the art for the preparation of carboxamides. As an example, a compound of formula (II)I is acylated with a compound of formula R9COHal, wherein Hal is an halogen, such as chloride; the reaction is performed in a suitable solvent such as, for instance, dichloromethane, chloroform, tetrahydrofuran, diethyl ether, 1,4-dioxane, acetonitrile, toluene, or N,N-dimethylformamide, in the presence of a suitable base such as triethylamin, diisopropyl ethylamine, DBU and the like at a temperature ranging from about −10° C. to reflux and for a suitable time, for instance from about 30 minutes to about 96 hours.

A compounds of formula (II) prepared according to method B, may be further converted in another compound of formula (II) following procedures well known to those skilled in the art.

For instance, a compound of formula (II)L, i.e. a compound of formula (II) wherein W1 is C(R14)=C(R15) or C(R15)=C (R14), X is nitrogen and R1 is thiomethyl, or a compound of formula (II)P, i.e. a compound of formula (II) wherein W is as defined above, X is nitrogen and R1 is halogen, said compound can further be transformed in another compound of formula (II)M, (II)N or (II)O wherein R1 is respectively NR7R8, NH2 or NHCOR9, according to method D described below.

Method D

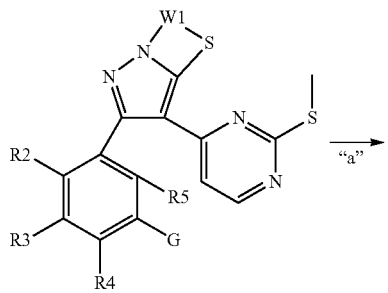

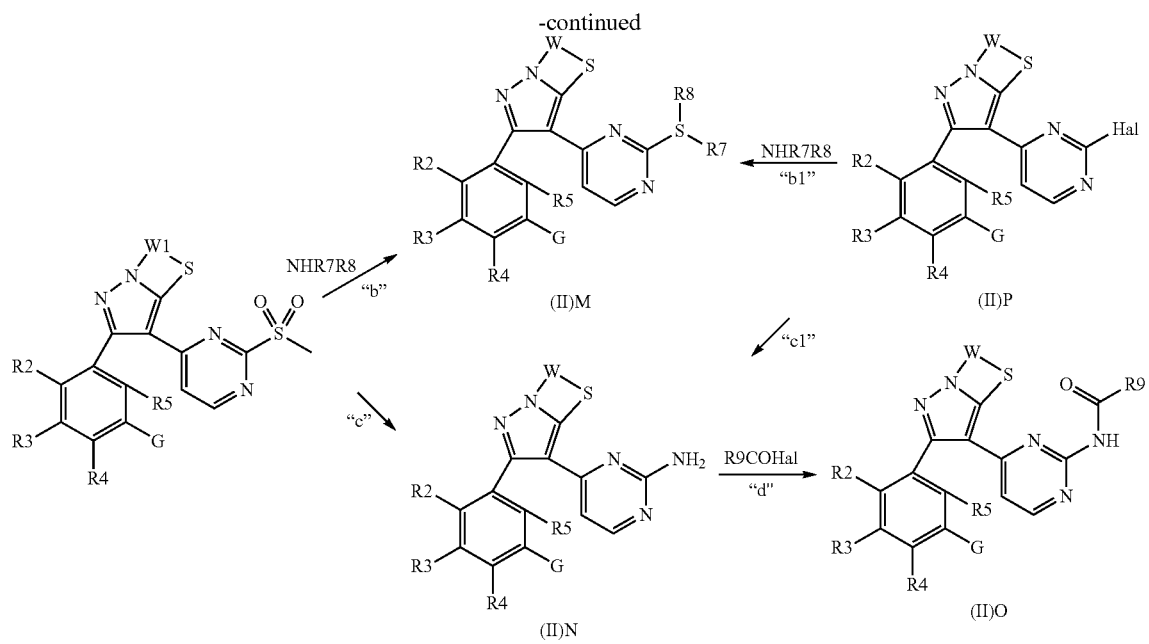

In the above scheme, W, W1, R2, R3, R4, R5, G, R7, R8, R9 and Hal are as defined above.

In a synthetic process for the preparation of a compound of formula (II)M, (II)N and (II)O, which is described in method D, in step "a" the reaction of a compound of formula (II)L with an oxidizing agent yields a sulfonyl derivative of formula 17. In step "b" the latter is treated with with a suitable nucleophile such as a primary or secondary amine of formula NHR7R8 to give a compound of formula (II)M. In step "c" the sulfonyl derivative of formula 17 is treated with ammonium chloride to form a compound of formula (II)N. Alternatively, in step "b1" and "c1", a compound of formula (II)P is reacted with a suitable nucleophile such as a primary or secondary amine of formula (NHR7R8) or with ammonium chloride to yield a compound of formula (II)M and (II)N respectively. A Compound of formula (II)N may optionally be acylated using a suitable electrophile of formula R9COHal, wherein Hal is an halide, such as chloride or the like to form a compound of formula (II)O.

According to step "a" of method D, the oxidation of the thiomethyl group is carried out using oxidizing agents well-known to those skilled in the art, such as, for instance, oxone in a suitable solvent such as tetrahydrofuran, dioxane, acetone, optionally in the presence of water as a cosolvent, or m-chloroperbenzoic acid in solvents such as dichloromethane, acetone, tetrahydrofuran or the like at temperatures ranging from 0° C. to reflux and for a time ranging from 30 minutes to about 48 hours.

According to step "b" and "b1" of method D, the transformation of a compound of formula 17 in a compound of formula (II)M is carried out using a primary or secondary amine of formula R7R8NH in solvents such as N,N-dimethylformamide, N,N-dimethylacetamide, N-methyl pyrrolidone, dimethylsulfoxide, dichloromethane, tetrandrofuran, dioxane, ethanol and the like, optionally in the presence of a suitable base such as, for instance, K$_2$CO$_3$, NaOH, triethylamine at temperatures ranging from 20° C. to reflux and for a time ranging from 30 minutes to about 48 hours.

According to step "c" and "c1" of of method D, the formation of a compound (II)N from an intermediate of formula 17 or a compound of formula (II)P respectively, is accomplished using a solution of ammonia in a suitable solvent, such as, dichloromethane, ethanol and the like, or ammonium salts, such as, for instance ammonium acetate in solvents such as N,N-dimethylformamide, N,N-dimethylacetamide, N-methyl pyrrolidone, dimethylsulfoxide and the like at temperatures ranging from 20° C. to reflux and for a time ranging from 30 minutes to about 48 hours.

According to step "d" of method D, a compound of formula (II)N may be converted in a carboxamide of formula (II)O. It is clear to the skilled person that this reaction can be accomplished in a variety of ways and operative conditions, which are widely known in the art for the preparation of carboxamides. As an example, a compound of formula (II)I is acylated with a compound of formula R9COHal, wherein Hal is an halogen, such as chloride; the reaction is performed as described under step "e" of method C.

The compound of formula (I) can be prepared according to any of the methods E, F, G, H and I described below, provided that the interfering amino groups are protected by the introduction of suitable protecting groups, as can be understood by those skilled in the art.

According to method E described below, starting from a compound of formula (II)1, i.e. a compound of formula (II) wherein G is nitro, or from a compound of formula (II)2, i.e. a compound of formula (II) wherein G is a protected amino group, a compound of formula (I)A, (I)B, (I)C, (I)D, (I)E or (I)F wherein A is respectively NHSO$_2$, NHCOO, NHCON (Y), NHCSNH, NHCO or SO$_2$N(Y) is prepared.

Method E

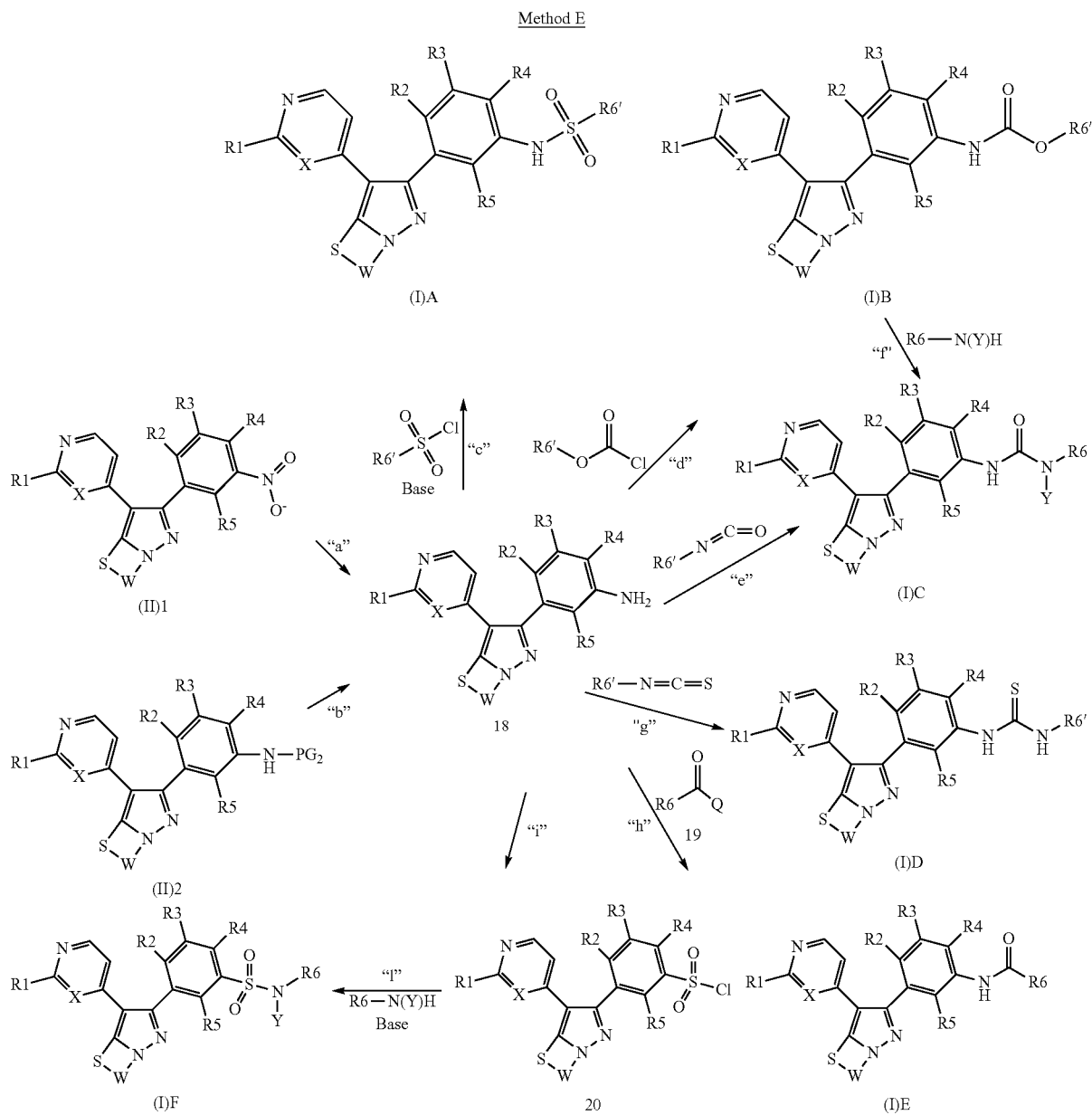

In the above scheme, W, X, R1, R2, R3, R4, R5, R6, and Y are as defined above, R6' is as R6 described above but not hydrogen, Q is a suitable leaving group such as hydroxy or halogen, and PG2 is a suitable protecting group of the amino moiety, such as benzyl, bis-benzyl, p-methoxybenzyl, trityl, phtaloyl, benzyloxycarbonyl, p-nitrobenzyloxycarbonyl, and the like.

In a synthetic process for the preparation of a compound of formula from (I)A to (I)F which is described in method E, in step "a" a compound of formula (II)1 is reduced to give a compound of formula 18 by reducing the nitro group to amino group. In step "b", said compound of formula 18 is obtained by removal of a suitable protecting group of the amino moiety from a compound of formula (II)2. In step "c", "d", "e", "g" and "h" said compound of formula 18 is then reacted with different types of electrophile to provide respectively a compound of formula (I)A, (I)B, (I)C, (I)D and (I)E. In step "f", a compound of formula (I)B is converted into a compound of formula (I)C by reaction with a suitable primary or secondary amine. In step "i" a compound of formula 18 is subjected to a diazotation reaction under the Sandmeier conditions following reaction with $SO_2$ in the presence of hydrochloric acid and a suitable copper catalyst to form a sulfonyl chloride of formula 20. In step "l" the latter compound is reacted with a suitable primary amine to yield a compound of formula (I)F.

According to step "a" of method E, the nitro group of a compound of formula (11)1 is reduced to amino group to yield a compound of formula 18. The reaction may be carried out in a variety of way and operative conditions, which are widely known in the art for reducing a nitro to an amino group. Preferably, this reaction is carried out in a suitable solvent such as, for instance, water, methanol, tetrahydrofuran, 1,4-dioxane, N,N-dimethylformamide, ethyl acetate, or a mixture thereof, in the presence of a suitable reducing agent, such as, for instance, hydrogen and a hydrogenation catalyst, or by treatment with cyclohexene or cyclohexadiene and a hydrogenation catalyst, or by treatment with tin (II) chloride, or by treatment with zinc or zinc (II) chloride and aqueous hydrochloric acid or acetic acid or ammonium chloride, at a temperature ranging from 0° C. to reflux and for a time varying from about 1 hour to about 96 hours. The hydrogenation catalyst is usually a metal, most often palladium, which can be used as such or supported on carbon.

According to step "b" of method E, when the $PG_2$ is a protecting group such as benzyl ($NHCH_2Ph$), bisbenzyl ($N(CH_2Ph)_2$), p-methoxybenzyl, p-methoxyphenyl, trityl, benzyloxycarbonyl, or p-nitrobenzyloxycarbonyl group, deprotection can be accomplished using $H_2$ in the presence of a suitable hydrogenation catalyst. The hydrogenation catalyst is usually a metal, most often palladium, or a metal derivative, such as $Pd(OH)_2$, which can be used as such or supported on carbon, in a suitable solvent such as, for instance, tetrahydrofuran, 1,4-dioxane, N,N-dimethylformamide, methanol, ethyl acetate, or a mixture thereof. Alternatively, said deprotection can be accomplished using strong acids, such as, for instance, sulphuric acid, hydrochloric acid, trifluoroacetic acid, trifluoromethanesulfonic acid or the like in the presence of a suitable solvent such as toluene, acetonitrile, dichloromethane or the like at a temperature ranging from 0° C. to reflux and for a time varying from about 1 hour to about 96 hours. In addition, when such a protecting group is a p-methoxyphenyl group, deprotection can be accomplished also under oxidative conditions, using for instance cerium ammonium nitrate (CAN) in a suitable solvent such as acetonitrile, dioxane, water methylethylketone or mixture thereof, at a temperature ranging from from 0° C. to reflux and for a time varying from about 1 hour to about 24 hours. When said protecting group is represented by a phtaloyl group removal of the protecting group can be accomplished using hydrazine in a suitable solvent such as ethanol, water, dioxane, tetrahydrofuran and the like at a temperature ranging from 0° C. to reflux and for a time varying from about 1 hour to about 96 hours.

According to step "c" of method E, a compound of formula 18 is reacted with a sulfonyl chloride in the presence of a suitable base, such as for instance, pyridine, N-methyl morpholine, diisopropyl ethylamine, in the appropriate solvent such as pyridine, dichloromethane or tetrahydrofuran, at a temperature ranging from 0° C. to reflux and for a time varying from about 1 hour to about 7 days.

According to step "d" of method E, a compound of formula 18 is preferably reacted with the appropriate chloroformate in the appropriate solvent such as tetrahydrofuran, N,N-dimethylformamide, dichloromethane, chloroform, acetonitrile, toluene or mixtures thereof, at a temperature ranging from about −10° C. to reflux and for a time varying from about 30 minutes to about 96 hours. The reaction is normally carried out in the presence of an opportune proton scavenger such as triethylamine, N,N-diisopropylethylamine or pyridine.

According to step "e" of method E, a compound of formula 18 is reacted with the appropriate isocyanate in a suitable solvent such as a dichloromethane or tetrahydrofuran to yield an urea of formula (I)C. The reaction is normally carried out at a temperature ranging from about −10° C. to reflux and for a time varying from about 30 minutes to about 96 hours.

According to step "f" of method E, a compound of formula (I)C is obtained also from a compound of formula (I)B by reaction with an appropriate amine of formula R6N(Y)H. Said reaction is typically carried out in the appropriate solvent such as dimethylsulfoxide, tetrahydrofuran, N,N-dimethylformamide, N,N-dimethylacetamide, acetonitrile, toluene or mixtures thereof, optionally in the presence of a further base such as TEA, DIPEA DBU or an organometallic reagent such as a grignard reagent or trimethyl aluminium, at a temperature ranging from about −10° C. to reflux and for a time varying from about 30 minutes to about 96 hours.

According to step "g" of method E, a compound of formula 18 is reacted with an appropriate thioisocyanate in a suitable solvent such as dichloromethane or tetrahydrofuran to yield a thiourea of formula (I)D. The reaction is normally carried out at a temperature ranging from about −10° C. to reflux and for a time varying from about 30 minutes to about 96 hours.

According to step "h" of method E, a compound of formula 18 is condensed with a derivative of formula 19 to give an amide of formula (I)E. It is clear to the skilled person that this reaction can be accomplished in a variety of ways and operative conditions, which are widely known in the art for the preparation of carboxamides. As an example, when Q is an halogen such as chloride, the reaction is performed in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine. When Q is an hydroxy group, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "i" of method E, the amino group of a compound of formula 18 is subjected to a diazotation reaction under the Sandmeier conditions following reaction with $SO_2$ in the presence of hydrochloric acid and a suitable copper catalyst to form a sulfonyl chloride of formula 20. The diazotation reaction is performed using sodium nitrite in water or aqueous solvents, in the presence of a mineral acid, such as hydrochloric acid, sulphuric acid and the like, or using isoamyl nitrite in a suitable solvent such as dichloromethane, dimethoxyethane, tetrahydrofuran and the like at a temperature ranging from 0° C. to reflux and for a time ranging from 30 minutes to about 24 hours. Next the diazonium salt is typically reacted with $SO_2$ in the presence of CuCl2 in the suitable solvent such as water, acetic acid or mixtures thereof at a temperature ranging from 0° C. to about 50° C. and for a time ranging from 30 minutes to about 6 hours.

According to step "l" of method E, a compound of formula 20 is reacted with a suitable amine to yield a compound of formula (I)F. Said reaction is normally carried out in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction may be carried out in the presence of an opportune proton scavenger such as triethylamine, N,N-diisopropylethylamine or pyridine.

According to method F described below, starting from a compound of formula (II)3, i.e. a compound of formula (II) wherein G is halogen, a compound of formula (I)G or (I)H wherein A is respectively CH$_2$SO$_2$N(Y) or CH$_2$CON(Y) is prepared.

the art, for instance by using lithium hydroxide in the presence of suitable solvents such as mixtures of THF, methanol and water. Said compound of formula 25 in step "e" is then condensed with a suitable amine to form a compound of formula (I)H.

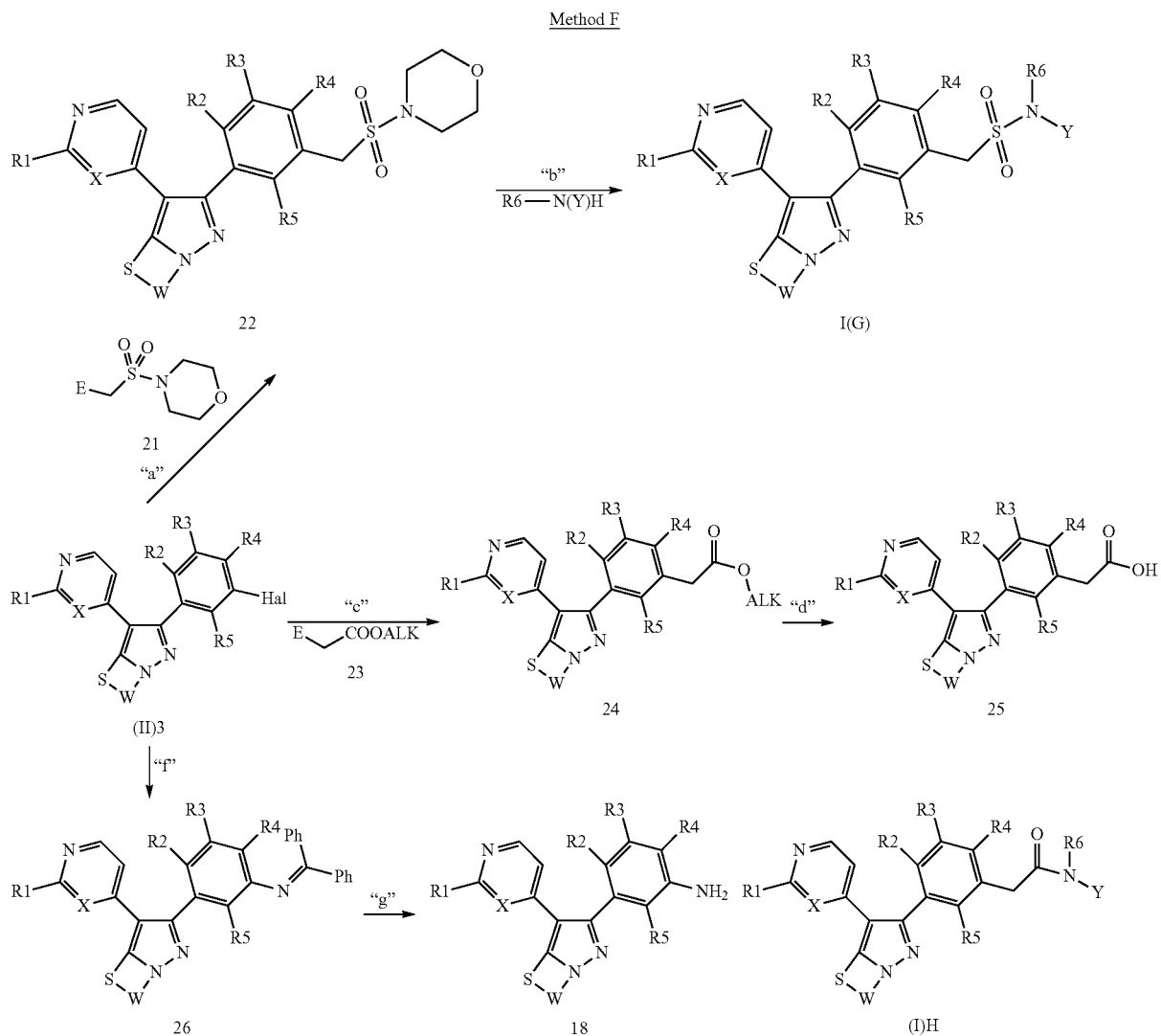

Method F

In the above scheme, W, X, R1, R2, R3, R4, R5, R6, E, Alk, and Y are as defined above, and Hal is halogen, preferably bromine.

In a synthetic process for the preparation of a compound of formula (I)G and (I)H which is described in method F, in step "a" a compound of formula (II)3 is reacted with a suitable methanesulfonamide or alkylsulfonylamidoacetate of formula 21, in the presence of a suitable base, palladium-based catalyst and ligand, to give a compound of formula 22. In step "b" the latter compound is than reacted with a suitable amine to form a compound of formula (I)G.

Alternatively, in step "c" a compound of formula (II)3 is reacted with an alkyl malonate salt in the presence of a suitable copper catalyst to form a compound of formula 24 which in step "d" is then hydrolyzed to the corresponding carboxylic acid of formula 25 by means of any of the methods known in Alternatively, in step "f" a compound of formula (II)3 is aminated under the Buchwald-Hartwig reaction conditions using benzophenone imine, a suitable base and a palladium catalyst to form a compound of formula 26. In step "g" the latter is hydrolyzed under acidic conditions, for instance using hydrochloric acid to form a compound of formula 18 that is subjected to any of the reactions reported in method E shown above.

According to step "a" of method F, the reaction between a compound of formula (II)3 and a suitable methylsulfonamide of formula 21, such as 4-methanesulfonyl-morpholine, is carried out following the conditions reported by Gimm, J. B.; Katcher, M. H.; Witter, D. J.; Northrup, A. B.; (J. Org. Chem. 2007, 72 (21), 8135-8138), using a base such as, for instance, sodium tertbutoxide, a suitable palladium catalyst, such as Pd(OAc)$_2$, a ligand, such as triphenylphosphine or tri tertbutylphosphonium tetrafluoroborate. Said reaction is normally carried out in solvents such as dioxane, dimethoxyethane and the like at a temperature ranging from about 0° C. to reflux and for a suitable time, for instance from about 30 minutes to about 96 hours.

In case an alkylsulfonylamido acetate is used (compounds 21 wherein E is an alkyloxycarbonyl group) said reaction is followed by treatment with a variety of bases, such as, for instance $K_2CO_3$ or sodium amide in a suitable solvent such as 1,4-dioxane, dimethyl sulfoxide N,N-dimethylformamide or the like at a temperature ranging from about 20° C. to reflux and for a suitable time, for instance from about 30 minutes to about 96 hours.

According to step "b" of method F, the reaction between a compound of formula 22 and an amine is normally carried out in a suitable solvent, such as 1,4-dioxane, acetonitrile, toluene, or N,N-dimethylformamide or the like at a temperature ranging from about 20° C. to reflux and for a suitable time, for instance from about 30 minutes to about 96 hours.

According to step "c" of method F, the reaction between a compound of formula (II)3 and a suitable alkyl acetate or alkyl malonate of formula 23, is carried out using a base such as, for instance, sodium hydride, a suitable catalyst, such as CuBr, $Pd(OAc)_2$ or $PdCl_2$ a ligand, such as, for instance triphenylphosphine. Said reaction is normally carried out in solvents such as dioxane, dimethoxyethane and the like at a temperature ranging from about 0° C. to reflux and for a suitable time, for instance from about 30 minutes to about 96 hours.

In case an alkyl malonate is used (a compound of formula 23 where E is an alkyloxycarbonyl group) said reaction is followed by treatment with a base, such as, for instance $K_2CO_3$ or sodium amide in a suitable solvent such as 1,4-dioxane, dimethyl sulfoxide N,N-dimethylformamide or the like at a temperature ranging from about 20° C. to reflux and for a suitable time, for instance from about 30 minutes to about 96 hours.

According to step "d" of method F, the hydrolysis of the alkyl ester of formula 24 is carried out according to well-known methods, for instance in the presence of aqueous alkaline solutions such as aqueous sodium hydroxide or lithium hydroxide in solvents such as tetrahydrofuran, methanol water and mixtures thereof. Said reaction typically requires from 30 minutes to 96 hours and is carried out at a temperature ranging from 0° C. to reflux.

According to step "e" of method F, a compound of formula 25 is condensed with a suitable amine to give an amide of formula (I)H. It is clear to the skilled person that this reaction can be accomplished in a variety of ways and operative conditions, which are widely known in the art for the preparation of carboxamides. As an example, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about –10° C. to reflux and for a suitable time, for instance from about 30 minutes to about 96 hours. Said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about –30° C. to room temperature.

Alternatively, according to step "f" of method F, a compound of formula (II)3 is reacted with a benzophenone imine to give a compound of formula 26. The reaction is conducted in the presence of a suitable base, such as sodium tert-buthoxide, a suitable catlyst, such as, $Pd(dba)_3$, and optionally an additional ligand, such as 2,2'-bis(diphenylphosphino)-1,1'-binaphthyl (BINAP), in a suitable solvent, such as toluene, dimethoxyethane, dioxane and the like at a temperature ranging from about 20° C. to reflux and for a suitable time, for instance from about 30 minutes to about 96 hours.

According to step "g" of method F, the hydrolysis of a compound of formula 26 is accomplished using an acid such as hydrochloric acid in dioxane. Said reaction is normally carried out at a temperature ranging from about 0° C. to 40° C. and for a suitable time, for instance from about 30 minutes to about 96 hours.

A compound of formula 18 can be subjected to any of the reactions carried out according to method E described above.

According to method G described below, starting from a compound of formula (II)4, i.e. a compound of formula (II) wherein G is cyano, a compound of formula (I)I, (I)J, (I)K, (I)L, (I)M or (I)N wherein A is respectively CON(Y), $CH_2NHSO_2$, $CH_2NHCOO$, $CH_2NHCONH$, $CH_2NHCSNH$, or $CH_2NHCO$ is prepared.

Method G

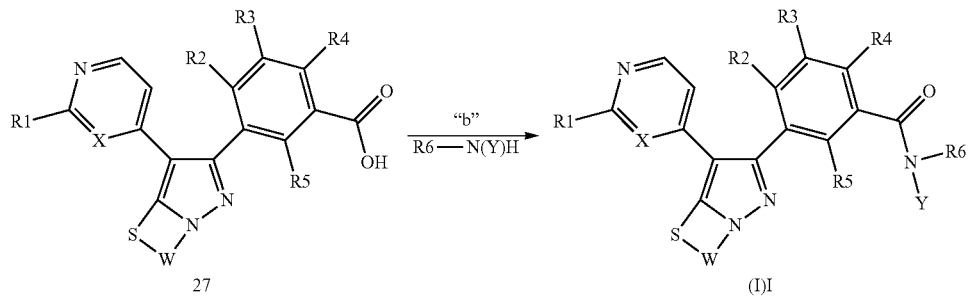

-continued

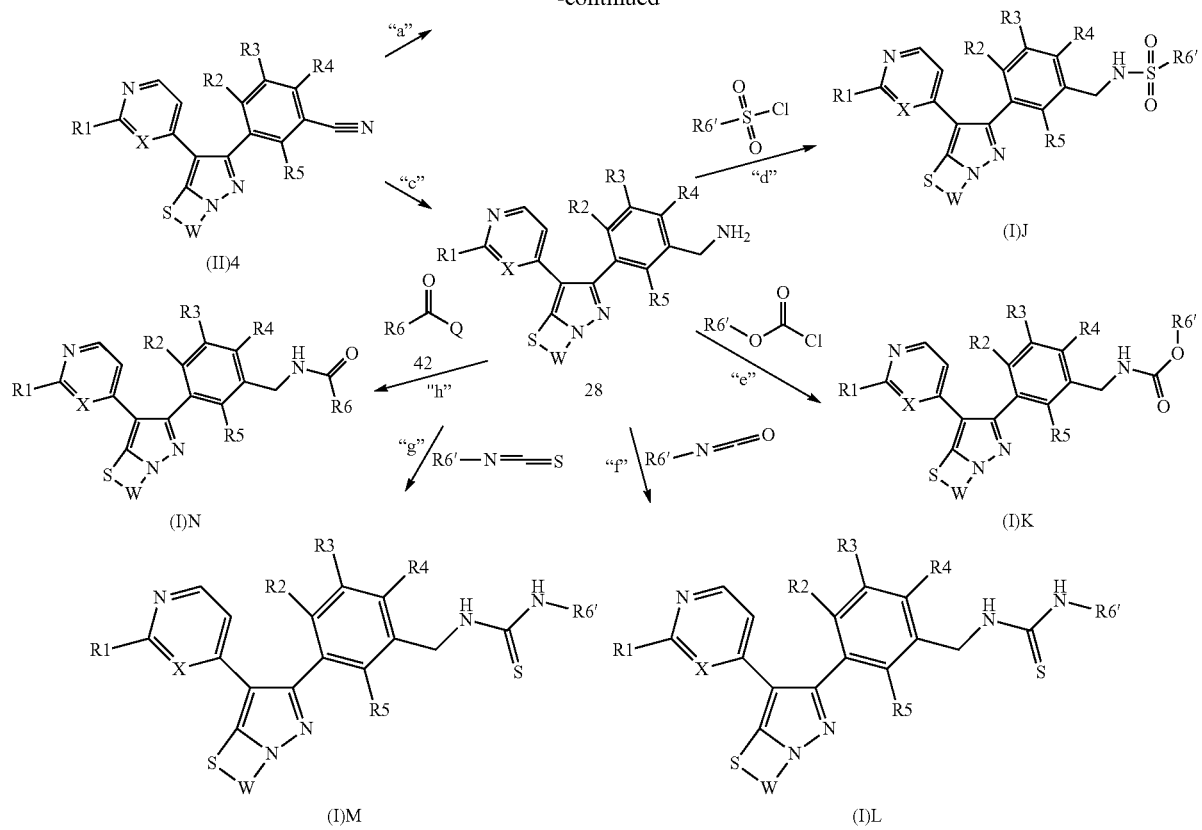

In the above scheme, W, X, R1, R2, R3, R4, R5, R6, R6', Y and Q are as defined above.

In a synthetic process for the preparation of a compound of formula from (I)I to (I)N which is described in method G, in step "a" the cyano group of a compound of formula (II)4 is hydrolized to form a compound of formula 27. The latter in step "b" is then condensed with a suitable amine to form a compound of formula (I)I.

Alternatively in step "c" the cyano group of a compound of formula (II)4 is reduced to form a compound of formula 28.

In step "d", "e", "f, "g" and "h" said compound of formula 28 is then reacted with different types of electrophile to provide respectively a compound of formula (I)J, (I)K, (I)L, (I)M and (I)N.

According to step "a" of method G, the hydrolysis of the cyano group is accomplished by using any of the method known in the art, preferably by using aqueous hydrochloric acid under microwave heating at temperature ranging from 80 to 200° C. for a time between 3 and 120 minutes.

According to step "b" of method G, a compound of formula 27 is transformed in an amide of formula (I)I by condensation with a suitable amine. It is clear to the skilled person that this reaction can be accomplished in a variety of ways and operative conditions, which are widely known in the art for the preparation of carboxamides. As an example, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. Said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step "c" of method G, a compound of formula (II)4 is reduced into a compound of formula 28 by using a suitable reducing agent, for instance lithium alluminium hydride, lithium boron hydride, borane dimethylsulfide complex, borane or the like, in a suitable solvent such as tetrahydrofuran, diethyl ether, toluene, dichloromethane, diglyme and the like, at temperature ranging from −50 to reflux, for a suitable reaction time, for instance, between 30 minutes and 48 hours.

Steps from "d" to "h" of method G are respectively carried out as described under step "c" to "h" of method E.

According to method H described below, starting from a compound of formula (II)5, i.e. a compound of formula (II) wherein G is a suitable carboxylic ester, a compound of formula (I)O wherein A is $CH_2SO_2N(Y)$ is prepared.

Method H

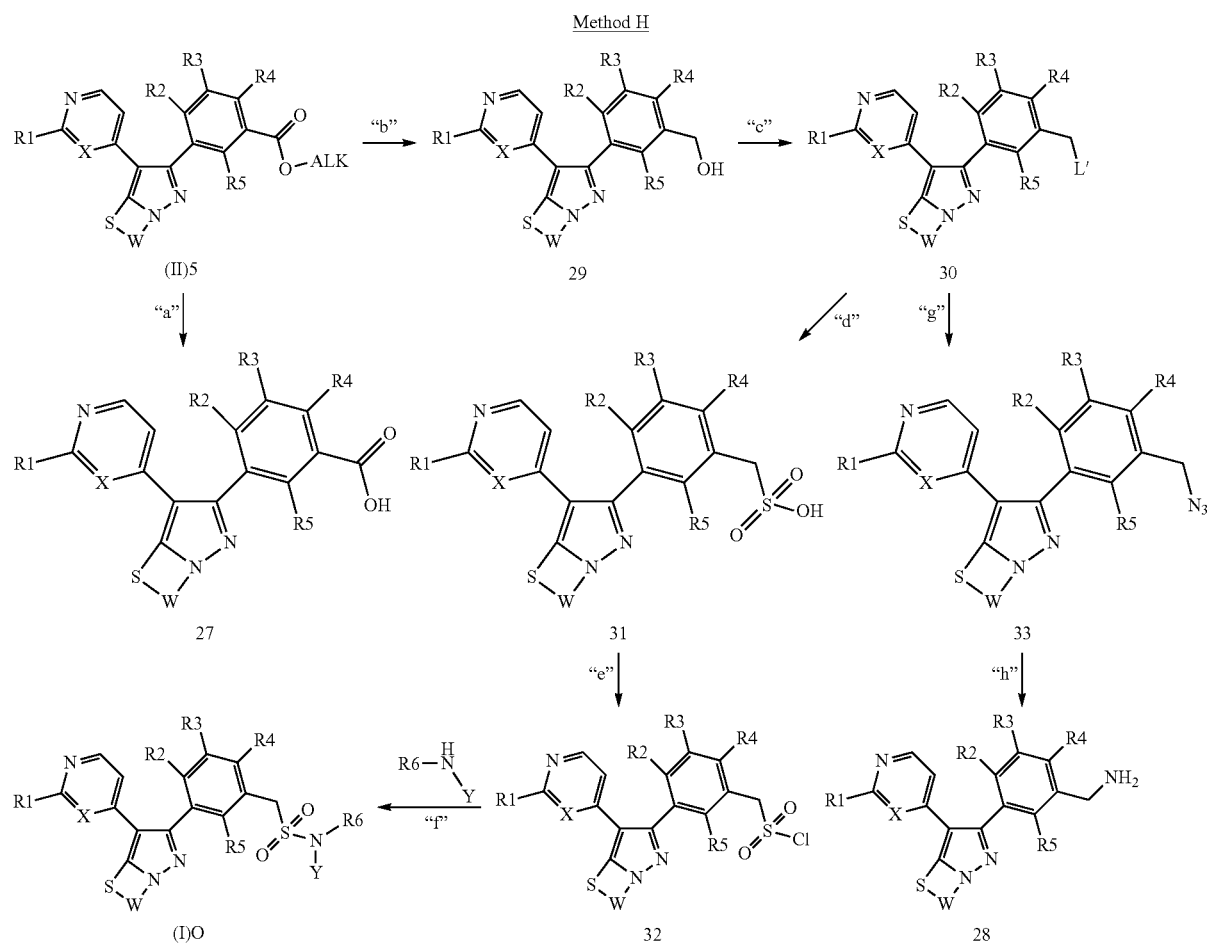

In the above scheme, W, X, R1, R2, R3, R4, R5, R6 and Alk are as defined above, and L' is a leaving group, such as a halogen atom, a tosylate, mesylate or triflate.

In a synthetic process described in method H, in step "a" the alkoxycarbonyl group of a compound of formula (II)5 is hydrolyzed to give a compound of formula 27. The latter is then subjected to an amidation reaction according to what described in method G, step "b".

Alternatively in step "b", the alkoxycarbonyl group of a compounds (II)5 is reduced to give a compound of formula 29.

In step "c" the hydroxy group of the latter is then replaced by a more suitable leaving group, for instance bromine, a tosylate, mesylate or triflate.

In step "g", a compound of formula 30 is reacted with sodium azide to give a compound of formula 33. In step "h", the latter is reduced to form a compound of formula 28 that is further functionalized following treatment with the appropriate electrophile as reported in method G, steps "d" to "h".

Alternatively, in step "d" a compound of formula 30 is reacted with a suitable nucleophile such as sodium sulfite, to form a compound of formula 31. In step "e" the latter is then transformed in the corresponding chloride derivative and then in step "f" the latter is treated with a suitable amine to give a compound of formula (I)O.

According to step "a" of method H, the hydrolysis of the alkyl ester is carried out according to well-known methods, for instance in the presence of aqueous alkaline solutions such as aqueous sodium hydroxide or lithium hydroxide in solvents such as tetrahydrofuran, methanol water and mixtures thereof. Said reaction typically requires from 30 minutes to 96 hours and is carried out at a temperature ranging from 0° C. to reflux.

According to step "b" of method H, the reduction of a compound of formula (II)5 is carried out by using a suitable reducing agent, for instance lithium alluminium hydride, lithium boron hydride, borane or the like, in a suitable solvent such as tetrahydrofuran, diethyl ether, toluene, dichloromethane and the like, at temperature ranging from −50 to reflux, for a suitable reaction time, for instance, between 30 minutes and 48 hours.

According to step "c" of method H, the hydroxy group of a compound of formula 29 is transformed in a more suitable leaving group following procedures well known in the art. For instance, its transformation in a bromine atom can be accomplished using an appropriate brominating agent such as $Ph_3PBr_2$, $PBr_3$, $SOBr_2$ or the like in a suitable solvent such as dichloromethane, tetrahydrofuran, diethyl ether, toluene, and the like, for a time ranging between 30 minutes to 24 hours and is carried out at a temperature ranging from 0° C. to reflux. The transformation of the hydroxy group in a a tosylate, mesylate or triflate group is usually carried out using suitable reagents such as, for instance, tosyl chloride, mesyl chloride, trifluoromethanesulfonyl chloride respectively.

According to step "d" of method H, a compound of formula 30 is reacted with reagents such as sodium sulfite in solvents such as water, N,N-dimethylformamide, acetone or mixture thereof, optionally in the additional presence of a compound such as tetrabutyl ammonium bromide or the like, at a temperature ranging from 20° C. to reflux and for a time ranging from 30 minutes to about 24 hours.

According to step "e" of method H, a compound of formula 31 is reacted with reagents such as PCl$_5$, POCl$_3$, SOC$_2$, (COCl)$_2$ or the like, in a suitable solvent such as tetrahydrofuran, dichloromethane or the like at a temperature ranging from 20° C. to reflux and for a time ranging from 30 minutes to about 24 hours to form compounds of formula 32.

According to step "f" of method H, a compound of formula 30 is reacted with a suitable amine to yield a compound of formula (I)O. Said reaction is normally carried out in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction may be carried out in the presence of an opportune proton scavenger such as triethylamine, N,N-diisopropylethylamine or pyridine.

Conversion of a compound of formula 30 into a compound of formula 28 can be accomplished in a number of ways and operative conditions well established among those skilled in the art. Just as an example a two-step sequence involving the formation of an alkyl azide of formula 29 and its reduction to an amino compound of formula 28 is reported here.

Accordingly, in step "g" of method H, a compound of formula 30 is reacted with a compound such as sodium azide in a solvent such as N,N-dimethylformamide, acetone, tetrahydrofuran, ethanol at a temperature ranging from about 20° C. to reflux and for a suitable time, for instance from about 30 minutes to about 96 hours.

According to step "h" of method H, a compound of formula 29 is reduced to form a compound of formula 28. Said reduction is accomplished using any suitable reducing agent such as, for instance, PPh$_3$, SnCl$_2$, BH$_3$ or the like in suitable solvent such as tetrahydrofuran, ethanol N,N-dimethylformamide or the like at a temperature ranging from about 20° C. to reflux and for a suitable time, for instance from about 30 minutes to about 96 hours.

A compound of formula (I) prepared according to method E, method F, method G or method H may be further converted into another compound of formula (I) following procedures well known to those skilled in the art.

For instance, a compound of formula (I)Q, i.e. a compound of formula (I) wherein W is W1 which is C(R14)=C(R15) or C(R15)=C(R14), X is a CH group and R1 is hydrogen or a compound of formula (I)V, i.e. a compound of formula (I) wherein wherein W is as defined above, X is a CH group and R1 is halogen, said compound can further be transformed into another compound of formula (I)R, (I)S, (I)T or (I)U wherein R1 is respectively NR7R8, NHR7, NH$_2$ or NHCOR9, according to method J described below.

Method J

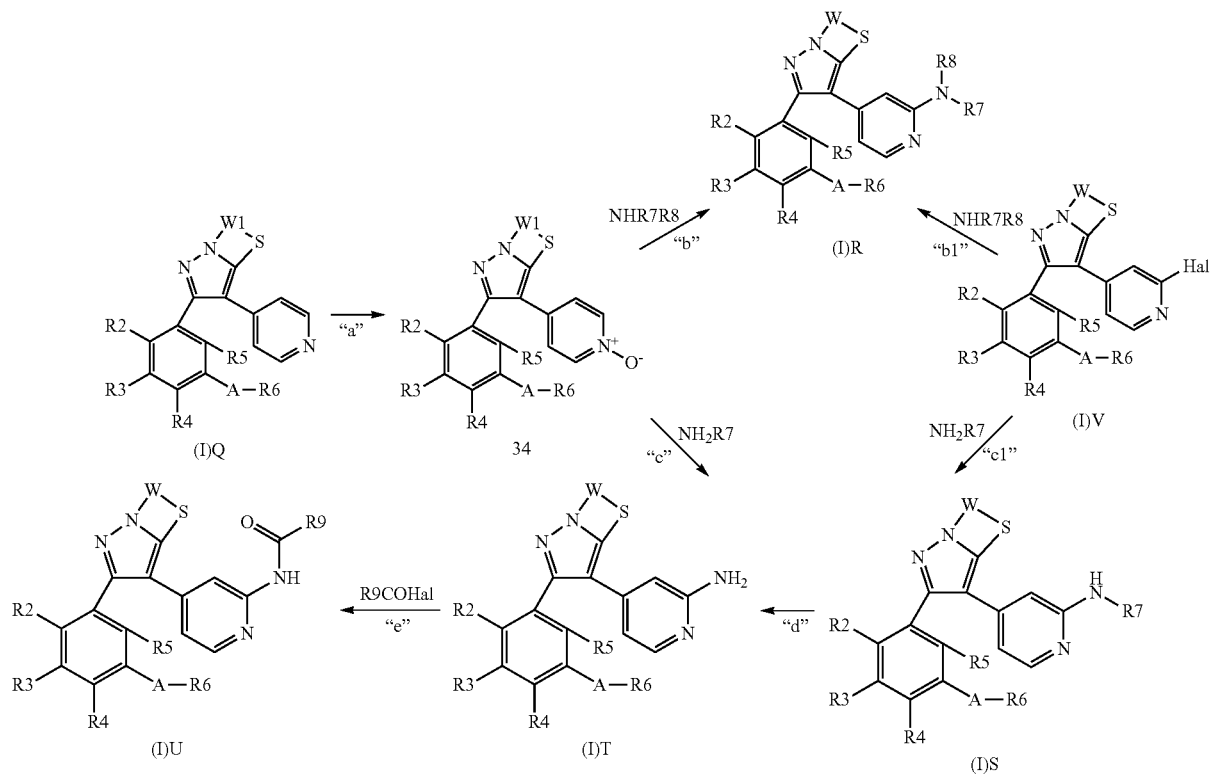

In the above scheme, W, W1, R2, R3, R4, R5, A, R6, R7, R8, R9 and Hal are as defined above.

In a synthetic process for the preparation of a compound of formula (I)R, (I)S, (I)T and (I)U which is described in method J, in step "a" the pyridine nitrogen of a compound of formula (I)Q is oxidized to form a N-oxide derivative of formula 34. In step "b" and "c" respectively, the reaction of the latter with a suitable electrophilic species such as tosyl anhydride in the presence or followed by treatment with a suitable nucleophile such as a secondary (NHR7R8) or a primary (NH2R7) amine yields a compound of formula (I)R and (I)S respectively. Alternatively, in step "b1" and "c1" respectively, a compound of formula (I)V is reacted with a suitable nucleophile such as a secondary (NHR7R8) or a primary (NH₂R7) amine to yield a compound of formula (I)R and (I)S respectively. Optionally in step "d", when R7 is represented by a t-butyl group, a benzyl group or the like, said group is removed for instance by treatment with acid or under reductive conditions to yield a compound of formula (I)T. In step "e" the latter is optionally acylated using a suitable electrophile such as an acyl chloride to form a compound of formula (I)U.

The reactions of steps "a", "b", "c", "d", "c1", "d1" and "e" of method J are accomplished analogously to those of steps "a", "b", "c", "d", "c1", "d1" and "e" of method C shown above.

A compound of formula (I) prepared according to method E, method F, method G, method H or method I may be further converted into another compound of formula (I) following procedures well known to those skilled in the art.

For instance, a compound of formula (I)W, i.e. a compound of formula (I) wherein W is W1 which is C(R14)=C(R15) or C(R15)=C(R14), X is nitrogen and R1 is thiomethyl or a compound of formula (I)AA, i.e. a compound of formula (I) wherein W is as defined above, X is nitrogen and R1 is halogen, said compound can further be transformed into another compound of formula (I)X, (I)Y or (I)Z wherein R1 is respectively NR7R8, NH₂ or NHCOR9, according to method K described below.

Method K

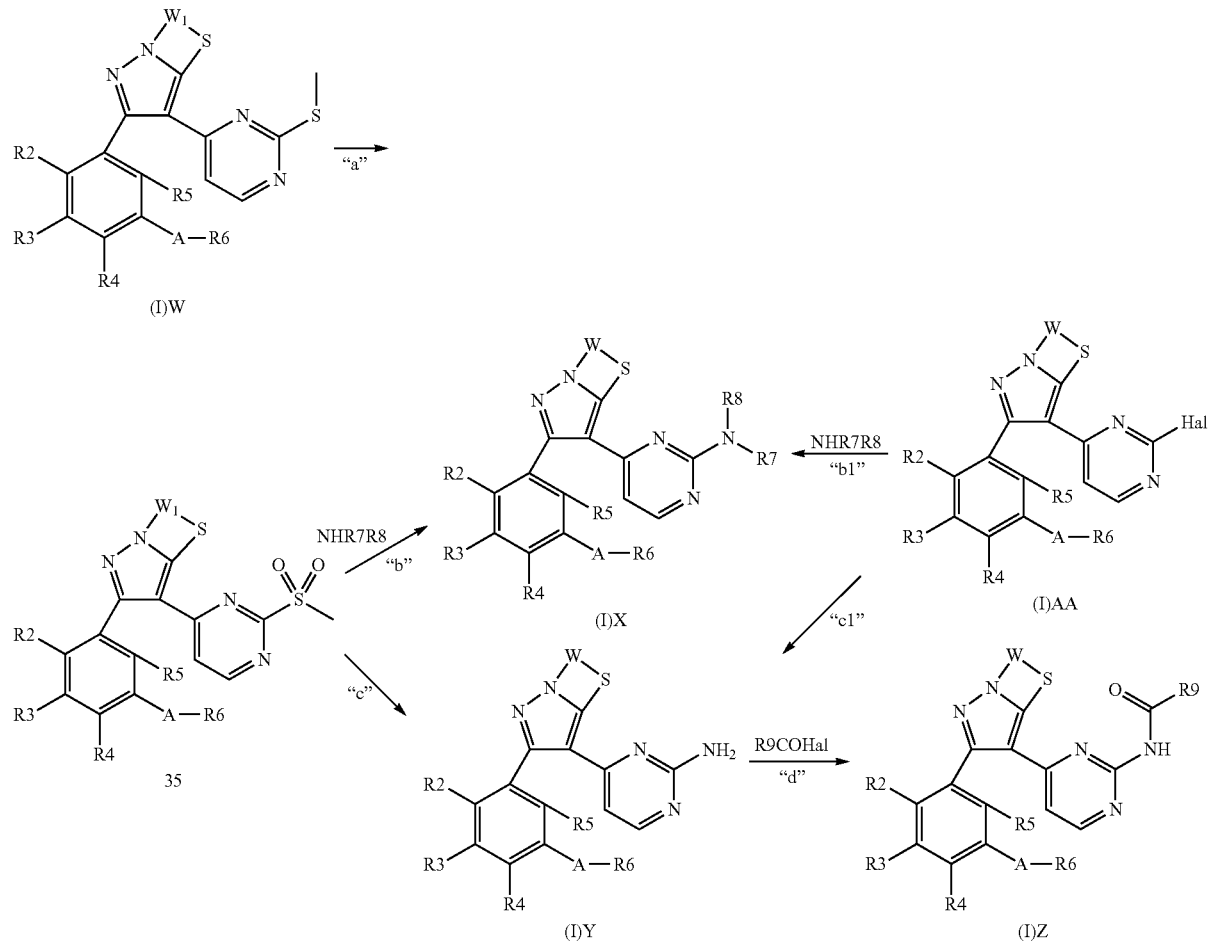

In the above scheme, W, W1, R2, R3, R4, R5, R6, A, R7, R8, R9 and Hal are as defined above.

In a synthetic process for the preparation of compounds of formula (I)X, (I)Y and (I)Z which is described in method K, in step "a" the reaction of a compound of formula (I)W with an oxidizing agent yields a sulfonyl derivative of formula 35. In step "b" the latter is treated with with a suitable nucleophile such as a primary or secondary amine of formula NHR7R8 to give a compound of formula (I)X. In step "c" the sulfonyl derivative of formula 35 is treated with ammonium chloride to form a compound of formula (I)Y. Alternatively, in step "b1" and "c1", a compound of formula (I)AA is reacted with a suitable nucleophile such as a primary or secondary amine of formula (NHR7R8) or with ammonium chloride to yield a compound of formula (I)X and (I)Y respectively. A compound of formula (I)Y is optionally acylated using a suitable electrophile of formula R9COHal, wherein Hal is an halide, such as chlorid or the like to form a compound of formula (I)Z.

The reactions of steps "a", "b", "c", "b1", "c1" and "d" of method K are accomplished analogously to those of steps "a", "b", "c", b1","c1" and "d" of method D shown above.

A compound of formula (I) prepared according to method E, method F, method G, method H or method I may be further converted into another compound of formula (I) following procedures well known to those skilled in the art.

For instance, a compound of formula (I)AB, i.e. a compound of formula (I) wherein W is W2 which is CH(R14)-CH(R15), CH(R15)-CH(R14) or (CH$_2$)$_n$ and X and R1 are as defined above, said compound can further be transformed into another compound of formula (I)AC, i.e. a compound of formula (I) wherein W is W2 which is as defined above and m is 1, according to method L described below.

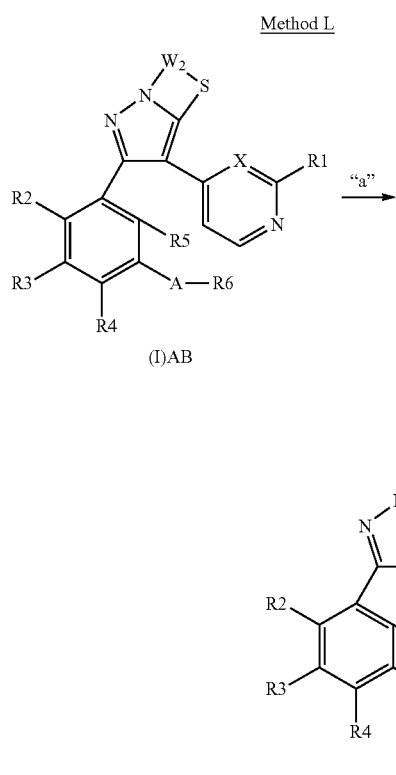

In the above scheme, R1, R2, R3, R4, R5, A, R6 and m are as defined above, W2 is CHR14CHR15 or (CH2)m, wherein n, R14 and R15 are as defined above.

In a synthetic process for the preparation of a compound of formula (I)AC, which is described in method L, in step "a" a compound of formula (I)AB is oxidized to a compound of formula (I)AC.

According to step "a" of method L, the oxidation of the sulfur atom is accomplished using any suitable oxidizing agent such as, for instance m-chloroperbenzoic acid (mCPBA), oxone, sodium periodate and the like in a suitable solvent such as, for instance, dichloromethane, acetone, tetrahydrofuran, acetonitrile at a temperature ranging from about −78° C. to reflux and for a suitable time, for instance from about 30 minutes to about 96 hours.

For instance, a compound of formula (I)P', i.e. a compound of formula (I) wherein A is oxygen and R6 is optionally substituted alkyl, said compound can further be transformed into another compound of formula (I)P wherein R6 is hydrogen, according to method I described below.

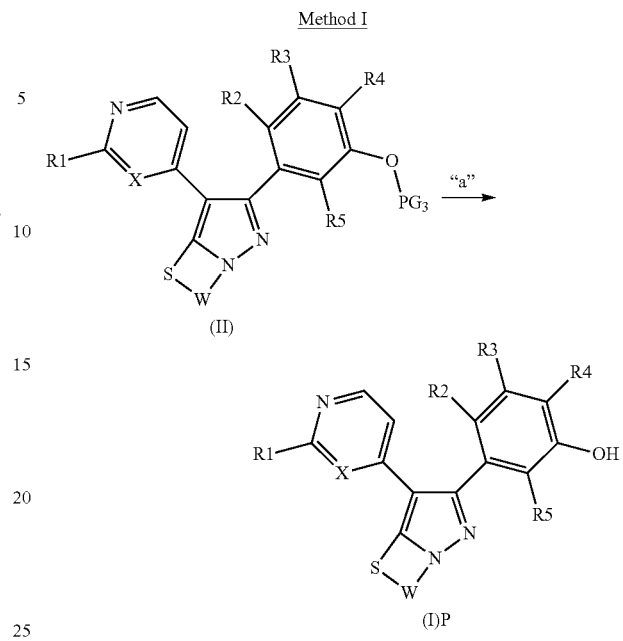

In the above scheme, W, X, R1, R2, R3, R4 and R5 are as defined above, and PG3 is a suitable protecting group of the hydroxyl moiety, such as methyl, benzyl, p-methoxybenzyl, trityl and the like.

In a synthetic process described in method I, a compound of formula (I)P is obtained by removal of the protecting group PG$_3$ from a compound of formula (I)P'. It is readily understood by those skilled in the art, that a variety of methods, which are well known in the art, can be used to remove such a protecting group depending on the nature of the PG$_3$.

According to step "a" of method I, when the PG$_3$ is a protecting group such as a methyl group, deprotection can be accomplished using a boron or alluminium trihalide, such as BBr$_3$ or AlCl$_3$ in a suitable solvent such as dichloromethane, nitrobenzene or the like, or using hydrogen bromide or iodide in a suitable solvent such as, for instance acetic acid. Said reactions are normally carried out at a temperature ranging from about −20° C. to reflux and for a suitable time, for instance from about 30 minutes to about 96 hours.

When said protecting group is, for instance, benzyl, p-methoxybenzyl or trityl, transformation of a compound of formula (I)P' into a compound of formula (I) is accomplished using strong acids such as for instance trifluoroacetic acid in a suitable cosolvent such as dichloromethane at temperature ranging from 20° C. to reflux or above, provided that the reaction is carried out in a sealed vial heating for instance with a microwave oven, for a time ranging from 30 minutes to about 24 hours.

A compound of formula (I)P prepared according to method I may be further converted into another compound of formula (I)P following procedures well known to those skilled in the art.

As an example, a compound of formula (I)P wherein R4 and R5 are both hydrogen, can be transformed in another compound of formula (I)P wherein both R4 and R5 are bromine according to the procedure reported in: S. Fujisaki, H. Eguchi, A. Omura, A. Okamoto, A. Nishida *Bull. Chem. Soc. Jpn.* 1993, 66, 1576-1579.

All those with ordinary skills in the art will appreciate that any transformation performed according to said methods may require standard modifications such as, for instance, protection of interfering groups, change to other suitable reagents known in the art, or make routine modifications of reaction conditions.

The starting materials of the process object of the present invention, comprehensive of any possible variant, as well as any reactant thereof, are known compounds and if not commercially available per se may be prepared as described in the experimental section.

Pharmacology

Assays
In Vitro Cell Proliferation Assay

Exponentially growing human melanoma cells A375 (with a mutated B-RAF) and human melanoma cells Mewo (with wild-type B-Raf) were seeded and incubated at 37° C. in a humidified 5% CO2 atmosphere. After 24 hours, scalar doses of the compound were added to the medium and cells oncubated for 72 hours. At the end of treatment, cells were washed and counted. Cell number was determined by a cellular adenosine triphosphate monitoring system. Cell proliferation was compared to control cells and the concentration inhibiting cell growth by 50% was calculated.

p-MAPK (T202/Y204) ArrayScan Assay

A375 human melanoma cells, having a mutated B-RAF, are seeded in 384-well poly-lysine coated plates (Matrix) at a density of 1000 cells/well with appropriate medium supplemented with 10% FCS and incubated for 16-24 hours. Cells are treated for 1.5 or 2 hours with increasing doses of compounds (starting dose 10 μM, dilution factor 2.5). At the end of the treatment cells are fixed with p-formaldehyde 3.7% for 15-30 min, then washed twice with D-PBS (80 l/well) and permeabilized with D-PBS containing 0.1% Triton X-100 and 1% BSA (Sigma-Aldrich) for 15 minutes at room temperature (staining solution). Anti-phospho-MAPK (T202/Y204) monoclonal antibody E10 (Cell Signaling, cat. #9106) diluted 1:100 is added in staining solution and incubated for 1 hour at 37° C. After removal of antibody solution, the anti-mouse Cy™2-conjugated (Green) secondary antibody (Amersham) diluted 1:500 in staining solution containing 2 g/ml DAPI is added. The plate is incubated for 1 hour at 37° C., washed twice and red with Cellomics' ArrayScan VTI (4 fields/well, CytoNucTrans algorithm).

The parameter "MEAN_RingAvgIntenCh2", which measures the mean cytoplasmatic fluorescence intensity associated to p-MAPK staining, is reported as the final result.

B-RAF mutations, that constitutively activate the kinase, have been identified in the majority of melanoma and a large fraction of colorectal and papillary thyroid carcinoma. The growth of cells with activated B-RAF strictly depends on B-RAF activity.

Given the above assays, the compounds of formula (I) result to posses a remarkable activity in inhibiting cell proliferation, with $IC_{50}$ values lower than 10 μM on the cell line with mutated B-Raf (A375), and higher on the cell line with wild-type B-Raf (Mewo), as reported in the following table.

In the same table the data obtained with compounds of formula (I) in the ArrayScan assay are also reported and demonstrate the ability of the compounds of formula (I) to inhibit the signal transduction pathway controlled by B-RAF activation in A375 cell line with mutated B-RAF. The IC50 values are always lower than 10 μM and are in agreement with the $IC_{50}$ values obtained in the proliferation assay on the same cell line, confirming that the antiproliferative activity of the compounds is due to the inhibition of B-RAF activity.

TABLE 1

Proliferation and Array Scan data

| | | Proliferation | | Array Scan |
|---|---|---|---|---|
| Cpd. N° | Chemical Name | A375 $IC_{50}$ (M) | Mewo $IC_{50}$ (M) | A375 $IC_{50}$ (M) |
| 1 | 1-(4-Chloro-phenyl)-3-[3-(3-pyridin-4-yl-6,7-dihydro-5H-pyrazolo[5,1-b][1,3]thiazin-2-yl)-phenyl]-urea | 2.48 | 3.59 | 7.37 |
| 2 | 1-[3-(3-Pyridin-4-yl-6,7-dihydro-5H-pyrazolo[5,1-b][1,3]thiazin-2-yl)-phenyl]-3-p-tolyl-urea | 3.69 | 7.25 | 5.57 |
| 3 | 1-[3-(3-Pyridin-4-yl-6,7-dihydro-5H-pyrazolo[5,1-b][1,3]thiazin-2-yl)-phenyl]-3-(4-trifluoromethyl-phenyl)-urea | 0.91 | 2.54 | 0.77 |
| 4 | 3-Fluoro-N-[3-(3-pyridin-4-yl-6,7-dihydro-5H-pyrazolo[5,1-b][1,3]thiazin-2-yl)-phenyl]-benzenesulfonamide | 7.51 | >10 | 1.62 |
| 5 | 1-[3-(7-Pyridin-4-yl-2,3-dihydro-pyrazolo[5,1-b]thiazol-6-yl)-phenyl]-3-(4-trifluoromethyl-phenyl)-urea | 0.43 | 2.63 | 0.60 |
| 6 | 1-(4-Chloro-phenyl)-3-[3-(7-pyridin-4-yl-2,3-dihydro-pyrazolo[5,1-b]thiazol-6-yl)-phenyl]-urea | 2.33 | 5.95 | 1.38 |
| 7 | 3-(7-Pyridin-4-yl-2,3-dihydro-pyrazolo[5,1-b]thiazol-6-yl)-phenol | 0.95 | >10 | 0.75 |
| 8 | 3-(3-Pyridin-4-yl-6,7-dihydro-5H-pyrazolo[5,1-b][1,3]thiazin-2-yl)-phenol | 1.51 | >10 | 2.04 |
| 9 | 2,5-Difluoro-N-[3-(3-pyridin-4-yl-6,7-dihydro-5H-pyrazolo[5,1-b][1,3]thiazin-2-yl)-phenyl]-benzenesulfonamide | 1.28 | 4.29 | 0.46 |
| 10 | 3-(1,1-Dioxo-7-pyridin-4-yl-2,3-dihydro-1H-pyrazolo[5,1-b]thiazol-6-yl)-phenol | 1.98 | >10 | 0.62 |
| 11 | 2,5-Difluoro-N-[3-(7-pyridin-4-yl-2,3-dihydro-pyrazolo[5,1-b]thiazol-6-yl)-phenyl]-benzenesulfonamide | 0.66 | >10 | 0.26 |

TABLE 1-continued

Proliferation and Array Scan data

| | | Proliferation | | Array Scan |
|---|---|---|---|---|
| Cpd. N° | Chemical Name | A375 IC$_{50}$ M) | Mewo IC$_{50}$ (M) | A375 IC$_{50}$ (M) |
| 12 | N-[3-(3-Pyridin-4-yl-6,7-dihydro-5H-pyrazolo[5,1-b][1,3]thiazin-2-yl)-phenyl]-2-(4-trifluoromethyl-phenyl)-acetamide | 3.88 | >10 | 6.39 |
| 13 | Furan-2-sulfonic acid [3-(3-pyridin-4-yl-6,7-dihydro-5H-pyrazolo[5,1-b][1,3]thiazin-2-yl)phenyl]-amide | 9.28 | >10 | 3.03 |
| 14 | Thiophene-3-sulfonic acid [3-(3-pyridin-4-yl-6,7-dihydro-5H-pyrazolo[5,1-b][1,3]thiazin-2-yl)-phenyl]-amide | 7.07 | >10 | 4.69 |
| 15 | N-(4-tert-Butyl-phenyl)-3-(7-pyridin-4-yl-2,3-dihydro-pyrazolo[5,1-b]thiazol-6-yl)-benzamide | 0.68 | 3.09 | 0.48 |
| 17 | 6-[3-(2,5-Difluoro-benzenesulfonylamino)-phenyl]-7-pyridin-4-yl-pyrazolo[5,1-b]thiazole-3-carboxylic acid amide | 1.34 | >10 | 1.17 |
| 18 | 1-(4-tert-Butyl-phenyl)-3-[3-(7-pyridin-4-yl-2,3-dihydro-pyrazolo[5,1-b]thiazol-6-yl)-phenyl]-urea | 2.16 | >10 | 2.29 |
| 19 | 1-[3-(1-Oxo-7-pyridin-4-yl-2,3-dihydro-pyrazolo[5,1-b]thiazol-6-yl)-phenyl]-3-(4-trifluoromethyl-phenyl)-urea | 7.68 | >10 | 4.69 |
| 20 | 3-(7-Pyridin-4-yl-pyrazolo[5,1-b]thiazol-6-yl)-phenol | 1.17 | >10 | 0.36 |
| 21 | 2,5-Difluoro-N-[3-(7-pyridin-4-yl-pyrazolo[5,1-b]thiazol-6-yl)-phenyl]-benzenesulfonamide | 3.13 | >10 | 0.21 |
| 22 | 1-[3-(7-Pyridin-4-yl-pyrazolo[5,1-b]thiazol-6-yl)-phenyl]-3-(4-trifluoromethyl-phenyl)-urea | 1.03 | 5.41 | 0.44 |
| 23 | N-[2,4-Difluoro-3-(7-pyridin-4-yl-2,3-dihydro-pyrazolo[5,1-b]thiazol-6-yl)-phenyl]-2,5-difluoro-benzenesulfonamide | 0.29 | >10 | 0.02 |
| 24 | 3-(7-Pyridin-4-yl-2,3-dihydro-pyrazolo[5,1-b]thiazol-6-yl)-N-(4-trifluoromethyl-phenyl)-benzamide | 1.23 | 5.09 | 1.46 |

From all of the above, the novel compounds of formula (I) of the invention appear to be particularly advantageous in the therapy of diseases caused by deregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
|---|---|
| g (grams) | mg (milligrams) |
| ml (milliliters) | mM (millimolar) |
| μM (micromolar) | mmol (millimoles) |
| h (hours) | MHz (Mega-Hertz) |
| mm (millimetres) | Hz (Hertz) |
| M (molar) | min (minutes) |
| mol (moles) | TLC |
| r.t. (room temperature) | (thin layer chromatography) |
| TFA (trifluoroacetic acid) | TEA (triethylamine) |
| DIPEA | DMF |
| (N,N-diisopropyl-N-ethylamine) | (N,N-dimethyl formamide) |
| THF (tetrahydrofuran) | DCM (dichloromethane) |
| MeOH (Methanol) | Hex (hexane) |
| TIPS (triisopropylsilyl) | DMSO (dimethylsulfoxide) |
| TBDMS (dimethyl-tert-butylsilyl) | bs (broad singlet) |
| BOC (tert-butyloxycarbonyl) | Ac (acetyl) |
| NaH = sodium hydride, | Ac$_2$O acetic anhydride |
| 60% in mineral oil | ESI = |
| TBTU (2-(1H-benzotriazol-1-yl)-1,1,3,3-tetramethyluronium tetrafluoroborate | electrospray ionization |
| RP-HPLC (reverse phase high performance liquid chromatography) | |

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, $CH_2Cl_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

Preparation of 2-(3-bromo-phenyl)-3-pyridin-4-yl-6,7-dihydro-5H-pyrazolo[5,1-b][1,3]thiazine [(II)3, X=CH, R', R2, R3, R4, R5=H, W=(CH$_2$)$_3$]

Method A

Step e 1-(3-bromophenyl)-2-pyridin-4-ylethanone

To 66 ml (0.066 mol) of sodium hexamethyldisilazane 1M in tetrahydrofuran under nitrogen atmosphere and 0° C., 3.2 ml (0.033 mol) of 4-picoline were added. After 60 minutes of stirring 5 ml (7.15 g; 0.03 mol) of ethyl 3-bromo benzoate were added and the mixture maintained in the same conditions for 1.5 hours. HCl 2N was then added, the mixture made basic with NaOH 2N and extracted with ethylacetate. The organic phase was dried over $Na_2SO_4$ and the solvent evaporated. 7.5 g (82% yield) of the title compound crystallized from AcOEt-Et$_2$O.

HPLC (254 nm): R$_t$: 4.79 min.

¹H NMR (401 MHz, DMSO-d6) δ=8.52 (d, J=6.0 Hz, 2 H), 8.19 (t, J=1.7 Hz, 1 H), 8.05 (ddd, J=1.0, 1.6, 7.8 Hz, 1H), 7.89 (ddd, J=1.0, 2.0, 8.0 Hz, 1 H), 7.54 (t, J=7.9 Hz, 1 H), 7.19-7.33 (m, 2 H), 4.53 (s, 2H).

HRMS (ESI) calcd for C13H11 BrNO [M+H]⁺ 276.0019, found 276.0023.

Step f 1-(3-bromo-phenyl)-2-[1,3]dithietan-2-ylidene-2-pyridin-4-yl-ethanone 1-(3-Bromo-phenyl)-2-pyridin-4-yl-ethanone (150 mg, 0.54 mmol), dibromomethane (114 ul, 1.62 mmol) and carbon disulfide (77 ul, 1.62 mmol) were reacted at room temperature in dry DMSO in the presence of K2CO3 (225 mg, 1.62 mmol) for three hours. The reaction, evaporated to dryness, was worked up with water and ethyl acetate. The pooled organic extracts were washed with brine, dried over sodium sulphate and evaporated down. The crude material was purified by a quick elution with ethyl acetate through a pad of silica to give the clean product in 74% yield.

HPLC (254 nm): R_t: 5.42 min.

¹H NMR (401 MHz, DMSO-d6) δ=8.47-8.51 (m, 2 H), 7.58 (ddd, J=1.3, 1.8, 7.8 Hz, 1 H), 7.41 (t, J=1.7 Hz, 1 H), 7.21 (t, J=7.8 Hz, 1 H), 7.15 (dt, J=1.3, 7.7 Hz, 1 H), 7.08-7.13 (m, 2 H), 4.35 (s, 2 H).

HRMS (ESI) calcd for C15H11BrNOS2 [M+H]⁺ 363.9460, found 363.9471.

Step g 5-(3-bromo-phenyl)-4-pyridin-4-yl-2H-pyrazole-3-thiol 1-(3-Bromo-phenyl)-2-[1,3]dithietan-2-ylidene-2-pyridin-4-yl-ethanone (150 mg, 0.41 mmol) was refluxed in 4 ml of THF in the presence of 1 ml of 1M NH2NH2 in THF to form the thiopyrazole intermediate. The reaction was evaporated to dryness, diluted with a small amount of absolute ethanol from which the product was precipitated with THF. The crude compound was isolated by filtration and submitted to the next step without purification.

¹H NMR (401 MHz, DMSO-d₆) δ=13.97 (br s, 1 H), 10.18 (br s, 1 H), 8.42 (d, J=4.02 Hz, 2 H), 7.53 (d, J=7.80 Hz, 1H), 7.51 (br. s, 1 H), 7.31 (t, J=7.86 Hz, 1 H), 7.22 (d, J=7.68 Hz, 1 H), 7.02 (br. s, 2 H).

Method B

Step a 2-(3-bromo-phenyl)-3-pyridin-4-yl-6,7-dihydro-5H-pyrazolo[5,1-b][1,3]thiazine 5-(3-Bromo-phenyl)-4-pyridin-4-yl-2H-pyrazole-3-thiol (60 mg, 0.22 mmol), 1,3-dibromopropane (22 ul, 0.22 mmol), K₂CO₃ (152 mg, 1.1 mmol) and dry DMF (5 ml) were reacted at room temperature for 16 hours. Water was added and the reaction extracted with ethyl acetate. The pooled organic extracts were washed with brine, dried over sodium sulphate and evaporated down. The crude material was purified by flash column chromatography eluting with ethyl acetate:hexane (1:1) to give a white solid (50% yield over two steps).

HPLC (254 nm): R_t: 5.65 min.

¹H NMR (401 MHz, DMSO-d₆) δ=8.53 (d, J=4.63 Hz, 2 H), 7.53 (m, 2 H), 7.30 (t, J=7.80 Hz, 1 H), 7.28 (m, 1 H), 7.14 (m, 2 H), 4.29 (t, J=5.91 Hz, 2 H), 3.17-3.22 (m, 2 2 H), 2.34-2.40 (m, 2 H).

HRMS (ESI) calcd for C17H15BrN3S [M+H]⁺ 372.0165, found 372.0179.

Prepararion of 6-(3-bromo-phenyl)-7-pyridin-4-yl-2,3-dihydro-pyrazolo[5,1-b]thiazole [(II)3, X=CH, R', R2, R3, R4, R5 =H, W=(CH₂)₂]

5-(3-Bromo-phenyl)-4-pyridin-4-yl-2H-pyrazole-3-thiol (prepared as described above) (60 mg, 0.22 mmol), 1,2-dibromoethane (19 ul, 0.22 mmol), K₂CO₃ (152 mg, 1.1 mmol) and dry DMF (5 ml) were reacted at room temperature for 16 hours. Water was added and the reaction extracted with ethyl acetate. The pooled organic extracts were washed with brine, dried over sodium sulphate and evaporated down. The crude material was purified by flash column chromatography eluting with ethyl acetate:hexane (1:1) to give a white solid (50% yield over two steps).

HPLC (254 nm): R_t: 5.40 min.

¹H NMR (401 MHz, DMSO-d₆) δ=8.48-8.52 (m, 2 H), 7.59 (m, 2 H), 7.36 (m, 2 H) 7.08 (m, 2 H), 4.47 (t, J=7.56 Hz, 2 H), 4.01 (t, J=7.56 Hz, 2 H).

HRMS (ESI) calcd for C16H12BrN3S [M+H]⁺ 358.0008, found 358.0016.

Preparation of 2-(3-bromo-phenyl)-3-pyridin-4-yl-5,6,7,8-tetrahydro-4-thia-1,8a-diaza-azulene [(II)3, X=CH, R', R2, R3, R4, R5=H, W=(CH₂)₄]

5-(3-Bromo-phenyl)-4-pyridin-4-yl-2H-pyrazole-3-thiol (prepared as described above) (60 mg, 0.22 mmol), 1,4-dibromobutane (32 ul, 0.22 mmol), K₂CO₃ (152 mg, 1.1 mmol) and dry DMF (5 ml) were reacted at room temperature for 16 hours. Water was added and the reaction extracted with ethyl acetate. The pooled organic extracts were washed with brine, dried over sodium sulphate and evaporated down. The crude material was purified by flash column chromatography eluting with ethyl acetate:hexane (1:1) to give a white solid (50% yield over two steps).

HPLC (254 nm): R_t: 7.22 min.

¹H NMR (401 MHz, DMSO-d₆) δ=8.56 (d, J=5.97 Hz, 2 H), 7.52 (br. s, 1H), 7.50 (br.s, 1H), 7.28 (br. m, 1H), 7.26 (br. m, 1H), 7.19 (m, 2H), 4.50-4.54 (m, 2 H), 2.75-2.79 (m, 2 H), 2.05-2.13 (m, 2 H), 1.75-1.84 (m, 2 H).

HRMS (ESI) calcd for C18H16BrN3S [M+H]⁺ 386.0321, found 386.0338.

Example 1

Preparation of 1-[3-(7-pyridin-4-yl-2,3-dihydro-pyrazolo[5,1-b]thiazol-6-yl)-phenyl]-3-(4-trifluoromethyl-phenyl)urea [(I)C, X=CH, R', R2, R3, R4, R5, Y=H, W=CH₂CH₂, R6=4-trifluoromethylphenyl] (Cpd. no 5)

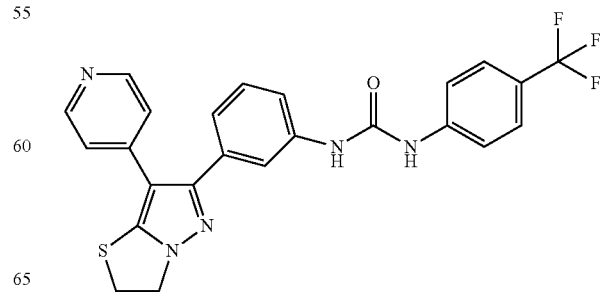

Method A
Step a

[hydroxy-(3-nitro-phenyl)-methyl]-phosphonic acid dimethyl ester

3-Nitrobenzaldehyde (20 g, 0.132 mol) was dissolved in 100 mL of ethyl acetate. Triethylamine (22 mL, 0.158 mol, 1.2 eq) was added, followed by dimethylphosphite (15.7 mL, 0.171 mmol, 1.3 eq) and the mixture was stirred at room temperature. After 2 hours the mixture was diluted with 150 mL of ethyl acetate and washed with saturated aqueous ammonium chloride (2×50 mL) and water (50 mL). The organic layer was dried over $Na_2SO_4$ and concentrated under reduced pressure. The residue was treated with ethyl ether to obtain a beige solid, which was filtered and dried under vacuum at 40° C. for 1 h (26.7 g, 77% yield).

HPLC (254 nm): $R_t$: 3.15 min.

$^1$H NMR (401 MHz, DMSO-$d_6$) δ=8.30 (q, J=1.8 Hz, 1 H), 8.14-8.20 (m, 1 H), 7.89 (d, J=7.6 Hz, 1 H), 7.68 (t, J=7.6 Hz, 1 H), 6.62 (dd, J=5.9, 14.1 Hz, 1 H), 5.30 (dd, J=5.9, 14.0 Hz, 1 H), 3.67 (d, J=7.4 Hz, 3 H), 3.64 (d, J=7.4 Hz, 3 H).

HRMS (ESI) calcd for C9H12NO6P [M+H]$^+$ 262.0475, found 262.0478.

Step b

[(3-nitro-phenyl)-(tetrahydro-pyran-2-yloxy)-methyl]-phosphonic acid dimethyl ester

[Hydroxy-(3-nitro-phenyl)-methyl]-phosphonic acid dimethyl ester (26.7 g, 0.102 mol) was suspended in dry toluene (340 mL) under nitrogen atmosphere. 3,4-Dihydro-2H-pyrane (20.6 mL, 0.228 mol, 2.2 eq) was added, followed by p-toluensulfonic acid (590 mg, 0.003 mol, 0.03 eq) and the mixture was stirred at 60° C. for 1 h. the reaction mixture was then concentrated under reduced pressure, taken up with ethyl acetate (300 mL) and washed with saturated aqueous $NaHCO_3$ and water. The organic layer was dried over $Na_2SO_4$ and concentrated to dryness. The desired product was obtained in quantitative yield as a yellow solid (mixture of 2 diastereoisomers).

HPLC (254 nm): $R_t$: 4.88 min.

$^1$H NMR (401 MHz, DMSO-$d_6$)(major diastereoisomer) δ=8.25 (q, J=2.2 Hz, 1 H), 8.23 (dt, J=2.5, 8.2 Hz, 1 H), 7.88 (d, J=8.3 Hz, 1 H), 7.70 (t, J=7.9 Hz, 1 H), 5.38 (d, J=17.3 Hz, 1 H), 4.43 (t, J=2.7 Hz, 1 H), 3.85-3.97 (m, 1 H), 3.73 (d, J=10.5 Hz, 3 H), 3.65 (d, J=10.5 Hz, 3 H), 3.48-3.56 (m, 1 H), 1.49-1.82 (3 m, 6 H).

HRMS (ESI) calcd for C14H20NO7P [M+H]$^+$ 346.105, found 346.1043.

Step c

4-[2-(3-nitro-phenyl)-2-(tetrahydro-pyran-2-yloxy)-vinyl]-pyridine

[(3-Nitro-phenyl)-(tetrahydro-pyran-2-yloxy)-methyl]-phosphonic acid dimethyl ester (40.7 g, 0.105 mol) was dissolved in dry THF (1 L) under nitrogen. Sodium hydride (60% suspension in mineral oil)(6.3 g, 0.158 mol, 1.5 eq) was added and the mixture was stirred for 10 minutes at room temperature. Neat 4-picolinaldehyde (10 mL, 0.105 mol, 1 eq) was then added dropwise and the mixture was heated to 60° C. and stirred at this temperature for 2.5 hours. The reaction mixture was concentrated under reduced pressure to ⅓ of the original volume and then diluted with water (500 mL). pH was adjusted to 7-8 by adding a saturated solution of $NaHCO_3$ and the mixture was extracted with ethyl acetate (4×300 mL). The organic layer was dried over $Na_2SO_4$ and concentrated to dryness. An oil (37.7 g) was obtained, which was used without further purification in the following step.

Step d 1-(3-nitro-phenyl)-2-pyridin-4-yl-ethanone

The oil obtained in the previous step was dissolved in methanol (570 mL). 1N HCl (57 mL) was added and the mixture was stirred at 50° C. for 2 hours. The mixture was then concentrated under reduced pressure and diluted with water (200 mL). pH was adjusted to 7-8 by addition of $NaHCO_3$. The precipitated product was collected by filtration, washed with water and dried under vacuum at 60° C. for 1 h obtaining 23.7 g of brown solid. The solid was purified by flash chromatography on silica gel (ethyl acetate) and then treated with ethyl ether to obtain an off-white solid, which was dried under vacuum at 40° C. for 1 h (15 g, 59% yield over three steps).

HPLC (254 nm): $R_t$: 4.29 min.

$^1$H NMR (401 MHz, DMSO-$d_6$) δ=8.74 (t, J=1.8 Hz, 1 H), 8.52-8.55 (m, 2 H), 8.52 (m, 1 H), 8.49 (m, 1 H), 7.89 (t, J=7.8 Hz, 1 H), 7.30-7.34 (m, 2 H), 4.63 (s, 2 H).

HRMS (ESI) calcd for C13H10N2O3 [M+H]$^+$ 243.0764, found 243.0772.

Step f

2-[1,3]-dithietan-2-ylidene-1-(3-nitro-phenyl)-2-pyridin-4-yl-ethanone

To a solution of 1-(3-nitro-phenyl)-2-pyridin-4-yl-ethanone (5 g, 20.64 mmol) in dry DMSO (80 mL) under nitrogen atmosphere solid potassium carbonate (8.56 g, 61.92 mmol, 3 eq) was added at room temperature, followed by carbon disulfide (3.73 mL, 61.92 mmol, 3 eq) and dibromomethane (4.35 mL, 61.92 mmol, 3 eq). The reaction mixture was stirred at room temperature for 1 hour and then poured into stirred iced water (600 mL). The orange precipitate was filtered, washed with water and dried at 60° C. under reduced pressure for 1 hour. The crude product was purified by silica gel chromatography (SP1, eluant: n-hexane/ethyl acetate 2:8) to obtain 5.2 g of yellow solid (76%).

HPLC (254 nm): $R_t$: 4.93 min.

$^1$H NMR (401 MHz, DMSO-d6) δ=8.49-8.52 (m, 2 H), 8.23 (ddd, J=1.2, 2.4, 8.0 Hz, 1 H), 8.04 (t, J=1.8 Hz, 1 H), 7.60-7.64 (m, 1 H), 7.52-7.59 (m, 1 H), 7.15-7.17 (m, 2 H), 4.39 (s, 2 H).

HRMS (ESI) calcd for C15H11N2O3S2 [M+H]$^+$ 331.0206, found 331.0203.

Step g 5-(3-nitro-phenyl)-4-pyridin-4-yl-2H-pyrazole-3-thiol

2-[1,3]-Dithietan-2-ylidene-1-(3-nitro-phenyl)-2-pyridin-4-yl-ethanone (5.2 g, 15.7 mmol) was suspended in absolute ethanol (60 mL) and heated to 60° C. Hydrazine monohydrate (3.05 mL, 63 mmol, 4 eq) was added dropwise and the mixture was stirred at 60° C. for 2 hours. The suspension was concentrated to about ¼ of the original volume, diluted with THF (30 mL) and stirred for 5 minutes. The solid was filtered, washed with THF and dried at 50° C. for 2 hours. 3.92 g of 5-(3-nitro-phenyl)-4-pyridin-4-yl-2H-pyrazole-3-thiol were obtained as an orange solid (84%).

MS (ESI): 299 [M+H]$^+$.

Method B
Step a

6-(3-nitro-phenyl)-7-pyridin-4-yl-2,3-dihydro-pyrazolo[5,1-b]thiazole 5-(3-Nitro-phenyl)-4-pyridin-4-yl-2H-pyrazole-3-thiol (298 mg, 1.0 mmol) was dissolved in dry DMF (12.5 mL) under nitrogen atmosphere. Solid potassium carbonate (690 mg, 5 mmol, 5 eq) was added followed by 1,2-dibromoethane (0.086 mL, 1 mmol, 1 eq) and the suspension was stirred at room temperature for 3 hours. The reaction mixture was then diluted with ethyl acetate (60 mL) and washed with saturated aqueous NaHCO$_3$ and brine. The organic layer was dried over Na$_2$SO$_4$ and concentrated under reduced pressure. 280 mg of 6-(3-nitro-phenyl)-7-pyridin-4-yl-2,3-dihydro-pyrazolo[5,1-b]thiazole were obtained as an off-white solid (87%).

MS (ESI): 325 [M+H]$^+$.

Method E
Step a

3-(7-pyridin-4-yl-2,3-dihydro-pyrazolo[5,1-b]thiazol-6-yl)-phenylamine 6-(3-Nitro-phenyl)-7-pyridin-4-yl-2,3-dihydro-pyrazolo[5,1-b]thiazole (150 mg, 0.463 mmol) was suspended in a 5:1 dioxane/water mixture (3 mL). Zinc powder (121 mg, 1.852 mmol, 4 eq) was added, followed by ammonium chloride (247 mg, 4.63 mmol, 10 eq) and the mixture was heated to 100° C. and stirred at the same temperature for 2 hours. The reaction mixture was then allowed to cool to room temperature and diluted with water and ethyl acetate. The aqueous phase was basified by adding solid Na$_2$HPO$_4$ and extracted with ethyl acetate (3×20 mL). The combined organic layers were washed with saturated aqueous NaHCO$_3$ and brine, dried and concentrated to dryness. 100 mg of 3-(7-pyridin-4-yl-2,3-dihydro-pyrazolo[5,1-b]thiazol-6-yl)-phenylamine were obtained as off-white solid (73%).

HPLC (254 nm): R$_t$: 4.55 min.

$^1$H NMR (401 MHz, DMSO-d$_6$) δ=8.46 (dd, J=1.6, 4.6 Hz, 2 H), 7.06-7.12 (m, 2 H), 7.02 (t, J=7.7 Hz, 1 H), 6.66 (t, J=1.8 Hz, 1 H), 6.58 (ddd, J=0.9, 2.3, 8.0 Hz, 1 H), 6.48 (ddd, J=1.0, 1.2, 7.8 Hz, 1 H), 5.19 (br. s., 2 H), 4.44 (t, J=7.6 Hz, 2 H), 4.00 (t, J=7.6 Hz, 2 H).

HRMS (ESI) calcd for C16H15N4S [M+H]$^+$ 295.1012, found 295.1010.

Step e

1-[3-(7-pyridin-4-yl-2,3-dihydro-pyrazolo[5,1-b]thiazol-6-yl)-phenyl]-3-(4-trifluoromethyl-phenyl)-urea (Cpd. no 5)

3-(7-Pyridin-4-yl-2,3-dihydro-pyrazolo[5,1-b]thiazol-6-yl)-phenylamine (52 mg, 0.177 mmol) was dissolved in dry DCM under nitrogen atmosphere. p-trifluoromethyl-phenyl-isocyanate (0.030 mL, 0.212 mmol, 1.2 eq) was added and the mixture was stirred at room temperature for 1 hour and then concentrated under reduced pressure. The crude product was purified by silica gel chromatography (eluant: DCM/MeOH 96:4) to give 73 mg (86%) of 1-[3-(7-pyridin-4-yl-2,3-dihydro-pyrazolo[5,1-b]thiazol-6-yl)-phenyl]-3-(4-trifluoromethyl-phenyl)-urea as white powder.

HPLC (254 nm): R$_t$: 6.52 min.

$^1$H NMR (401 MHz, DMSO-d$_6$) δ=9.05 (s, 1 H), 8.86 (s, 1 H), 8.43-8.51 (m, 2 H), 7.63 (m, 4 H), 7.57 (t, J=1.7 Hz, 1 H), 7.48-7.52 (m, 1 H), 7.31 (t, J=7.9 Hz, 1 H), 7.06-7.11 (m, 2 H), 6.98-7.02 (m, 1 H), 4.47 (t, J=7.5 Hz, 2 H), 4.01 (t, J=7.6 Hz, 2 H).

HRMS (ESI) calcd for C24H19F3N5OS [M+H]$^+$ 482.1257, found 482.1257.

Operating in an analogous way the following compounds were obtained:

1-(4-chloro-phenyl)-3-[3-(7-pyridin-4-yl-2,3-dihydro-pyrazolo[5,1-b]thiazol-6-yl)-phenyl]-urea [(I)C, X═CH, R', R2, R3, R4, R5, Y═H, W═CH$_2$CH$_2$, R6=4-chlorophenyl] (Cpd. no 6)

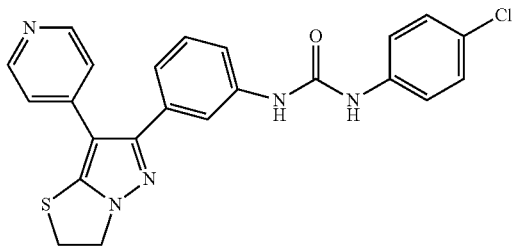 [SMILES: O=C(Nc1ccc(Cl)cc1)Nc1cccc(-c2nn3c(c2-c2ccncc2)SCC3)c1]

HPLC (254 nm): R$_t$: 6.22 min.

$^1$H NMR (401 MHz, DMSO-d$_6$) δ=8.76 (s, 2 H), 8.47-8.51 (m, 2 H), 7.55 (t, J=1.8 Hz, 1 H), 7.44-7.52 (m, 3 H), 7.28-7.35 (m, 3 H), 7.07-7.12 (m, 2 H), 6.99 (dt, J=1.1, 7.6 Hz, 1 H), 4.48 (t, J=7.6 Hz, 2 H), 4.02 (t, J=7.6 Hz, 2 H)

HRMS (ESI) calcd for C23H19ClN5OS [M+H]$^+$ 448.0994, found 448.0999.

1-(4-chloro-3-trifluoromethyl-phenyl)-3-[3-(7-pyridin-4-yl-2,3-dihydro-pyrazolo[5,1-b]thiazol-6-yl)-phenyl]urea [(I)C, X═CH, R', R2, R3, R4, R5, Y═H, W═CH$_2$CH$_2$, R6=4-chloro-3-trifluoromethyl-phenyl]

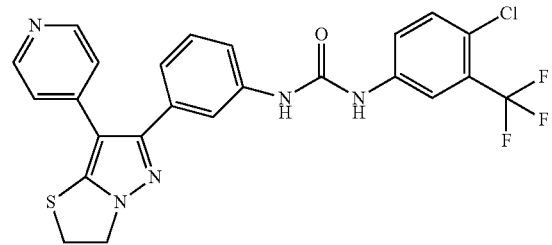 [SMILES: O=C(Nc1cccc(-c2nn3c(c2-c2ccncc2)SCC3)c1)Nc1ccc(Cl)c(C(F)(F)F)c1]

HPLC (254 nm): R$_t$: 6.84 min.

$^1$H NMR (401 MHz, DMSO-d$_6$) δ=9.11 (s, 1 H), 8.90 (s, 1 H), 8.45-8.53 (m, 2 H), 8.09 (d, J=1.3 Hz, 1 H), 7.60-7.63 (m, 2 H), 7.59 (t, J=1.83 Hz, 1 H), 7.48-7.52 (m, 1 H), 7.32 (t, J=7.9 Hz, 1 H), 7.06-7.13 (m, 2 H), 7.01 (ddd, J=1.0, 1.2, 7.8 Hz, 1 H), 4.48 (t, J=7.6 Hz, 2 H), 4.01 (t, J=7.6 Hz, 2 H).

HRMS (ESI) calcd for C24H18ClF3N5OS [M+H]$^+$ 516.0867, found 516.0864.

1-(4-tert-butyl-phenyl)-3-[3-(7-pyridin-4-yl-2,3-di-hydro-pyrazolo[5,1-b]thiazol-6-yl)-phenyl]-urea [(I) C, X=CH, R', R2, R3, R4, R5, Y=H, W=CH$_2$CH$_2$, R6=4-tert-butyl-phenyl] (Cpd. no 18)

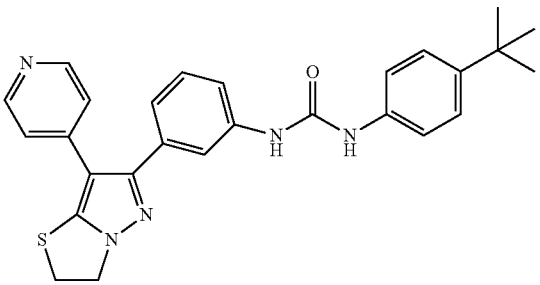 [SMILES: CC(C)(C)c1ccc(NC(=O)Nc2cccc(-c3nn4c(c3-c3ccncc3)SCC4)c2)cc1]

HPLC (254 nm): R$_t$: 6.88 min.
$^1$H NMR (401 MHz, DMSO-d$_6$) δ=8.66 (s, 1 H), 8.51 (s, 1 H), 8.45-8.48 (m, 2 H), 7.54 (t, J=1.8 Hz, 1 H), 7.45-7.50 (m, 1 H), 7.25-7.36 (m, 5 H), 7.06-7.10 (m, 2 H), 6.95 (ddd, J=1.1, 1.3, 7.8 Hz, 1 H), 4.47 (t, J=7.6 Hz, 2 H), 4.00 (t, J=7.6 Hz, 2 H), 1.26 (s, 9 H).
HRMS (ESI) calcd for C27H28N5OS [M+H]$^+$ 470.2009, found 470.2015.

Example 2

Preparation of 3-fluoro-N-[3-(7-pyridin-4-yl-2,3-dihydro-pyrazolo[5,1-b]thiazol-6-yl)-phenyl]-benzenesulfonamide [(I)A, X=CH, R', R2, R3, R4, R5=H, W=CH$_2$CH$_2$, R6=3-fluorophenyl]

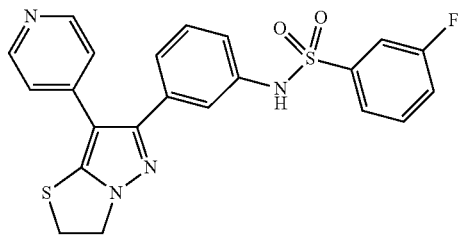 [SMILES: O=S(=O)(Nc1cccc(-c2nn3c(c2-c2ccncc2)SCC3)c1)c1cccc(F)c1]

Method E
Step c 3-(7-Pyridin-4-yl-2,3-dihydro-pyrazolo[5,1-b]thiazol-6-yl)-phenylamine (prepared as described in Example 1) (30 mg, 0.102 mmol) was dissolved in dry DCM (1 mL). At room temperature 3-fluorobenzensulfonylchloride (0.014 mL, 0.107 mmol, 1.05 eq) was added followed by NMM (0.012 mL, 0.107 mmol, 1.05 eq) and the mixture was stirred for 1 hour. It was then diluted with DCM and washed with water and brine. The organic layer was dried over Na$_2$SO$_4$ and concentrated under reduced pressure. The crude product was purified by chromatography on silica gel (eluant DCM/MeOH 96:4) to give 27 mg of 3-fluoro-N-[3-(7-pyridin-4-yl-2,3-dihydro-pyrazolo[5,1-b]thiazol-6-yl)-phenyl]-benzenesulfonamide.
HPLC (254 nm): R$_t$: 5.77 min.
$^1$H NMR (401 MHz, DMSO-d$_6$) δ=10.45 (s, 1 H), 8.41-8.46 (m, 2 H), 7.62 (td, J=8.1, 5.5 Hz 1 H), 7.44-7.56 (m, 3 H), 7.26-7.31 (m, 1 H), 7.15-7.18 (m, 1 H), 7.13-7.18 (m, 1 H), 7.08 (dt, J=1.3, 7.7 Hz, 1 H), 6.94-6.98 (m, 2H), 4.45 (t, J=7.6 Hz, 2 H), 3.99 (t, J=7.6 Hz, 2 H).
HRMS (ESI) calcd for C22H18FN4O2S2 [M+H]$^+$ 453.0850, found 453.0851.
Operating in an analogous way the following sulfonamides were obtained:

2,5-difluoro-N-[3-(7-pyridin-4-yl-2,3-dihydro-pyrazolo[5,1-b]thiazol-6-yl)-phenyl]-benzenesulfonamide [(I)A, X=CH, R', R2, R3, R4, R5=H, W=CH2CH2, R6=2,5-difluoro-phenyl] (Cpd no 11)

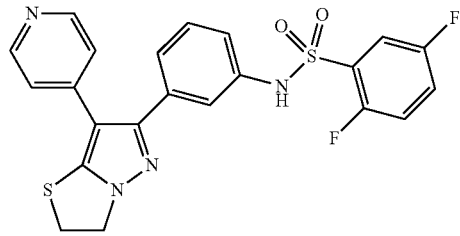 [SMILES: O=S(=O)(Nc1cccc(-c2nn3c(c2-c2ccncc2)SCC3)c1)c1cc(F)ccc1F]

HPLC (254 nm): R$_t$: 5.81 min.
$^1$H NMR (401 MHz, DMSO-d$_6$) δ=10.82 (s, 1 H), 8.42-8.46 (m, 2 H), 7.46-7.62 (m, 3 H), 7.26-7.32 (m, 1 H), 7.13-7.19 (m, 2 H), 7.09 (dt, J=1.3, 7.7 Hz, 1 H), 6.93-6.97 (m, 2 H), 4.45 (t, J=7.6 Hz, 2 H), 4.00 (t, J=7.6 Hz, 2 H).
HRMS (ESI) calcd for C22H17F2N4O2S2 [M+H]$^+$ 471.0756, found 471.0755.

Example 3

Preparation of 1-(4-chloro-3-trifluoromethyl-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH$_2$)$_3$, R6=4-chloro-3-trifluoromethyl-phenyl]

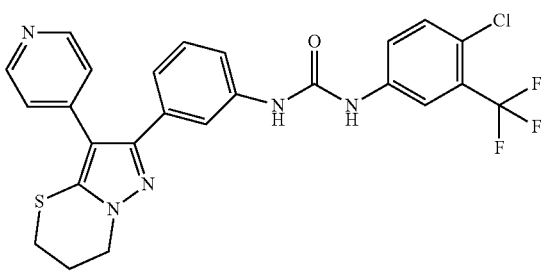 [SMILES: O=C(Nc1cccc(-c2nn3c(c2-c2ccncc2)SCCC3)c1)Nc1ccc(Cl)c(C(F)(F)F)c1]

Method B
Step a 2-(3-nitro-phenyl)-3-pyridin-4-yl-6,7-dihydro-5H-pyrazolo[5,1-b][1,3]thiazine 2-(3-Nitro-phenyl)-3-pyridin-4-yl-6,7-dihydro-5H-pyrazolo[5,1-b][1,3]thiazine was prepared as described in Example 1 (Method B, step a), using 1,3-dibromopropane instead of 1,2-dibromoethane.
HPLC (254 nm): R$_t$: 5.17 min.
$^1$H NMR (401 MHz, DMSO-d$_6$) δ=8.51-8.59 (m, 2 H), 8.15-8.23 (m, 2 H), 7.74 (dt, J=1.3, 7.8 Hz, 1 H), 7.60-7.67 (m, 1 H), 7.14-7.21 (m, 2 H), 4.34 (t, J=5.9 Hz, 2 H), 3.20-3.25 (m, 2 H), 2.40 (t, J=4.8 Hz, 2 H).
HRMS (ESI) calcd for C17H15N4O2S [M+H]$^+$ 339.091, found 339.0903.

Method E
Step a

3-(3-pyridin-4-yl-6,7-dihydro-5H-pyrazolo[5,1-b][1,3]thiazin-2-yl)-phenylamine 3-(3-Pyridin-4-yl-6,7-dihydro-5H-pyrazolo[5,1-b][1,3]thiazin-2-yl)-phenylamine was obtained by reduction of 2-(3-nitro-phenyl)-3-pyridin-4-yl-6,7-dihydro-5H-pyrazolo-[5,1-b][1,3]thiazine following the same procedure described in Example 1 (Method D, Step a).

HPLC (254 nm): $R_t$: 3.92 min.

$^1$H NMR (401 MHz, DMSO-$d_6$) δ=8.44-8.52 (m, 2 H), 7.06-7.16 (m, 2 H), 6.94 (t, J=7.8 Hz, 1 H), 6.65 (t, J=1.8 Hz, 1 H), 6.52 (ddd, J=0.9, 2.3, 8.0 Hz, 1 H), 6.38 (ddd, J=1.0, 1.2, 7.7 Hz, 1 H), 5.07 (s, 2 H), 4.26 (t, J=6.0 Hz, 2H), 3.11-3.23 (m, 2 H), 2.28-2.45 (m, 2 H).

HRMS (ESI) calcd for C17H17N4S [M+H]$^+$ 309.1169, found 309.1156.

Method E
Step e

1-(4-chloro-3-trifluoromethyl-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH$_2$)$_3$, R6=4-chloro-3-trifluoromethyl-phenyl]

3-(3-Pyridin-4-yl-6,7-dihydro-5H-pyrazolo[5,1-b][1,3]thiazin-2-yl)-phenylamine (50 mg, 0.162 mmol) was dissolved in dry DCM under nitrogen atmosphere. 4-chloro-3-trifluoromethylphenylisocyanate (43 mg, 0.195 mmol, 1.2 eq) was added, the mixture was stirred at room temperature for 2 hours and then concentrated under reduced pressure. The crude product was purified by silica gel chromatography (eluant: 100% ethyl acetate) to give 64 mg (75%) of 1-(4-chloro-3-trifluoromethyl-phenyl)-3-[3-(3-pyridin-4-yl-6,7-dihydro-5H-pyrazolo[5,1-b][1,3]thiazin-2-yl)-phenyl]-urea as white powder.

HPLC (254 nm): $R_t$: 6.28 min.

$^1$H NMR (401 MHz, DMSO-$d_6$) δ=9.07 (s, 1 H), 8.85 (s, 1 H), 8.48-8.52 (m, 2 H), 8.08 (s, 1 H), 7.60 (s, 2 H), 7.54 (d, J=1.5 Hz, 1 H), 7.42-7.47 (m, 1 H), 7.24 (t, J=7.9 Hz, 1 H), 7.09-7.16 (m, 2 H), 6.90 (dd, J=0.9, 7.6 Hz, 1 H), 4.29 (t, J=5.9 Hz, 2 H), 3.15-3.23 (m, 2 H), 2.33-2.43 (m, 2 H).

HRMS (ESI) calcd for C25H20ClF3N5OS [M+H]$^+$ 530.1024, found 530.1016.

Operating in an analogous way the following ureas were obtained:

1-[3-(3-pyridin-4-yl-6,7-dihydro-5H-pyrazolo[5,1-b][1,3]thiazin-2-yl)-phenyl]-3-m-tolyl-urea [(I)C, X=CH, R', R2, R3, R4, R5, Y=H, W=(CH$_2$)$_3$, R6=3-methyl-phenyl]

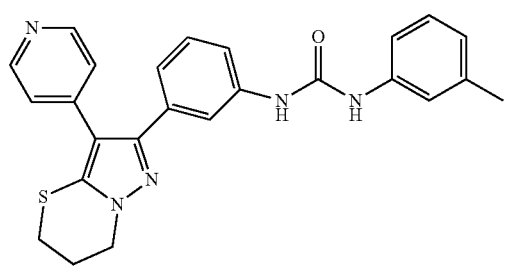 [SMILES: Cc1cccc(NC(=O)Nc2cccc(-c3nn4c(c3-c3ccncc3)SCCC4)c2)c1]

HPLC (254 nm): $R_t$: 5.47 min.

$^1$H NMR (401 MHz, DMSO-$d_6$) δ=8.64 (s, 1 H), 8.49-8.52 (m, 3 H), 7.52 (d, J=1.6 Hz, 1 H), 7.43 (dt, J=1.0, 8.2 Hz, 1 H), 7.27 (s, 1 H), 7.13-7.25 (m, 3 H), 7.11-7.14 (m, 2 H), 6.85 (dd, J=1.0, 7.6 Hz, 1 H), 6.78 (d, J=7.3 Hz, 1H), 4.29 (t, J=5.9 Hz, 2 H), 3.17-3.24 (m, 2 H), 2.33-2.42 (m, 2 H), 2.27 (s, 3 H).

HRMS (ESI) calcd for C25H24N5OS [M+H]$^+$ 442.1696, found 442.1700.

1-(4-chloro-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH$_2$)$_3$, R6=4-chlorophenyl] (Cpd. no 1)

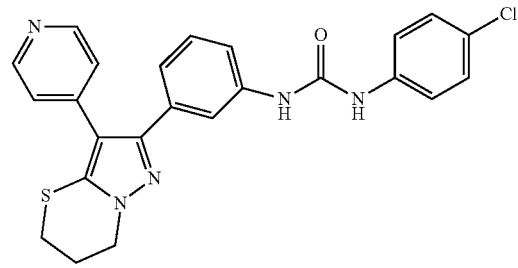 [SMILES: O=C(Nc1ccc(Cl)cc1)Nc1cccc(-c2nn3c(c2-c2ccncc2)SCCC3)c1]

HPLC (254 nm): $R_t$: 6.34 min.

$^1$H NMR (401 MHz, DMSO-$d_6$) δ=8.73 (s, 1 H), 8.71 (s, 1 H), 8.48-8.54 (m, 2 H), 7.51 (t, J=1.8 Hz, 1 H), 7.46 (d, J=8.9 Hz, 2 H), 7.42-7.47 (m, 1 H), 7.32 (d, J=8.9 Hz, 2 H), 7.23 (t, J=7.9 Hz, 1 H), 7.10-7.16 (m, 2 H), 6.88 (ddd, J=1.1, 1.2, 7.8 Hz, 1 H), 4.30 (t, J=5.9 Hz, 2 H), 3.17-3.24 (m, 2 H), 2.34-2.43 (m, 2 H).

HRMS (ESI) calcd for C24H21ClN5OS [M+H]$^+$ 462.1150, found 462.1137.

1-[3-(3-pyridin-4-yl-6,7-dihydro-5H-pyrazolo[5,1-b][1,3]thiazin-2-yl)-phenyl]-3-p-tolyl-urea [(I)C, X=CH, R', R2, R3, R4, R5, Y=H, W=(CH$_2$)$_3$, R6=4-methylphenyl] (Cpd. no 2)

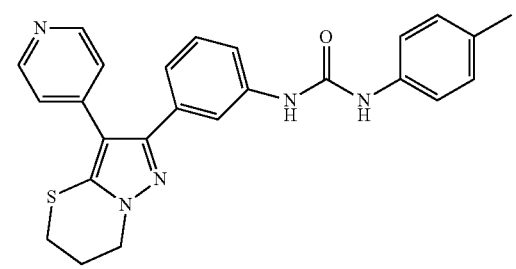 [SMILES: Cc1ccc(NC(=O)Nc2cccc(-c3nn4c(c3-c3ccncc3)SCCC4)c2)cc1]

HPLC (254 nm): $R_t$: 6.13 min.

$^1$H NMR (401 MHz, DMSO-$d_6$) δ=8.62 (s, 1 H), 8.49-8.53 (m, 2 H), 8.47 (s, 1 H), 7.49-7.53 (m, 1 H), 7.44 (ddd, J=0.9, 2.2, 8.2 Hz, 1 H), 7.28-7.34 (m, 2 H), 7.22 (t, J=7.9 Hz, 1 H), 7.12-7.15 (m, 2 H), 7.08 (d, J=8.0 Hz, 2 H), 6.86 (ddd, J=1.1, 1.3, 7.9 Hz, 1 H), 4.30 (t, J=6.0 Hz, 2 H), 3.17-3.23 (m, 2 H), 2.39 (quin, J=5.8 Hz, 2 H), 2.24 (s, 3 H).

HRMS (ESI) calcd for C25H24N5OS [M+H]$^+$ 442.1696, found 442.1683.

1-(3-fluoro-phenyl)-3-[3-(3-pyridin-4-yl-6,7-dihydro-5H-pyrazolo[5,1-[1,3]thiazin-2-yl)-phenyl]-urea [(I)C, X=CH, R', R2, R3, R4, R5, Y=H, W=(CH₂)₃, R6=3-fluorophenyl]

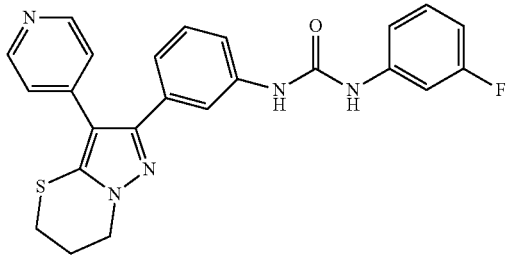 [SMILES: O=C(Nc1cccc(F)c1)Nc1cccc(-c2nn3c(c2-c2ccncc2)SCCC3)c1]

HPLC (254 nm): R$_t$: 6.09 min.
¹H NMR (401 MHz, DMSO-d₆) δ=8.82 (s, 1 H), 8.74 (s, 1 H), 8.51 (d, J=6.0 Hz, 2 H), 7.52 (t, J=1.8 Hz, 1 H), 7.42-7.49 (m, 2 H), 7.27-7.33 (m, 1 H), 7.24 (t, J=7.9 Hz, 1 H), 7.12-7.15 (m, 2 H), 7.10 (ddd, J=1.0, 1.2, 7.2 Hz, 1H), 6.89 (ddd, J=1.1, 1.3, 7.9 Hz, 1 H), 6.78 (ddd, J=0.8, 2.6, 17.0 Hz, 1 H), 4.30 (t, J=6.0 Hz, 2 H), 3.18-3.23 (m, 2 H), 2.34-2.45 (m, 2 H).
HRMS (ESI) calcd for C24H21FN5OS [M+H]⁺ 446.1446, found 446.1455.

1-[3-(3-pyridin-4-yl-6,7-dihydro-5H-pyrazolo[5,1-b][1,3]thiazin-2-yl)-phenyl]-3-(3-trifluoromethyl-phenyl)-urea [(I)C, X=CH, R', R2, R3, R4, R5, Y=H, W=(CH₂)₃, R6=3-trifluoromethylphenyl]

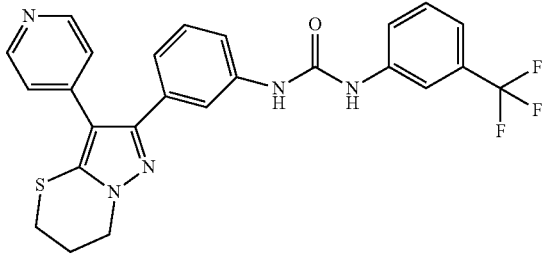 [SMILES: O=C(Nc1cccc(-c2nn3c(c2-c2ccncc2)SCCC3)c1)Nc1cccc(C(F)(F)F)c1]

HPLC (254 nm): R$_t$: 5.57 min.
¹H NMR (401 MHz, DMSO-d₆) δ=8.97 (s, 1 H), 8.81 (s, 1 H), 8.47-8.54 (m, 2 H), 8.00 (s, 1 H), 7.54-7.58 (m, 2 H), 7.51 (t, J=7.3 Hz, 1 H), 7.46 (ddd, J=1.0, 2.2, 8.2 Hz, 1 H), 7.31 (d, J=7.3 Hz, 1 H), 7.25 (t, J=7.9 Hz, 1 H), 7.12-7.16 (m, 2 H), 6.90 (ddd, J=0.8, 1.0, 7.3 Hz, 1 H), 4.30 (t, J=6.0 Hz, 2 H), 3.16-3.24 (m, 2 H), 2.34-2.45 (m, 2 H).
HRMS (ESI) calcd for C25H21F3N5OS [M+H]⁺ 496.1414, found 496.1413.

1-(4methoxy-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH₂)₃, R6=4-methoxyphenyl]

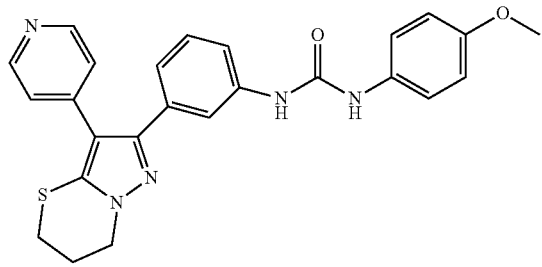

HPLC (254 nm): R$_t$: 5.72 min.
¹H NMR (401 MHz, DMSO-d₆) δ=8.58 (s, 1 H), 8.49-8.53 (m, 2 H), 8.39 (s, 1 H), 7.49-7.52 (m, 1 H), 7.44 (ddd, J=1.3, 1.6, 8.4 Hz, 1 H), 7.29-7.36 (m, 2 H), 7.22 (t, J=7.9 Hz, 1 H), 7.11-7.16 (m, 2 H), 6.80-6.91 (m, 3 H), 4.30 (t, J=5.9 Hz, 2 H), 3.72 (s, 3 H), 3.17-3.24 (m, 2 H), 2.39 (dq, J=5.7, 6.0 Hz, 2 H).
HRMS (ESI) calcd for C25H24N5O2S [M+H]⁺ 458.1645, found 458.1650.

1-(3-methoxy-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH₂)₃, R6=3-methoxyphenyl]

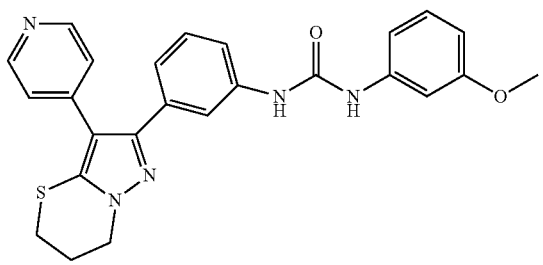 [SMILES: COc1cccc(NC(=O)Nc2cccc(-c3nn4c(c3-c3ccncc3)SCCC4)c2)c1]

HPLC (254 nm): R$_t$: 5.88 min.
¹H NMR (401 MHz, DMSO-d₆) δ=8.65 (s, 1 H), 8.59 (s, 1 H), 8.48-8.55 (m, 2 H), 7.52 (t, J=1.8 Hz, 1 H), 7.43 (ddd, J=1.0, 2.1, 8.1 Hz, 1 H), 7.23 (t, J=7.9 Hz, 1 H), 7.15-7.20 (m, 2 H), 7.12-7.15 (m, 2 H), 6.84-6.93 (m, 2H), 6.55 (dd, J=2.1, 7.9 Hz, 1 H), 4.30 (t, J=6.0 Hz, 2 H), 3.74 (s, 3 H), 3.20 (d, J=11.1 Hz, 2 H), 2.35-2.43 (m, 2H).
HRMS (ESI) calcd for C25H24N5O2S [M+H]⁺ 458.1645, found 458.1645.

1-(4-fluoro-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH₂)₃, R6=4-fluorophenyl]

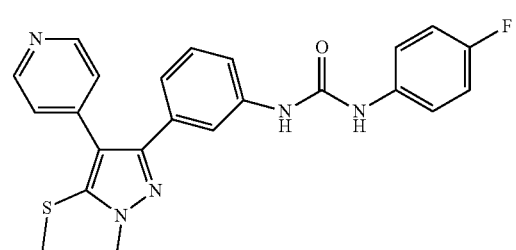

HPLC (254 nm): R$_t$: 5.91 min.
¹H NMR (401 MHz, DMSO-d₆) δ=8.67 (s, 1 H), 8.62 (s, 1 H), 8.49-8.53 (m, 2 H), 7.51 (t, J=1.8 Hz, 1 H), 7.38-7.49 (m, 3 H), 7.23 (t, J=7.9 Hz, 1 H), 7.08-7.16 (m, 4 H), 6.88 (ddd, J=1.0, 1.3, 7.8 Hz, 1 H), 4.30 (t, J=5.9 Hz, 2H), 3.16-3.23 (m, 2 H), 2.35-2.45 (m, 2 H).
HRMS (ESI) calcd for C24H21FN5OS [M+H]⁺ 446.1446, found 446.1463.

1-(2,4-difluoro-phenyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH₂)₃, R6=2,4-difluorophenyl]

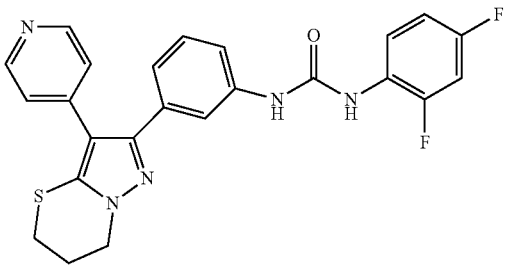 [SMILES: O=C(Nc1cccc(-c2nn3c(c2-c2ccncc2)SCCC3)c1)Nc1ccc(F)cc1F]

HPLC (254 nm): R_t: 6.12 min.
¹H NMR (401 MHz, DMSO-d₆) δ=9.01 (s, 1 H), 8.49-8.56 (m, 2 H), 8.43 (d, J=2.1 Hz, 1 H), 8.06 (td, J=6.2, 9.3 Hz, 1 H), 7.52 (t, J=1.8 Hz, 1 H), 7.44 (ddd, J=0.9, 2.2, 8.1 Hz, 1 H), 7.30 (ddd, J=2.9, 8.9, 11.6 Hz, 1 H), 7.25 (t, J=7.9 Hz, 1 H), 7.12-7.15 (m, 2 H), 7.04 (ddd, J=2.1, 8.2, 10.0 Hz, 1 H), 6.89 (ddd, J=1.0, 1.3, 7.8 Hz, 1 H), 4.30 (t, J=6.0 Hz, 2 H), 3.16-3.23 (m, 2 H), 2.35-2.44 (m, 2 H).

HRMS (ESI) calcd for C24H20F2N5OS [M+H]⁺ 464.1351, found 464.1366.

1-[3-(3-pyridin-4-yl-6,7-dihydro-5H-pyrazolo[5,1-b][1,3]thiazin-2-yl)-phenyl]-3-(4-trifluoromethyl-phenyl)-urea [(I)C, X=CH, R', R2, R3, R4, R5, Y=H, W=(CH₂)₃, R6=4-trifluoromethylphenyl] (Cpd. no 3)

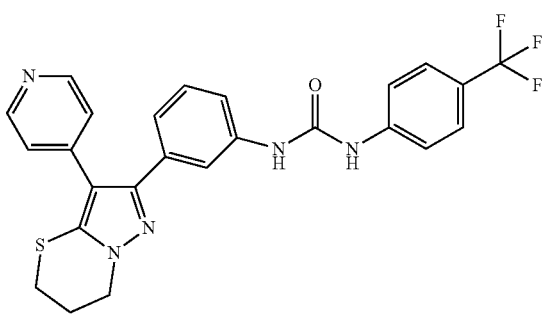 [SMILES: O=C(Nc1ccc(C(F)(F)F)cc1)Nc1cccc(-c2nn3c(c2-c2ccncc2)SCCC3)c1]

HPLC (254 nm): R_t: 6.65 min.
¹H NMR (401 MHz, DMSO-d₆) δ=9.02 (s, 1 H), 8.81 (s, 1 H), 8.42-8.61 (m, 2 H), 7.64 (s, 4 H), 7.54 (t, J=1.8 Hz, 1H), 7.46 (ddd, J=1.0, 2.2, 8.2 Hz, 1 H), 7.25 (t, J=7.9 Hz, 1 H), 7.11-7.17 (m, 2 H), 6.91 (ddd, J=1.1, 1.3, 7.9 Hz, 1 H), 4.30 (t, J=5.9 Hz, 2 H), 3.15-3.24 (m, 2 H), 2.39 (dq, J=5.6, 5.9 Hz, 2 H).

HRMS (ESI) calcd for C25H21F3N5OS [M+H]⁺ 496.1414, found 496.1408.

1-pyridin-3-yl-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH₂)₃, R6=3-pyridinyl]

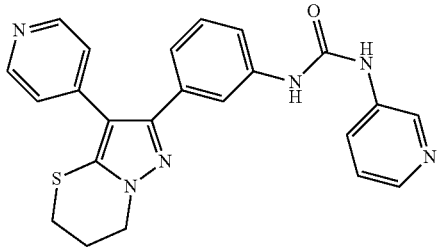 [SMILES: O=C(Nc1cccnc1)Nc1cccc(-c2nn3c(c2-c2ccncc2)SCCC3)c1]

HPLC (254 nm): R_t: 5.01 min.
¹H NMR (401 MHz, DMSO-d₆) δ=8.82 (s, 1 H), 8.77 (s, 1 H), 8.59 (br. d, J=2.2 Hz 1H), 8.51 (dd, 2 H), 8.19 (dd, J=1.5, 4.6 Hz, 1 H), 7.91 (ddd, 1 H), 7.53 (t, J=1.8 Hz, 1 H), 7.46 (ddd, J=1.0, 2.2, 8.1 Hz, 1 H), 7.31 (ddd, 1H), 7.25 (t, J=7.9 Hz, 1 H), 7.13 (m, 2 H), 6.90 (ddd, J=1.0, 1.3, 7.9 Hz, 1 H), 4.30 (t, J=5.9 Hz, 2 H), 3.20, (m, 2 H), 2.39 (m, 2 H).

HRMS (ESI) calcd for C23H20N6OS [M+H]⁺ 429.1492, found 429.1494.

1-[3-(3-pyridin-4-yl-6,7-dihydro-5H-pyrazolo[5,1-b][1,3]thiazin-2-yl)-phenyl]-3-thiophen-2-yl-urea [(I)C, X=CH, R', R2, R3, R4, R5, Y=H, W=(CH₂)₃, R6=2-thiophenyl]

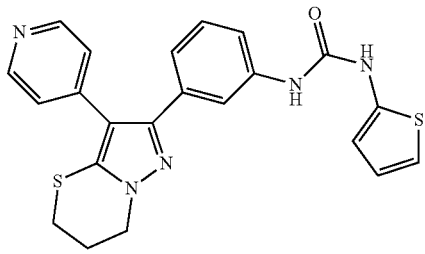 [SMILES: O=C(Nc1cccc(-c2nn3c(c2-c2ccncc2)SCCC3)c1)Nc1cccs1]

HPLC (254 nm): R_t: 5.70 min.
¹H NMR (401 MHz, DMSO-d₆) δ=9.55 (s, 1H), 8.75 (s, 1H), 8.51 (m, 2H), 7.55 (t, J=1.8 Hz, 1H), 7.44 (ddd, J=0.9, 2.2, 8.1 Hz, 1H), 7.23 (t, J=7.9 Hz, 1H), 7.12 (m, 2H), 6.87 (m, 2H), 6.81 (dd, J=3.7, 5.5 Hz, 1H), 6.55 (dd, J=1.5, 3.7 Hz, 1H), 4.30 (t, J=6.0 Hz, 2H), 3.20 (m, 2H), 2.39 (m, 2H).

HRMS (ESI) calcd for C22H19N5OS2 [M+H]⁺ 434.1104, found 434.1107.

Example 4

Preparation of [3-(3-pyridin-4-yl-6,7-dihydro-5H-pyrazolo[5,1-b][1,3]thiazin-2-yl)-phenyl]-carbamic acid phenyl ester [(I)B, X=CH, R', R2, R3, R4, R5=H, W=(CH₂)₃, R'6=phenyl]

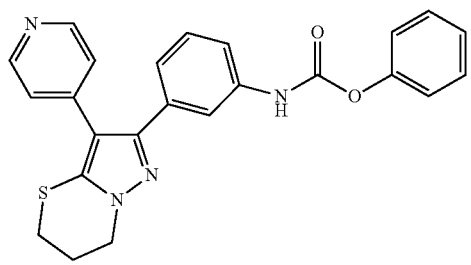 [SMILES: O=C(Nc1cccc(-c2nn3c(c2-c2ccncc2)SCCC3)c1)Oc1ccccc1]

Method E
Step d 3-(3-Pyridin-4-yl-6,7-dihydro-5H-pyrazolo[5,1-b][1,3]thiazin-2-yl)-phenylamine (prepared as described in Example 3) (30 mg, 0.097 mmol) was dissolved in dry DCM (1 mL) under nitrogen atmosphere. Triethylamine (0.018 mL, 0.126 mmol, 1.3 eq) and phenylchloroformate (0.015 mL, 0.117 mmol, 1.2 eq) were added and the mixture was stirred at room temperature for 30 minutes. The reaction mixture was diluted with DCM and washed with water, dried over $Na_2SO_4$ and concentrated to dryness. The residue was taken up with ethylether and filtered to give 27 mg (65%) of [3-(3-pyridin-4-yl-6,7-dihydro-5H-pyrazolo[5,1-b][1,3]thiazin-2-yl)-phenyl]-carbamic acid phenyl ester as white solid.

HPLC (254 nm): $R_t$: 6.17 min.

$^1$H NMR (401 MHz, DMSO-$d_6$)=10.24 (br. s., 1 H), 8.51 (dd, J=1.5, 4.5 Hz, 2 H), 7.63 (s, 1 H), 7.49-7.54 (m, 1H), 7.40-7.47 (m, 2 H), 7.24-7.30 (m, 2 H), 7.21 (d, J=7.4 Hz, 2 H), 7.11-7.13 (m, 2 H), 6.93 (d, J=7.9 Hz, 1 H), 4.29 (t, J=5.9 Hz, 2 H), 3.20 (d, J=11.2 Hz, 2 H), 2.33-2.45 (m, 2 H).

HRMS (ESI) calcd for C24H21N4O2S [M+H]$^+$ 429.1380, found 429.1377.

Operating in an analogous way the following compound was prepared:

[3-(3-pyridin-4-yl-6,7-dihydro-5H-pyrazolo[5,1-b][1,3]thiazin-2-yl)-phenyl]-carbamic acid 4-methoxyphenyl ester [(I)B, X=CH, R', R2, R3, R4, R5=H, W=(CH$_2$)$_3$, R'6=4-methoxyphenyl]

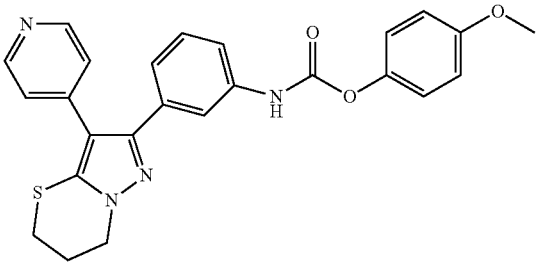 [SMILES: COc1ccc(OC(=O)Nc2cccc(-c3nn4c(c3-c3ccncc3)SCCC4)c2)cc1]

The product was obtained in 72% yield as white powder.
HPLC (254 nm): $R_t$: 6.15 min.

$^1$H NMR (401 MHz, DMSO-$d_6$) δ=10.17 (s, 1 H), 8.49-8.52 (m, 2 H), 7.58-7.63 (m, 1 H), 7.48-7.54 (m, 1 H), 7.26 (t, J=7.9 Hz, 1 H), 7.08-7.16 (m, 4 H), 6.96 (d, J=9.1 Hz, 2 H), 6.92 (ddd, J=1.0, 1.2, 7.8 Hz, 1 H), 4.29 (t, J=6.0 Hz, 2 H), 3.77 (s, 3 H), 3.15-3.23 (m, 2 H), 2.32-2.43 (m, 2 H).

HRMS (ESI) calcd for C25H23N4O3S [M+H]$^+$ 459.1486, found 459.1490.

Example 5

Preparation of 3-fluoro-N-[3-(3-pyridin-4-yl-6,7-dihydro-5H-pyrazolo[5,1-b][1,3]thiazin-2-yl)-phenyl]-benzenesulfonamide [(I)A, X=CH, R', R2, R3, R4, R5=H, W=(CH$_2$)$_3$, R'6=3-fluorophenyl] (Cpd no 4)

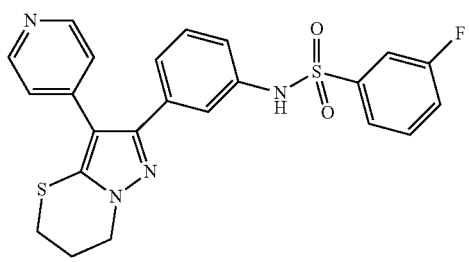 [SMILES: O=S(=O)(Nc1cccc(-c2nn3c(c2-c2ccncc2)SCCC3)c1)c1cccc(F)c1]

Method E
Step c 3-(3-Pyridin-4-yl-6,7-dihydro-5H-pyrazolo[5,1-b][1,3]thiazin-2-yl)-phenylamine (prepared as described in Example 3) (30 mg, 0.097 mmol) was dissolved in dry DCM (1 mL). At room temperature 3-fluorobenzensulfonylchloride (0.013 mL, 0.097 mmol, 1 eq) was added followed by NMM (0.011 mL, 0.097 mmol, 1 eq) and the mixture was stirred for 2 hours. It was then diluted with DCM and washed with water and brine. The organic layer was dried over $Na_2SO_4$ and concentrated under reduced pressure. The crude product was purified by chromatography on silica gel (eluant DCM/MeOH/NH$_3$ 7 N in MeOH 95:5:0.5) to give 42 mg (93%) of 3-fluoro-N-[3-(3-pyridin-4-yl-6,7-dihydro-5H-pyrazolo[5,1-b][1,3]thiazin-2-yl)-phenyl]-benzenesulfonamide.

HPLC (254 nm): $R_t$: 5.92 min.

$^1$H NMR (401 MHz, DMSO-$d_6$) δ=10.40 (s, 1 H), 8.46-8.51 (m, 2 H), 7.62 (td, J=7.9, 5.5 Hz, 1 H), 7.48-7.54 (m, 2 H), 7.42-7.48 (m, 1 H), 7.22 (t, J=7.9 Hz, 1 H), 7.13 (t, J=1.8 Hz, 1 H), 7.09 (ddd, J=1.0, 2.3, 8.0 Hz, 1 H), 6.98-7.04 (m, 3 H), 4.27 (t, J=6.0 Hz, 2 H), 3.19 (d, J=11.1 Hz, 2 H), 2.25-2.45 (m, 2 H).

HRMS (ESI) calcd for C23H20FN4O2S2 [M+H]$^+$ 467.1006, found 467.1014.

Operating in an analogous way the following compounds were prepared:

2,5-difluoro-N-[3-(3-pyridin-4-yl-6,7-dihydro-5H-pyrazolo[5,1-b][1,3]thiazin-2-yl)-phenyl]-benzenesulfonamide [(I)A, X=CH, R', R2, R3, R4, R5=H, W=(CH$_2$)$_3$, R'6=2,5-difluorophenyl] (Cpd. no 9)

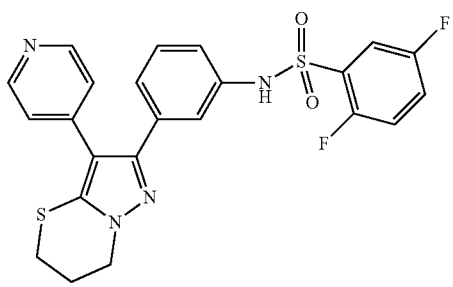 [SMILES: O=S(=O)(Nc1cccc(-c2nn3c(c2-c2ccncc2)SCCC3)c1)c1cc(F)ccc1F]

HPLC (254 nm): $R_t$: 5.94 min.

$^1$H NMR (401 MHz, DMSO-$d_6$) δ=10.74 (br. s., 1 H), 8.43-8.50 (m, 2 H), 7.46-7.63 (m, 3 H), 7.23 (t, J=8.0 Hz, 1 H), 7.14 (t, J=1.8 Hz, 1 H), 7.09 (ddd, J=1.0, 2.2, 8.1 Hz, 1 H), 7.00-7.03 (m, 2 H), 6.99-7.01 (m, 1 H), 4.27 (t, J=5.9 Hz, 2 H), 3.15-3.22 (m, 2 H), 2.31-2.43 (m, 2 H).

HRMS (ESI) calcd for C23H19F2N4O2S2 [M+H]$^+$ 485.0912, found 485.0914.

propane-1-sulfonic acid [3-(3-pyridin-4-yl-6,7-dihydro-5H-pyrazolo[5,1-b][1,3]thiazin-2-yl)-phenyl]-amide [(I)A, X=CH, R', R2, R3, R4, R5=H, W=(CH₂)₃, R'6=propyl]

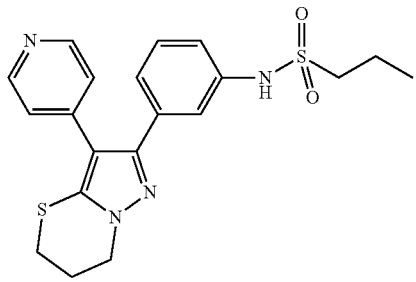 [SMILES: CCCS(=O)(=O)Nc1cccc(-c2nn3c(c2-c2ccncc2)SCCC3)c1]

HPLC (254 nm): R$_t$: 5.46 min.

¹H NMR (401 MHz, DMSO-d₆) δ=9.78 (s, 1 H), 8.49-8.52 (m, 2 H), 7.30 (t, J=7.9 Hz, 1 H), 7.20 (t, J=1.7 Hz, 1H), 7.17 (ddd, J=1.1, 8.0, 2.2 Hz, 1 H), 7.10-7.13 (m, 2 H), 7.07 (ddd, J=1.2, 1.3, 7.8 Hz, 1 H), 4.29 (t, J=5.9 Hz, 2 H), 3.16-3.23 (m, 2 H), 2.89-2.97 (m, 2 H), 2.34-2.43 (m, 2 H), 1.62 (sxt, J=7.5 Hz, 2 H), 0.92 (t, J=7.4 Hz, 3H).

HRMS (ESI) calcd for C20H23N4O2S2 [M+H]⁺ 415.1257, found 415.1255.

thiophene-3-sulfonic acid [3-(3-pyridin-4-yl-6,7-dihydro-5H-pyrazolo[5,1-b][1,3]-thiazin-2-yl)-phenyl]-amide [(I)A, X=CH, R', R2, R3, R4, R5=H, W=(CH₂)₃, R'6=3-thiophenyl] (Cpd. no 14)

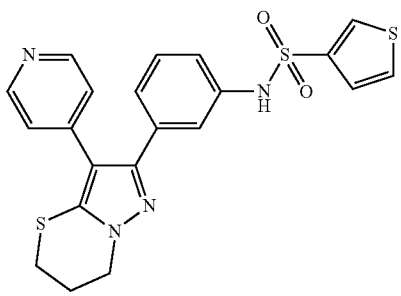

HPLC (254 nm): R$_t$: 5.65 min.

¹H NMR (401 MHz, DMSO-d₆) δ=10.24 (s, 1H), 8.44-8.57 (m, 2H), 8.06 (dd, J=1.3, 3.0 Hz, 1H), 7.70 (dd, J=3.0, 5.1 Hz, 1H), 7.22 (t, J=7.9 Hz, 1H), 7.15-7.19 (m, 2H), 7.11 (ddd, J=1.1, 2.2 Hz, 1H), 7.07 (m, 2H), 6.99 (dt, J=1.3, 7.7 Hz, 1H), 4.28 (t, J=6.0 Hz, 2H), 3.14-3.23 (m, 2H), 2.31-2.42 (m, 2H).

HRMS (ESI) calcd for C21H18N4O2S3 [M+H]⁺ 455.0665, found 455.0667.

furan-2-sulfonic acid [3-(3-pyridin-4-yl-6,7-dihydro-5H-pyrazolo[5,1-b][1,3]thiazolo[5,1-b][1,3]thiazin-2-yl)-phenyl]-amide [(I)A, X=CH, R', R2, R3, R4, R5=H, W=(CH₂)₃, R'6=2-furyl] (Cpd no 13)

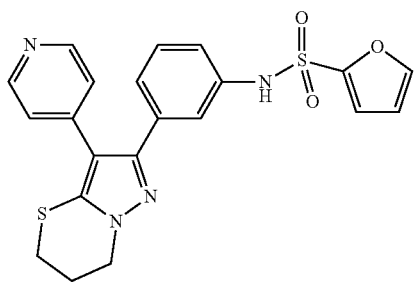 [SMILES: O=S(=O)(Nc1cccc(-c2nn3c(c2-c2ccncc2)SCCC3)c1)c1ccco1]

HPLC (254 nm): R$_t$: 5.53 min.

¹H NMR (401 MHz, DMSO-d₆) δ=10.67 (s, 1 H), 8.55 (m, 2 H), 7.94 (dd, J=0.9, 1.8 Hz, 1 H), 7.26 (t, J=7.9 Hz, 1H), 7.16 (m, 3 H) 7.13 (dt, J=1.1, 8.0 Hz, 1 H), 7.02-7.06 (m, 2 H), 6.62 (dd, J=1.8, 3.5 Hz, 1 H), 4.29 (t, J=5.9 Hz, 2 H), 3.18-3.24 (m, 2 H), 2.34-2.43 (m, 2 H).

HRMS (ESI) calcd for C21H18N4O3S2 [M+H]⁺ 439.0893, found 439.0898.

pyridine-3-sulfonic acid [3-(3-pyridin-4-yl-6,7-dihydro-5H-pyrazolo[5,1-b][1,3]-thiazin-2-yl)-phenyl]-amide [(I)A, X=CH, R', R2, R3, R4, R5=H, W=(CH₂)₃, R'6=3-pyridinyl] (Cpd. no 15)

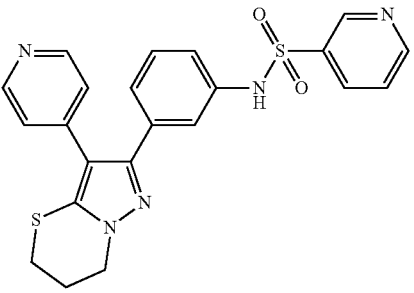 [SMILES: O=S(=O)(Nc1cccc(-c2nn3c(c2-c2ccncc2)SCCC3)c1)c1cccnc1]

HPLC (254 nm): R$_t$: 5.12 min.

¹H NMR (401 MHz, DMSO-d₆) δ=10.51 (s, 1 H), 8.80 (td, J=1.6, 4.1 Hz, 2H), 8.53 (dd, J=1.5, 4.6 Hz, 2H), 8.04 (ddd, J=1.6, 2.4, 8.1 Hz, 1H), 7.61 (ddd, J=0.9, 4.8, 8.1 Hz, 1H), 7.24 (t, J=7.9 Hz, 1H), 7.07-7.15 (m, 4H), 7.04 (dt, J=1.3, 7.8 Hz, 1H), 4.28 (t, J=5.9 Hz, 2H), 3.15-3.23 (m, 2H), 2.40-2.33 (m, 2 H).

HRMS (ESI) calcd for C22H19N5O2S2 [M+H]⁺ 450.1053, found. 450.1051.

Example 6

Preparation of N-[3-(3-pyridin-4-yl-6,7-dihydro-5H-pyrazolo[5,1-b][1,3]thiazin-2-yl)-phenyl]-2-(4-trifluoromethyl-phenyl)-acetamide [(I)E, X=CH, R', R2, R3, R4, R5=H, W=(CH₂)₃, R6=4-trifluoromethylphenylmethyl](Cpd. no 12)

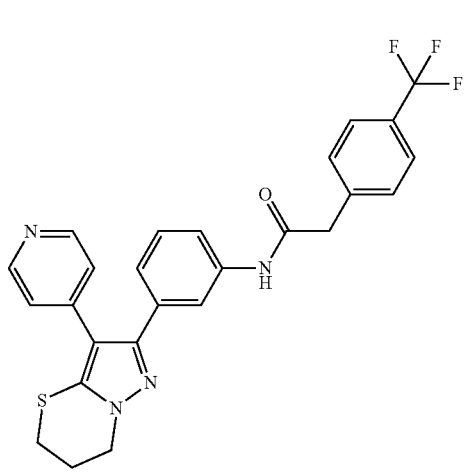 [SMILES: O=C(Cc1ccc(C(F)(F)F)cc1)Nc1cccc(-c2nn3c(c2-c2ccncc2)SCCC3)c1]

Method E

Step h

To a solution of 3-(3-pyridin-4-yl-6,7-dihydro-5H-pyrazolo[5,1-b][1,3]thiazin-2-yl)-phenylamine (prepared as described in Example 3) (100 mg, 0.324 mmol) in dichloromethane (8 mL), were added in the following order: (4-trifluoromethyl-phenyl)-acetic acid (132 mg, 0.648 mmol), DIPEA (125 mg, 166 uL, 0.972 mmol) and TBTU (312 mg, 0.972 mmol). The reaction mixture was stirred at room temperature for 3 hours. Then it was poured into a solution of saturated NaHCO3, the phases separated, and the organic phase was washed twice with saturated NaHCO3, and twice with water. The organic solvent was evaporated to dryness and the product was purified by flash chromatography over silica gel using dichloromethane-methanol (98:2) as the eluant system. N-[3-(3-pyridin-4-yl-6,7-dihydro-5H-pyrazolo[5,1-b][1,3]thiazin-2-yl)-phenyl]-2-(4-trifluoromethyl-phenyl)-acetamide was obtained as a colorless solid (115 mg, 72%).

HPLC (254 nm): $R_t$: 6.50 min.

$^1$H NMR (401 MHz, DMSO-d$_6$) δ=10.26 (s, 1 H), 8.50 (m, 2 H), 7.73 (t, J=1.7 Hz, 1 H), 7.70 (d, J=8.0 Hz, 2 H), 7.60 (dt, J=1.0, 8.2 Hz, 1 H), 7.54 (d, J=8.0 Hz, 2 H), 7.24 (t, J=7.9 Hz, 1 H), 7.12 (m, 2 H), 6.90 (ddd, J=1.3, 7.9 Hz, 1 H), 4.28 (t, J=6.0 Hz, 2 H), 3.75 (s, 2 H), 3.18-3.21 (m, 2 H), 2.38 (m, 2 H).

HRMS (ESI) calcd for C26H21F3N4OS [M+H]$^+$ 495.1461, found 495.1459.

Example 7

Preparation of 1-(4-methyl-benzenesulfonyl)-3-[3-(3-pyridin-4-yl-6,7-dihydro-5H-pyrazolo[5,1-b][1,3]thiazin-2-yl)-phenyl]-urea [(I)C, X=CH, R', R2, R3, R4, R5, Y=H, W=(CH₂)₃, R6=4-methylphenylsulfonyl]

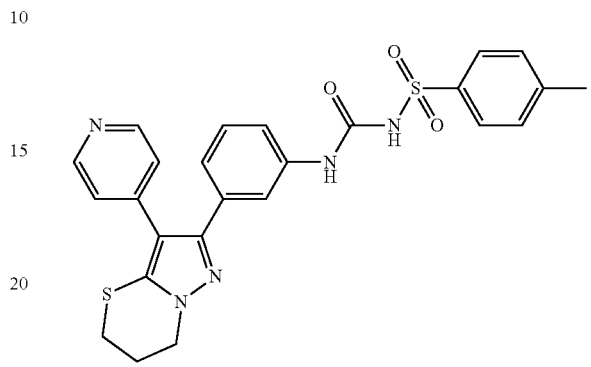

Method E

Step e

To a solution of 3-(3-pyridin-4-yl-6,7-dihydro-5H-pyrazolo[5,1-b][1,3]thiazin-2-yl)-phenylamine (prepared as described in Example 3) (50 mg, 0.162 mmol) in dichloromethane (5 mL), 4-methyl-benzenesulfonyl isocyanate (28 mg, 0.178 mmol) was added in one portion. The reaction mixture was stirred at room temperature for 2 hours and evaporated to dryness. The reaction mixture was purified by flash chromatography over silica gel using dichloromethane-methanol (97:3) as the eluant system. 1-(4-methyl-benzenesulfonyl)-3-[3-(3-pyridin-4-yl-6,7-dihydro-5H-pyrazolo-[5,1-b][1,3]thiazin-2-yl)-phenyl]-urea was obtained as a colorless solid (21 mg, 32%).

HPLC (254 nm): $R_t$: 5.35 min.

$^1$H NMR (401 MHz, DMSO-d$_6$) δ=8.83 (s, 1H), 8.49 (m, 2H), 7.84 (m, 2H), 7.46, (m, 1H), 7.43 (d, J=7.9 Hz, 2H), 7.29 (m, 1H), 7.20 (t, J=7.9 Hz, 1H), 7.09 (m, 2H), 6.88 (m, 1H), 4.28 (m, 2H), 3.19 (m, 2H), 2.41 (s, 3H), 2.34, (m, 2H).

HRMS (ESI) calcd for C25H23N5O3S2 [M+H]$^+$ 506.1315, found 506.1317.

Example 8

Preparation of 3-(7-pyridin-4-yl-2,3-dihydro-pyrazolo[5,1-b]thiazol-6-yl)-phenol [(I)P, X=CH, R', R2, R3, R4, R5=H, W=(CH₂)₂] (Cpd. no 7)

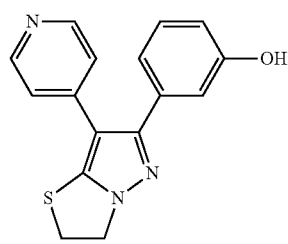 [SMILES: Oc1cccc(-c2nn3c(c2-c2ccncc2)SCC3)c1]

Method A
Step e

1-(3-methoxy-phenyl)-2-pyridin-4-yl-ethanone

To a solution of 4-methyl-pyridine (1.04 mL, 10.74 mmol) in anhydrous tetrahydrofuran (40 mL) at 0° C. a 1 M solution of sodium hexamethyldisilazide in tetrahydrofuran (21.5 mL, 21.5 mmol, 2 eq) was added dropwise and the reaction was stirred for 20 minutes. Neat methyl 3-methoxybenzoate (1.8 g, 10.74 mmol, 1 eq) was then added and the reaction was stirred at 0° C. for one hour. The reaction was poured into saturated ammonium chloride solution and, after basification with saturated aqueous NaHCO3, extracted with ethyl acetate. The organic layer was washed with brine, dried over anhydrous sodium sulfate and concentrated under reduced pressure. The crude product was taken up with n-hexane and filtered to give 1.75 g (72%) of the desired product as beige solid (1.775 g, 50%).

HPLC (254 nm): $R_t$: 5.13 min.
$^1$H NMR (401 MHz, DMSO-$d_6$) δ=8.52 (d, J=5.9 Hz, 2 H), 7.66 (ddd, J=0.9, 1.6, 7.7 Hz, 1 H), 7.53 (dd, J=1.6, 2.4 Hz, 1 H), 7.49 (t, J=7.9 Hz, 1 H), 7.30 (d, J=6.0 Hz, 2 H), 7.25 (ddd, J=0.9, 2.7, 8.2 Hz, 1 H), 4.49 (s, 2 H), 3.84 (s, 3 H).
HRMS (ESI) calcd for C14H14NO2 [M+H]$^+$ 228.1019, found 228.1017.

Method A
Step f

2-[1,3]dithietan-2-ylidene-1-(3-methoxy-phenyl)-2-pyridin-4-yl-ethanone

To a solution of 1-(3-methoxy-phenyl)-2-pyridin-4-yl-ethanone (1 g, 4.40 mmol) in dry DMSO (22 mL) under nitrogen atmosphere solid potassium carbonate (1.8 g, 13.20 mmol, 3 eq) was added at room temperature, followed by carbon disulfide (0.796 mL, 13.20 mmol, 3 eq) and dibromomethane (0.926 mL, 13.20 mmol, 3 eq). The reaction mixture was stirred at room temperature for 3 hour and then poured into stirred iced water (150 mL). The yellow precipitate was filtered, washed with water and dried at 60° C. under reduced pressure for 1 hour to give 1.18 g (83%) of 2-[1,3]dithietan-2-ylidene-1-(3-methoxy-phenyl)-2-pyridin-4-yl-ethanone.

HPLC (254 nm): $R_t$: 5.67 min.
$^1$H NMR (401 MHz, DMSO-$d_6$) δ=8.46-8.50 (m, 2 H), 7.13-7.20 (m, 1 H), 7.06-7.11 (m, 2 H), 6.91-6.98 (m, 1H), 6.74-6.80 (m, 2 H), 4.33 (s, 2 H), 3.58 (s, 3 H).
HRMS (ESI) calcd for C16H14NO2S2 [M+H]$^+$ 316.0461, found 316.0459.

Method A
Step g

5-(3-methoxy-phenyl)-4-pyridin-4-yl-2H-pyrazole-3-thiol

2-[1,3]Dithietan-2-ylidene-1-(3-methoxy-phenyl)-2-pyridin-4-yl-ethanone (1.18 g, 3.17 mmol) was suspended into a 1 M solution of hydrazine in THF and heated to 70° C. for two hours. The suspension was then concentrated under reduced pressure, taken up with a small volume of ethanol and diluted with THF (10 mL) and stirred for 5 minutes. The solid was filtered, washed with THF and dried at 50° C. for 2 hours. 1.26 g of 5-(3-methoxy-phenyl)-4-pyridin-4-yl-2H-pyrazole-3-thiol were obtained as an orange solid and used in the following step without further purification.

MS (ESI): 284 [M+H]$^+$.

Method B
Step a

6-(3-methoxy-phenyl)-7-pyridin-4-yl-2,3-dihydro-pyrazolo[5,1-b]thiazole 5-(3-Methoxy-phenyl)-4-pyridin-4-yl-2H-pyrazole-3-thiol (630 mg, 2.22 mmol) was dissolved in dry DMF (22 mL) under nitrogen atmosphere. Solid potassium carbonate (1.5 g, 11.1 mmol, 5 eq) was added followed by 1,2-dibromoethane (0.192 mL, 2.22 mmol, 1 eq) and the suspension was stirred at room temperature overnight. The reaction mixture was then concentrated under reduced pressure, diluted with ethyl acetate and washed with saturated aqueous NaHCO$_3$ and brine. The organic layer was dried over Na$_2$SO$_4$ and concentrated to dryness to give 420 mg (61% over two steps) of crude 6-(3-methoxy-phenyl)-7-pyridin-4-yl-2,3-dihydro-pyrazolo[5,1-b]thiazole which was used without further purification in the following step.

MS (ESI): 310 [M+H]$^+$.

Method I

3-(7-pyridin-4-yl-2,3-dihydro-pyrazolo[5,1-b]thiazol-6-yl)-phenol [(I)P, X=CH, R', R2, R3, R4, R5=H, W=(CH$_2$)$_2$]

6-(3-Methoxy-phenyl)-7-pyridin-4-yl-2,3-dihydro-pyrazolo[5,1-b]thiazole (420 mg, 1.36 mmol) was dissolved in dry DCM (8 mL) and cooled to 0° C. A 1 M solution of boron tribromide in DCM (5.4 mL, 5.4 mmol, 4 eq) was added dropwise and the mixture was allowed to warm to room temperature and stirred for 2 hours. Ice was then added to the reaction mixture, followed by saturated aqueous NaHCO$_3$ until pH 6. The organic layer was separated and the aqueous phase was extracted with a ethylacetate/methanol mixture. The combined organic layers were dried over sodium sulfate and concentrated to dryness. The crude product was purified by chromatography on silica gel (eluant: DCM/MeOH 95:5) to give 200 mg (50%) of the desired product as white foam.

HPLC (254 nm): $R_t$: 4.66 min.
$^1$H NMR (401 MHz, DMSO-$d_6$) δ=9.48 (s, 1 H), 8.44-8.50 (m, 2 H), 7.19 (t, J=7.9 Hz, 1 H), 7.05-7.09 (m, 2 H), 6.75-6.82 (m, 3 H), 4.45 (t, J=7.6 Hz, 2 H), 4.00 (t, J=7.6 Hz, 2 H).
HRMS (ESI) calcd for C16H14N3OS [M+H]$^+$ 296.0852, found 296.0853.

Example 9

Preparation of 3-(3-pyridin-4-yl-6,7-dihydro-5H-pyrazolo[5,1-b][1,3]thiazin-2-yl)-phenol [(I)P, X=CH, R', R2, R3, R4, R5=H, W=(CH$_2$)$_3$] (Cpd. no 8)

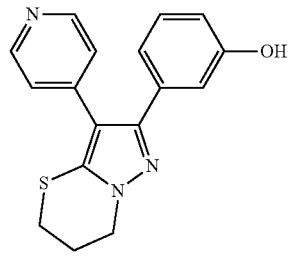 [SMILES: Oc1cccc(-c2nn3c(c2-c2ccncc2)SCCC3)c1]

The above compound was prepared starting from 5-(3-methoxy-phenyl)-4-pyridin-4-yl-2H-pyrazole-3-thiol as described in Example 8 but using 1,3-dibromopropane instead of 1,2-dibromoethane as the alkylating agent.

HPLC (254 nm): $R_t$: 4.84 min.

$^1$H NMR (401 MHz, DMSO-$d_6$) δ=9.40 (s, 1 H), 8.49-8.52 (m, 2 H), 7.11-7.14 (m, 3 H), 6.76-6.79 (m, 1 H), 6.68-6.75 (m, 2 H), 4.27 (t, J=6.0 Hz, 2 H), 3.16-3.22 (m, 2 H), 2.37 (br. s., 2 H).

HRMS (ESI) calcd for C17H16N3OS [M+H]$^+$ 310.1009, found 310.1015.

Example 10

Preparation of 1-[3-(4,4-dioxo-3-pyridin-4-yl-4,5,6,7-tetrahydro-pyrazolo-[5,1b][1,3]thiazin-2-yl)-phenyl]-3-m-tolyl-urea [(I)AC, X=CH, R1, R2, R3, R4, R5=H, W2=(CH$_2$)$_3$, m=2, A=NHCONH, R6=3-methylphenyl]

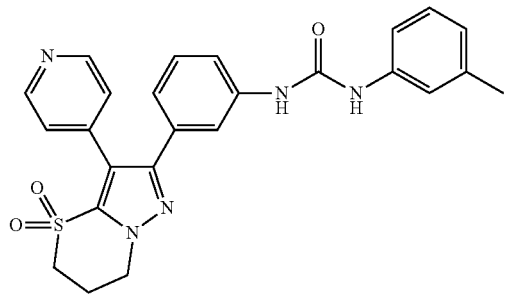 [SMILES: Cc1cccc(NC(=O)Nc2cccc(-c3nn4c(c3-c3ccncc3)S(=O)(=O)CCC4)c2)c1]

Method L

1-[3-(3-Pyridin-4-yl-6,7-dihydro-5H-pyrazolo[5,1-b][1,3]-thiazin-2-yl)-phenyl]-3-m-tolyl-urea (prepared as described in Example 3) (29 mg, 0.066 mmol) was dissolved in a 2:1 ethanol/water mixture (1 mL). Oxone was added (162 mg, 0.263 mmol, 4 eq) and the mixture was stirred at room temperature for 16 hours. It was then diluted with water and saturated aqueous NaHCO$_3$ was added until pH 7. The aqueous phase was then extracted with ethyl acetate and the organic phase was dried over Na$_2$SO$_4$ and evaporated to dryness. The crude product was purified by chromatography on silica gel (eluant: ethylacetate) to give 14 mg of the desired product.

HPLC (254 nm): $R_t$: 4.69 min.

$^1$H NMR (401 MHz, DMSO-$d_6$) δ=8.69 (s, 1 H), 8.58-8.63 (m, 2 H), 8.52 (s, 1 H), 7.59 (t, J=1.8 Hz, 1 H), 7.42 (ddd, J=0.9, 2.1, 8.1 Hz, 1 H), 7.31-7.36 (m, 2 H), 7.26-7.29 (m, 1 H), 7.19-7.25 (m, 2 H), 7.16 (t, J=7.6 Hz, 1H), 6.73-6.85 (m, 2 H), 4.50 (t, J=6.0 Hz, 2 H), 3.70-3.94 (m, 2 H), 2.64 (br. s., 2 H), 2.28 (s, 3 H).

HRMS (ESI) calcd for C25H24N5O3S [M+H]$^+$ 474.1595, found 474.1586.

Operating in an analogous way the following compounds were prepared:

1-(4-chloro-3-trifluoromethyl-phenyl)-3-[3-(4,4-dioxo-3-pyridin-4-yl-4,5,6,7-tetrahydro-pyrazolo[5,1-b][1,3]thiazin-2-yl)-phenyl]-urea [(I)AC, X=CH, R1, R2, R3, R4, R5=H, W2=(CH$_2$)$_3$, m=2, A=NHCONH, R6=4-chloro-3-trifluoromethyl-phenyl]

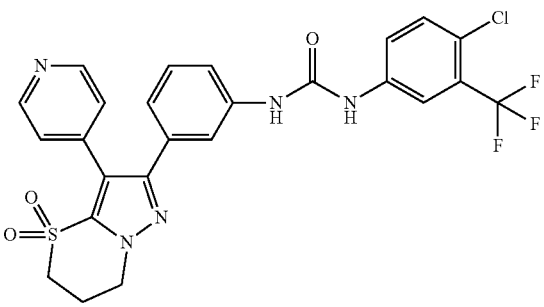 [SMILES: O=C(Nc1cccc(-c2nn3c(c2-c2ccncc2)S(=O)(=O)CCC3)c1)Nc1ccc(Cl)c(C(F)(F)F)c1]

HPLC (254 nm): $R_t$: 5.62 min.

$^1$H NMR (401 MHz, DMSO-$d_6$) δ=9.10 (s, 1 H), 8.89 (s, 1 H), 8.60 (m, 2 H), 8.09 (d, J=1.3 Hz, 1 H), 7.61-7.63 (m, 2 H), 7.60 (t, J=1.8 Hz, 1 H), 7.44 (ddd, J=0.9, 2.2, 8.1 Hz, 1 H), 7.30-7.35 (m, 2 H), 7.24 (t, J=7.9 Hz, 1 H), 6.84 (ddd, J=1.1, 1.3, 7.9 Hz, 1 H), 4.50 (t, J=6.0 Hz, 2 H), 3.77-3.84 (m, 2 H), 2.58-2.70 (m, 2 H).

HRMS (ESI) calcd for C25H20ClF3N5O3S [M+H]$^+$ 562.0922, found 562.0923.

1-[3-(4,4-dioxo-3-pyridin-4-yl-4,5,6,7-tetrahydro-pyrazolo[5,1-b][1,3]thiazin-2-yl)-phenyl]-3-(4-trifluoromethyl-phenyl)-urea [(I)AC, X=CH, R1, R2, R3, R4, R5=H, W2=(CH$_2$)$_3$, m=2, A=NHCONH, R6=4-trifluoromethyl-phenyl]

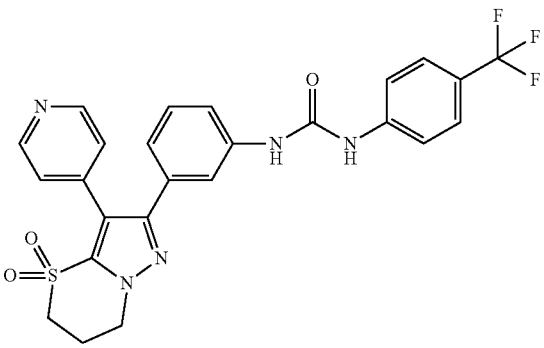 [SMILES: O=C(Nc1ccc(C(F)(F)F)cc1)Nc1cccc(-c2nn3c(c2-c2ccncc2)S(=O)(=O)CCC3)c1]

HPLC (254 nm): $R_t$: 6.25 min.

$^1$H NMR (401 MHz, DMSO-$d_6$) δ=9.05 (s, 1 H), 8.85 (s, 1 H), 8.55-8.66 (m, 2 H), 7.64 (s, 4 H), 7.60 (t, J=1.9 Hz, 1H), 7.44 (ddd, J=1.1, 1.2, 7.1 Hz, 1 H), 7.31-7.36 (m, 2 H), 7.25 (t, J=7.9 Hz, 1 H), 6.84 (ddd, J=1.2, 1.3, 7.8 Hz, 1 H), 4.50 (t, J=5.9 Hz, 2 H), 3.76-3.86 (m, 2 H), 2.59-2.69 (m, 2 H).

HRMS (ESI) calcd for C25H21F3N5O3S [M+H]$^+$ 528.1312, found 528.1312.

N-[3-(4,4-dioxo-3-pyridin-4-yl-4,5,6,7-tetrahydro-pyrazolo[5,1-b][1,3]thiazin-2-yl)-phenyl]-3-fluoro-benzenesulfonamide [(I)AC, X=CH, R1, R2, R3, R4, R5=H, W2=(CH$_2$)$_3$, m=2, A=NHSO2, R6=3-fluorophenyl]

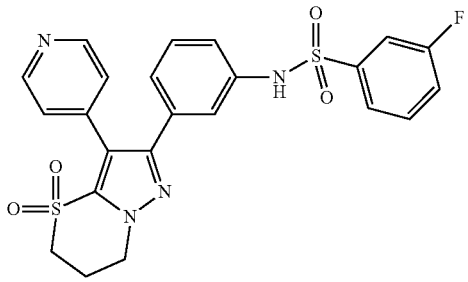 [SMILES: O=S1(=O)CCCn2nc(-c3cccc(NS(=O)(=O)c4cccc(F)c4)c3)c(-c3ccncc3)c21]

HPLC (254 nm): R$_t$: 5.47 min.
$^1$H NMR (401 MHz, DMSO-d$_6$) δ=10.44 (s, 1 H), 8.56 (d, J=5.9 Hz, 2 H), 7.62 (td, J=7.9, 5.5 Hz, 1 H), 7.48-7.56 (m, 2 H), 7.42-7.47 (m, 1 H), 7.19-7.23 (m, 3 H), 7.06-7.14 (m, 2 H), 6.96 (ddd, J=1.2, 1.3, 7.8 Hz, 1 H), 4.46 (t, J=5.9 Hz, 2 H), 3.79 (d, J=11.8 Hz, 2 H), 2.58-2.66 (m, 2 H).
HRMS (ESI) calcd for C23H20FN4O4S2 [M+H]$^+$ 499.0905, found 499.0901.

N-[3-(4,4-dioxo-3-pyridin-4-yl-4,5,6,7-tetrahydro-pyrazolo[5,1-b][1,3]thiazin-2-yl)-phenyl]-2,5-difluoro-benzenesulfonamide [(I)AC, X=CH, R1, R2, R3, R4, R5=H, W2=(CH$_2$)$_3$, m=2, A=NHSO2, R6=2,5-difluorophenyl]

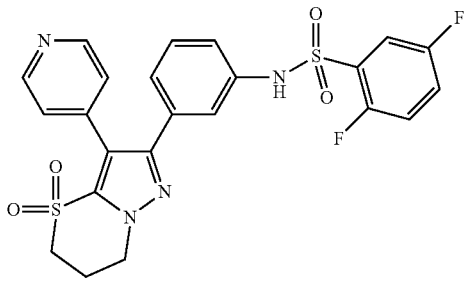 [SMILES: O=S1(=O)CCCn2nc(-c3cccc(NS(=O)(=O)c4cc(F)ccc4F)c3)c(-c3ccncc3)c21]

HPLC (254 nm): R$_t$: 5.48 min.
$^1$H NMR (401 MHz, DMSO-d$_6$) δ=10.81 (s, 1 H), 8.56 (d, J=5.7 Hz, 2 H), 7.57-7.64 (m, 1 H), 7.46-7.54 (m, 2 H), 7.20-7.27 (m, 3 H), 7.09-7.13 (m, 2 H), 6.97 (ddd, J=1.2, 1.3, 7.8 Hz, 1 H), 4.46 (t, J=5.9 Hz, 2 H), 3.76-3.83 (m, 2 H), 2.57-2.66 (m, 2 H).
HRMS (ESI) calcd for C23H19F2N4O4S2 [M+H]$^+$ 517.0811, found 517.0799.

3-(1,1-dioxo-7-pyridin-4-yl-2,3-dihydro-pyrazolo[5,1-b]thiazol-6-yl)-phenol [(I)AC, X=CH, R1, R2, R3, R4, R5, R6=H, W2=(CH$_2$)$_2$, m=2, A=O] (Cpd. no 10)

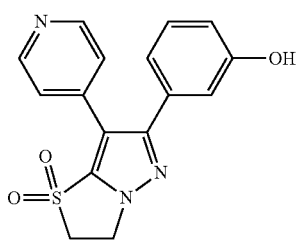 [SMILES: O=S1(=O)CCn2nc(-c3cccc(O)c3)c(-c3ccncc3)c21]

HPLC (254 nm): R$_t$: 4.46 min.
$^1$H NMR (401 MHz, DMSO-d$_6$) δ=9.60 (s, 1 H), 8.58-8.62 (m, 2 H), 7.26-7.29 (m, 2 H), 7.19-7.26 (m, 1 H), 6.80-6.87 (m, 3 H), 4.83-4.89 (m, 2 H), 4.38-4.45 (m, 2 H).
HRMS (ESI) calcd for C16H14N3O3S [M+H]$^+$ 328.0751, found 328.0757.

Example 11

Preparation of 1-[3-(1-oxo-7-pyridin-4-yl-2,3-dihydro-pyrazolo[5,1-b]thiazol-6-yl)-phenyl]-3-(4-trifluoromethyl-phenyl)-urea [(I)AC, X=CH, R1, R2, R3, R4, R5=H, W2=(CH$_2$)$_2$, m=1, A=NHCONH, R6=4-trifluoromethylphenyl] (Cpd. no 19)

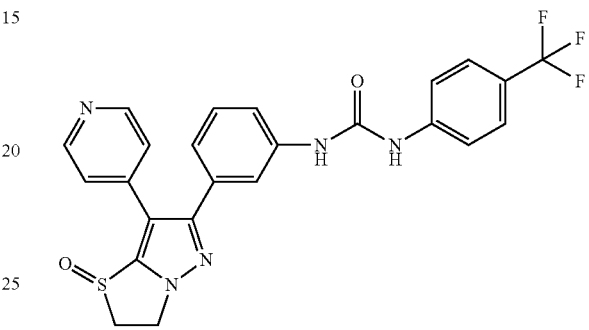

Method L
1-[3-(7-Pyridin-4-yl-2,3-dihydro-pyrazolo[5,1-b]thiazol-6-yl)-phenyl]-3-(4-trifluoro-methyl-phenyl)-urea (prepared as described in Example 1) (135 mg, 0.280 mmol) was dissolved in DCM (3 mL). Freshly prepared 10% sodium metaperiodate on silica gel (675 mg, 0.280 mmol, 1 eq) was added and the mixture was stirred at room temperature overnight. A further addition of reagent (130 mg) was made and the mixture was stirred for 3 more hours. It was then evaporated to dryness and purified by chromatography on silica gel (eluant DCM/MeOH 95:5) to give 94 mg of sulfoxide as a white powder (68% yield).
HPLC (254 nm): R$_t$: 5.82 min.
$^1$H NMR (401 MHz, DMSO-d$_6$) δ=9.07 (s, 1 H), 8.91 (s, 1 H), 8.60 (dd, J=1.6, 4.5 Hz, 2 H), 7.59-7.68 (m, 5 H), 7.52 (ddd, J=1.0, 2.1, 8.2 Hz, 1 H), 7.28-7.37 (m, 3 H), 7.02 (ddd, J=1.0, 1.3, 7.9 Hz, 1 H), 4.95 (ddd, J=6.4, 7.9, 12.1 Hz, 1 H), 4.74 (ddd, J=2.2, 8.2, 12.1 Hz, 1 H), 4.20 (dt, J=8.1, 13.7 Hz, 1 H), 3.77 (ddd, J=2.2, 6.3, 13.7 Hz, 1 H).
HRMS (ESI) calcd for C24H19F3N5O2S [M+H]$^+$ 498.1206, found 498.1207.

Example 12

Preparation of N-(4-tert-butyl-phenyl)-3-(7-pyridin-4-yl-2,3-dihydro-pyrazolo[5,1-b]thiazol-6-yl)-benzamide [(I)I, X=CH, R',R2,R3,R4,R5,Y=H, W=(CH$_2$)$_2$, R6=4-tert-butylphenyl] (Cpd no 15)

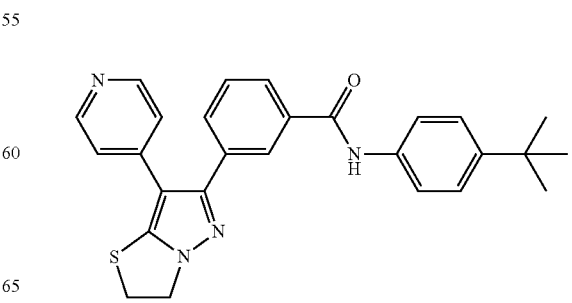

Method A
Step a

3-cyanophenyl)-hydroxymethyl]-phosphonic acid dimethyl ester

3-Cyanobenzaldehyde (10 g, 76.25 mmol) was dissolved in ethylacetate (80 mL). Triethylamine (16 mL, 0.115 mmol, 1.5 eq) was added, followed by dimethylphosphite (9.1 mL, 99.13 mmol, 1.3 eq) and the mixture was stirred at room temperature for 2 hours. It was then diluted with ethylacetate (150 mL) and washed with saturated aqueous ammonium chloride (3×50 mL). The organic layer was dried over $Na_2SO_4$, concentrated under reduced pressure and dried under vacuum at 40° C. for 2 h to give 15 g of (3-cyanophenyl)-hydroxy-methyl]-phosphonic acid dimethyl ester as a white solid (82% yield).

$^1$H NMR (401 MHz, DMSO-$d_6$) δ=7.81 (q, J=1.8 Hz, 1 H), 7.77 (dt, J=1.8, 7.8 Hz, 2 H), 7.58 (t, J=7.7 Hz, 1 H), 6.51 (dd, J=5.9, 14.4 Hz, 1 H), 5.16 (dd, J=5.9, 13.9 Hz, 1 H), 3.64 (d, J=10.2 Hz, 3 H), 3.62 (d, J=10.2 Hz, 3 H).

HRMS (ESI) calcd for C10H13NO4P [M+H]$^+$ 242.0577, found 242.0576.

Method A
Step b

[(3-cyano-phenyl)-(tetrahydro-pyran-2-yloxy)methyl]phosphonic acid dimethyl ester 3,4-Dihydro-2H-pyran (10.83 g, 128.70 mmol) and p-toluenesulfonic acid (0.34 g, 1.75 mmol) were added to a solution of [(3-cyanophenyl-hydroxy-methyl]-phosphonic acid dimethyl ester (14.10 g, 58.50 mmol) in dry toluene (195 ml) and the reaction mixture was stirred under nitrogen atmosphere at 50° C. for 3 h. The solvent was then removed under vacuum and the residue was taken up with ethyl acetate (100 ml). The organic layer was washed with a saturated $NaHCO_3$ solution (1×100 ml), brine (1×100 ml) and dried over $Na_2SO_4$. The filtrate was evaporated to dryness to give the crude [(3-cyanophenyl)-(tetrahydro-pyran-2-yloxy)-methyl]phosphonic acid dimethyl ester as a yellow oil (19 g, 58.46 mmol, 100%).

$^1$H NMR (401 MHz, DMSO-$d_6$) δ=7.85-7.74 (m, 3 H), 7.63-7.58 (m, 1 H), 5.24 (d, J=17.4 Hz, 1 H), 5.24 (d, J=12.7 Hz, 1 H), 4.96 (t, J=3.0 Hz, 1 H), 4.39 (t, J=2.5 Hz, 1 H), 3.89 (dt, J=6.0, 11.7 Hz, 1 H), 3.71 (d, J=10.5 Hz, 3 H), 3.64 (d, J=10.5 Hz, 3 H), 3.64 (td, J=7.6, 10.4 Hz, 2 H), 3.51 (d, J=12.2 Hz, 1 H), 1.87-1.31 (m, 6 H).

HRMS (ESI) calcd for C15H20NO5P [M+H]$^+$ 326.1152, found 326.1158.

Method A
Step c

3-[(E)-2-pyridin-4-yl-1-(tetrahydro-pyran-2-yloxy)-vinyl]-benzonitrile

Sodium hydride (2.28 g, 94.98 mmol) was added to a solution of [(3-cyano-phenyl)-(tetrahydro-pyran-2-yloxy)-methyl]phosphonic acid dimethyl ester (20.58 g, 63.3 mmol) in dry THF and the mixture was stirred at room temperature for 15'. Pyridine-4-carbaldehyde (6.78 g, 63.3 mmol) was then added and the reaction mixture was stirred at 50° C. for 3 h under nitrogen atmosphere. In order to affect completion a further addition of pyridine-4-carbaldehyde (0.68 g, 6.33 mmol) was required. Distilled water (40 ml) was slowly poured into the reaction mixture and the solvent (THF) was removed under reduced pressure. The water layer was extracted with EtOAc (3×100 ml), DCM (1×100 ml) and the organic layers were dried over $Na_2SO_4$. The filtrate was evaporated to dryness to give the crude product 3-[(E)-2-Pyridin-4-yl-1-(tetrahydro-pyran-2-yloxy)-vinyl]-benzonitrile as a brown oil (19.0 g, 62.10 mmol, 98%).

MS ESI (M+H) calc 307.1441; found. 307.1436 (C19H18N2O2).

Method A
Step d

3-(pyridin-4-yl-acetyl)-benzonitrile

3-[(E)-2-Pyridin-4-yl-1-(tetrahydro-pyran-2-yloxy)-vinyl]-benzonitrile (19.0 g, 62.1 mmol) was dissolved into methanol (0.4 ml) and a solution of HCl 1N (0.04 ml) was added. The mixture was stirred at 50° C. for 1 h. Upon reaction completion, the solvent was evaporated and a saturated $NaHCO_3$ solution was added dropwise to the left water layer leading to the precipitation of 3-(pyridin-4-yl-acetyl)-benzonitrile (4) as a yellow solid (9.65 g, 43.4 mmol, 70%).

$^1$H NMR (401 MHz, DMSO-d6) δ=8.49-8.57 (m, 3 H), 8.32 (dt, J=1.2, 8.6 Hz, 1 H), 8.15 (ddd, J=1.2, 1.4, 7.9 Hz, 1 H), 7.79 (dd, J=0.5, 15.6 Hz, 1 H), 7.28-7.35 (m, 2 H), 4.57 (s, 2 H).

MS ESI (M+H) calc 223.0866; found. 223.0864 (C14H10N2O).

Method A
Step f

3-(2-[1,3]dithietan-2-ylidene-2-pyridin-4-yl-acetyl)-benzonitrile

To a solution of 3-(pyridin-4-yl-acetyl)-benzonitrile (12.5 g, 56 mmol) in dry DMSO (280 mL) under nitrogen atmosphere solid potassium carbonate (23.36 g, 169 mmol, 3 eq) was added at room temperature, followed by carbon disulfide (10.2 mL, 169 mmol, 3 eq) and dibromomethane (11.86 mL, 169 mmol, 3 eq). The reaction mixture was stirred at room temperature for 2 hours and then poured into stirred iced water (1.5 L mL). The orange precipitate was filtered, washed with water and dried at 60° C. under reduced pressure for 1 hour. The crude product was purified by silica gel chromatography (SP1, eluant: n-hexane/ethyl acetate 2:8) to obtain 10.1 g of yellow solid (58%).

HPLC (254 nm): $R_t$: 5.41 min.

$^1$H NMR (401 MHz,DMSO-d6) δ=8.45-8.51 (m, 2 H), 7.85 (dt, J=1.8, 6.8 Hz, 1 H), 7.65 (ddd, J=1.0, 1.1, 1.8 Hz, 1 H), 7.42-7.52 (m, 2 H), 7.08-7.13 (m, 2 H), 4.37 (s, 2 H).

HRMS (ESI) calcd for C16H11N2OS2 [M+H]$^+$ 311.0308, found 311.0312.

Method A
Step g

3-(5-Mercapto-4-pyridin-4-yl-1H-pyrazol-3-yl)-benzonitrile 3-(2-[1,3]Dithietan-2-ylidene-2-pyridin-4-yl-acetyl)-benzonitrile (5 g, 16.1 mmol) was suspended in absolute ethanol (50 mL) and heated to 60° C. Hydrazine monohydrate (3.13 mL, 64.4 mmol, 4 eq) was added dropwise and the mixture was stirred at 60° C. for 2 hours. The suspension was concentrated to about ¼ of the original volume, diluted with THF (50 mL) and stirred for 5 minutes. The yellow solid was filtered, washed with THF and dried at 50° C. for 1 hours. The crude product (4.59 g) was used in the following step without further purification.

MS (ESI): 279 [M+H]$^+$.

Method B
Step a

3-(7-pyridin-4-yl-2,3-dihydro-pyrazolo[5,1-b]thiazol-6-yl)-benzonitrile 3-(5-Mercapto-4-pyridin-4-yl-1H-pyrazol-3-yl)-benzonitrile (4.59 g, 16.1 mmol) was dissolved in dry DMF (200 mL) under nitrogen atmosphere. Solid potassium carbonate (11.1 g, 80.5 mmol, 5 eq) was added followed by 1,2-dibromoethane (1.53 mL, 17.71 mmol, 1.1 eq) and the suspension was stirred at room temperature for 4 hours. The reaction mixture was then concentrated under reduced pressure and diluted with ethyl acetate. It was washed with saturated aqueous NaHCO$_3$ and brine. The organic layer was dried over Na$_2$SO$_4$ and concentrated under reduced pressure. The crude product was treated with methanol and the solid was filtered and discarded. The mother liquor was evaporated to dryness and purified by chromatography on silica gel (eluant DCM/MeOH 97:3) to give 1.27 g of 3-(7-pyridin-4-yl-2,3-dihydro-pyrazolo[5,1-b]thiazol-6-yl)-benzonitrile as a white solid (26% over 2 steps).

HPLC (254 nm): R$_t$: 5.35 min.

$^1$H NMR (401 MHz, DMSO-d$_6$) δ=8.52 (d, J=4.5 Hz, 2 H), 7.87 (dt, J=1.4, 7.7 Hz, 1 H), 7.83 (t, J=1.7 Hz, 1 H), 7.71 (dt, J=7.9, 1.3 Hz, 1 H), 7.62 (t, J=8.1 Hz, 1 H), 7.07 (dd, J=1.5, 4.6 Hz, 2 H), 4.49 (t, J=7.6 Hz, 2 H), 4.03 (t, J=7.6 Hz, 2 H).

HRMS (ESI) calcd for C17H13N4S [M+H]$^+$ 305.0856, found 305.0854.

Method G
Step a

3-(7-pyridin-4-yl-2,3-dihydro-pyrazolo[5,1-b]thiazol-6-yl)-benzoic acid 3-(7-Pyridin-4-yl-2,3-dihydro-pyrazolo[5,1-b]thiazol-6-yl)-benzonitrile (80 mg, 0.263 mmol) was suspended in 3 N HCl (4 mL) and irradiated in the microwave oven at 150° C. for 45 minutes. While cooling to room temperature the product crystallized as the hydrochloride. It was filtered and washed with water. The solid was taken up with toluene and evaporated to dryness three times and then dried under vacuum. 90 g of 3-(7-pyridin-4-yl-2,3-dihydro-pyrazolo[5,1-b]thiazol-6-yl)-benzoic acid hydrochloride were obtained as a beige solid (76% yield).

HPLC (254 nm): R$_t$: 2.79 min.

HRMS (ESI) calcd for C17H14N3O2S [M+H]$^+$ 324.0801, found 324.0793.

Method B
Step b

N-(4-tert-butyl-phenyl)-3-(7-pyridin-4-yl-2,3-dihydro-pyrazolo[5,1-b]thiazol-6-yl)-benzamide 3-(7-Pyridin-4-yl-2,3-dihydro-pyrazolo[5,1-b]thiazol-6-yl)-benzoic acid hydrochloride (45 mg, 0.125 mmol) was dissolved in thionylchloride (1 mL) and stirred at 60° C. for 1 hour. The solvent was distilled and the residue was taken up with toluene, evaporated to dryness and dried under high vacuum for 1 h. The acid chloride was then dissolved in dry pyridine (1 mL) under nitrogen and 4-tert-butylaniline (0.030 mL, 0.187 mmol, 1.5 eq) was added. The mixture was stirred at room temperature for 1 h and then diluted with ethyl acetate and washed with saturated aqueous NaHCO$_3$ and brine. The organic layer was dried over Na$_2$SO$_4$ and concentrated under reduced pressure. The crude product was purified by chromatography on silica gel (eluant DCM/EtOH 95:5 to give 44 mg of N-(4-tert-butyl-phenyl)-3-(7-pyridin-4-yl-2,3-dihydro-pyrazolo[5,1-b]thiazol-6-yl)-benzamide as a white solid (77%).

HPLC (254 nm): R$_t$: 6.97 min.

$^1$H NMR (401 MHz, DMSO-d$_6$) δ=10.21 (s, 1 H), 8.48 (d, J=6.1 Hz, 2 H), 8.02-8.09 (m, 1 H), 7.93-8.01 (m, 1 H), 7.63-7.69 (m, 2 H), 7.52-7.54 (m, 2 H), 7.31-7.38 (m, 2 H), 7.05-7.10 (m, 2 H), 4.49 (t, J=7.6 Hz, 2 H), 4.02 (t, J=7.5 Hz, 2 H), 1.27 (s, 9 H).

HRMS (ESI) calcd for C27H27N4OS [M+H]$^+$ 455.1900, found 455.1900.

Operating in an analogous way the following compounds were prepared:

3-(7-pyridin-4-yl-2,3-dihydro-pyrazolo[5,1-b]thiazol-6-yl)-N-(4-trifluoromethyl-phenyl)-benzamide [(1)I, X=CH, R',R2,R3,R4,R5,Y=H, W=(CH$_2$)$_2$, R6=4-trifluoromethylphenyl] (Cpd no 24)

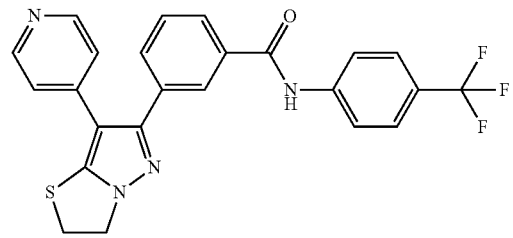 [SMILES: O=C(Nc1ccc(C(F)(F)F)cc1)c1cccc(-c2nn3c(c2-c2ccncc2)SCC3)c1]

HPLC (254 nm): R$_t$: 6.38 min.

$^1$H NMR (401 MHz, DMSO-d$_6$) δ=10.59 (s, 1 H), 8.44-8.48 (m, 2 H), 8.06 (s, 1 H), 7.94-8.01 (m, 3 H), 7.69 (d, J=8.7 Hz, 2 H), 7.52-7.57 (m, 2 H), 7.02-7.07 (m, 2 H), 4.47 (t, J=7.6 Hz, 2 H), 4.00 (t, J=7.5 Hz, 2 H).

HRMS (ESI) calcd for C24H18F3N4OS [M+H]$^+$ 467.1148, found 467.1144.

N-(4-chloro-phenyl)-3-(7-pyridin-4-yl-2,3-dihydro-pyrazolo[5,1-b]thiazol-6-yl)-benzamide [(I)I, X=CH, R',R2,R3,R4,R5,Y=H, W=(CH$_2$)$_2$, R6=4-chlorophenyl]

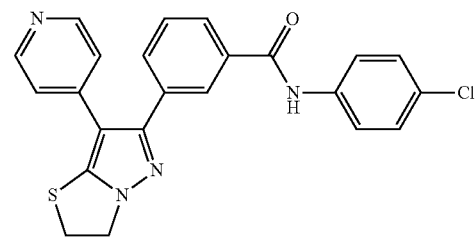 [SMILES: O=C(Nc1ccc(Cl)cc1)c1cccc(-c2nn3c(c2-c2ccncc2)SCC3)c1]

HPLC (254 nm): R$_t$: 6.05 min.

$^1$H NMR (401 MHz, DMSO-d$_6$) δ=10.41 (s, 1 H), 8.44-8.53 (m, 2 H), 8.06 (s, 1 H), 7.98 (td, J=1.8, 4.5 Hz, 1 H), 7.75-7.84 (m, 2 H), 7.55 (d, J=5.0 Hz, 2 H), 7.37-7.43 (m, 2 H), 7.03-7.10 (m, 2 H), 4.49 (t, J=7.6 Hz, 2 H), 4.03 (t, J=7.5 Hz, 2 H).

HRMS (ESI) calcd for C23H18ClN4OS [M+H]$^+$ 433.0885, found 433.0882.

3-(7-pyridin-4-yl-2,3-dihydro-pyrazolo[5,1-b]thiazol-6-yl)-N-(4-trifluoromethyl-benzyl)-benzamide [(I)I, X=CH, R',R2,R3,R4,R5,Y=H, W=(CH$_2$)$_2$, R6=4-trifluoromethylbenzyl]

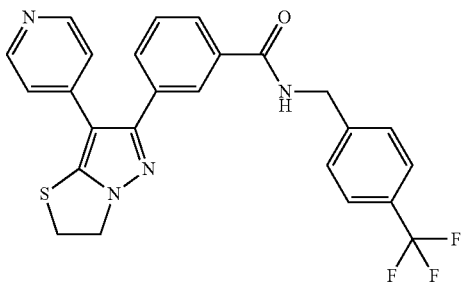 [SMILES: O=C(NCc1ccc(C(F)(F)F)cc1)c1cccc(-c2nn3c(c2-c2ccncc2)SCC3)c1]

HPLC (254 nm): R$_t$: 6.28 min.
$^1$H NMR (401 MHz, DMSO-d$_6$) δ=9.18 (t, J=5.9 Hz, 1 H), 8.43-8.51 (m, 2 H), 8.00-8.02 (m, 1 H), 7.91 (ddd, J=1.8, 2.5, 6.2 Hz, 1 H), 7.69 (d, J=8.2 Hz, 2 H), 7.47-7.52 (m, 4 H), 7.03-7.07 (m, 2 H), 4.54 (d, J=5.7 Hz, 2 H), 4.48 (t, J=7.6 Hz, 2 H), 4.02 (t, J=7.6 Hz, 2 H).
HRMS (ESI) calcd for C25H20F3N4OS [M+H]$^+$ 481.1305, found 481.1312.

Example 13

Preparation of 1-[3-(7-pyridin-4-yl-pyrazolo[5,1-b]thiazol-6-yl)-phenyl]-3-(4-trifluoromethyl-phenyl)-urea [(I)C, X=CH, R',R2,R3,R4,R5,Y=H, W=CHCH, R6=4-trifluoromethylphenyl] (Cpd. no 22)

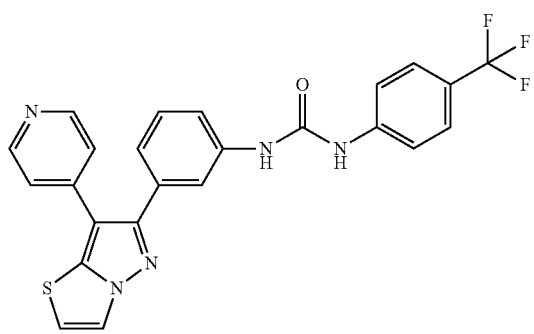 [SMILES: O=C(Nc1ccc(C(F)(F)F)cc1)Nc1cccc(-c2nn3ccsc3c2-c2ccncc2)c1]

Method B
Step b 3-hydroxy-6-(3-nitrophenyl)-7-pyridin-4-yl-2,3-dihydro-pyrazolo[5,1-b]thiazole 5-(3-Nitro-phenyl)-4-pyridin-4-yl-2H-pyrazole-3-thiol (prepared as described in Example 1) (3.92 g, 13.14 mmol) was dissolved in a 1:1 THF/water mixture (130 mL). Chloroacetaldehyde (55% in water, 2.31 mL, 19.71 mmol, 1.5 eq) was added and the solution was stirred at room temperature overnight. The reaction mixture was diluted with AcOEt and saturated aqueous NaHCO$_3$. The organic phase was washed with saturated aqueous NaHCO$_3$ and brine, dried and evaporated to dryness. 3.25 g of crude product were obtained as yellow solid (72%), which was used in the following step without further purification.

HPLC (254 nm): R$_t$: 5.04 min.
$^1$H-NMR (401 MHz, DMSO-d$_6$) δ=8.51-8.55 (m, 2 H), 8.24-8.28 (m, 2 H), 7.83 (ddd, J=1.2, 1.3, 7.8 Hz, 1 H), 7.68-7.74 (m, 1 H), 7.59 (d, J=6.0 Hz, 1 H), 7.12-7.15 (m, 2 H), 6.17 (td, J=1.5, 5.8 Hz, 1 H), 4.25 (dd, J=5.9, 12.0 Hz, 1 H), 3.68 (dd, J=1.7, 12.1 Hz, 1 H).
HRMS (ESI) calcd for C16H13N4O3S [M+H]$^+$ 341.0703, found 341.0706.
Method B
Step c 6-(3-nitrophenyl)-7-pyridin-4-yl-pyrazolo[5,1-b]thiazole 3-Hydroxy-6-(3-nitrophenyl)-7-pyridin-4-yl-2,3-dihydropyrazolo[5,1-b]thiazole (1 g, 2.938 mmol) was dissolved in dimethoxyethane (15 mL) under nitrogen atmosphere. Trifluoroacetic anhydride (0.8 mL, 5.664 mmol, 2 eq) and triethylamine (0.41 mL, 2.938 mmol, 1 eq) were added and the mixture was stirred at room temperature for 3 days. The solution was then diluted with ethyl acetate and washed with saturated aqueous NaHCO$_3$ and brine, dried and evaporated to dryness. The crude product was purified by chromatography on silica gel (eluant: DCM/MeOH 97:3) to give 417 mg (44%) of 6-(3-nitrophenyl)-7-pyridin-4-yl-pyrazolo[5,1-b]thiazole as white solid.
HPLC (254 nm): R$_t$: 5.89 min.
$^1$H-NMR (401 MHz, DMSO-d$_6$) δ=8.55 (d, J=6.0 Hz, 2 H), 8.44 (d, J=4.2 Hz, 1 H), 8.34 (t, J=1.8 Hz, 1 H), 8.30 (ddd, J=1.0, 2.4, 8.2 Hz, 1 H), 7.95 (ddd, J=1.0, 1.3, 8.0 Hz, 1 H), 7.75 (t, J=8.0 Hz, 1 H), 7.61 (d, J=4.2 Hz, 1H), 7.19-7.31 (m, 2 H). HRMS (ESI) calcd for C16H11N4O2S [M+H]$^+$ 323.0597, found 323.0588.
Method E
Step a 3-(7-pyridin-4-yl-pyrazolo[5,1-b]thiazol-6-yl)-phenylamine 6-(3-Nitrophenyl)-7-pyridin-4-yl-pyrazolo[5,1-b]thiazole (410 mg, 1.272 mmol) was dissolved in a 3:1 dioxane/water mixture (8 mL). Zinc powder (333 mg, 5.094 mmol, 4 eq) and ammonium chloride (680 mg, 12.72 mmol, 10 eq) were added and the mixture was stirred at 100° C. for 2 hours. It was then diluted with water, made basic by addition of saturated aqueous NaHCO$_3$ and extracted with ethyl acetate (3×20 mL). Combined organic layers were washed with sat. aq. NaHCO$_3$ and brine, dried over Na$_2$SO$_4$ and concentrated under reduced pressure. The crude product was purified by chromatography on silica gel (DCM/MeOH 97:3) to give 255 mg (68%) of 3-(7-pyridin-4-yl-pyrazolo[5,1-b]thiazol-6-yl)-phenylamine as white solid.
HPLC (254 nm): R$_t$: 4.80 min.
$^1$H-NMR (401 MHz, DMSO-d$_6$) δ=8.44-8.54 (m, 2 H), 8.35 (d, J=4.1 Hz, 1 H), 7.52 (d, J=4.1 Hz, 1 H), 7.18-7.24 (m, 2 H), 7.08 (t, J=7.8 Hz, 1 H), 6.74 (t, J=1.8 Hz, 1 H), 6.63 (ddd, J=1.0, 2.3, 8.1 Hz, 1 H), 6.59 (ddd, J=1.1, 1.3, 7.7 Hz, 1 H), 5.19 (br. s., 2 H).
HRMS (ESI) calcd for C16H13N4S [M+H]$^+$ 293.0856, found 293.0861.
Method E
Step e 1-[3-(7-pyridin-4-yl-pyrazolo[5,1-b]thiazol-6-yl)-phenyl]-3-(4-trifluoromethyl-phenyl)-urea 3-(7-Pyridin-4-yl-pyrazolo[5,1-b]thiazol-6-yl)-phenylamine (50 mg, 0.171 mmol) was dissolved in dry DCM (1 mL) under nitrogen atmosphere. p-trifluoromethylphenylisocyanate (0.025 mL, 0.179 mmol, 1.05 eq) was added and the mixture was stirred at room temperature for 1 hour. The solution was evaporated to dryness and the crude product was purified by chromatography on silica gel (DCM/MeOH 96:4) to give 80 mg of an oil, which after trituration with ethylether gave 63 mg of 1-[3-(7-pyridin-4-yl-pyrazolo[5,1-b]thiazol-6-yl)-phenyl]-3-(4-trifluoro-methyl-phenyl)-urea white solid (77%).

HPLC (254 nm): $R_t$: 6.73 min.

$^1$H-NMR (401 MHz, DMSO-$d_6$) δ=9.07 (s, 1 H), 8.91 (s, 1 H), 8.49-8.57 (m, 2 H), 8.40 (d, J=4.1 Hz, 1 H), 7.68 (t, J=1.8 Hz, 1 H), 7.60-7.66 (m, 4 H), 7.53-7.59 (m, 2 H), 7.38 (t, J=7.9 Hz, 1 H), 7.21-7.24 (m, 2 H), 7.13 (ddd, J=1.1, 1.3, 7.8 Hz, 1 H).

HRMS (ESI) calcd for C24H17F3N5OS [M+H]$^+$ 480.1101, found 480.1094.

Example 14

Preparation of 2,5-difluoro-N-[3-(7-pyridin-4-yl-pyrazolo[5,1-b]thiazol-6-yl)-phenyl]-benzenesulfonamide [(I)A, X=CH, R',R2,R3,R4,R5=H, W=CHCH, R'6=2,5-difluorophenyl] (Cpd. no 21)

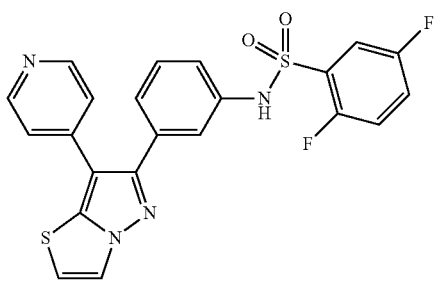 [SMILES: O=S(=O)(Nc1cccc(-c2nn3ccsc3c2-c2ccncc2)c1)c1cc(F)ccc1F]

Method E
Step c 3-(7-Pyridin-4-yl-pyrazolo[5,1-b]thiazol-6-yl)-phenylamine prepared as described in Example 13 (60 mg, 0.205 mmol) was dissolved in dry pyridine (1 mL) 2,5-difluorobenzenesulfonylchloride (0.030 mL, 0.226 mmol, 1.1.eq) was added and the solution was stirred at room temperature for 2.5 hours. The mixture was diluted with saturated aqueous NaHCO3 and extracted with ethyl acetate. Combined organic layers were washed with brine, dried and evaporated to dryness. The crude product was purified by chromatography on silica gel to give 73 mg of the desired product as an oil, which was treated with ethyl ether to give, after drying 57 mg of pale yellow solid (59%).

HPLC (254 nm): $R_t$: 6.00 min.

$^1$H-NMR (401 MHz, DMSO-$d_6$) δ=10.88 (s, 1 H), 8.46 (d, J=6.1 Hz, 2 H), 8.38 (d, J=4.1 Hz, 1 H), 7.55 (d, J=4.2 Hz, 1 H), 7.46-7.62 (m, 3 H), 7.35 (t, J=7.9 Hz, 1 H), 7.27 (t, J=1.7 Hz, 1 H), 7.17-7.24 (m, 2 H), 7.06-7.11 (m, 2 H).

HRMS (ESI) calcd for C22H15F2N4O2S2 [M+H]$^+$ 469.0599, found 469.0583.

Example 15

Preparation of N-[3-(7-pyridin-4-yl-pyrazolo[5,1-b]thiazol-6-yl)-phenyl]-2-(4-trifluoromethyl-phenyl)-acetamide [(I)E, X=CH, R', R2, R3, R4, R5, Y=H, W=CHCH, R6=(4-trifluoromethylphenyl)methyl]

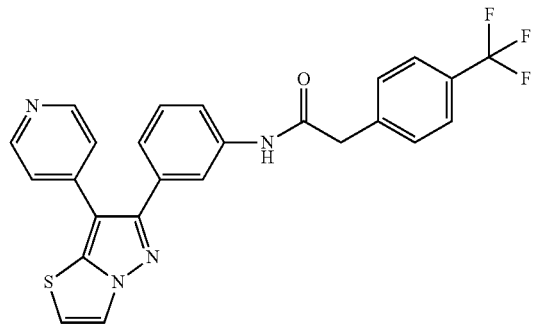 [SMILES: O=C(Cc1ccc(C(F)(F)F)cc1)Nc1cccc(-c2nn3ccsc3c2-c2ccncc2)c1]

Method E
Step h p-Trifluoromethylphenylacetic acid (45 mg, 0.222 mmol, 1.3 eq) was dissolved in dry DCM (2 mL) under nitrogen atmosphere. Oxalyl chloride (0.028 mL, 0.333 mmol, 1.95 eq) and dry DMF (0.005 mL) were added and the mixture was stirred at room temperature for 1 h. The mixture was evaporated to dryness and kept under high vacuum for 1 h. The acid chloride was then dissolved in dry DCM (2 mL) under nitrogen and a solution of 3-(7-pyridin-4-yl-pyrazolo[5,1-b]thiazol-6-yl)-phenylamine (prepared as described in Example 13) (50 mg, 0.171 mmol, 1 eq) in dry DCM (1 mL) was added, followed by triethylamine (0.036 mL, 0.257 mmol, 1.5 eq) and the mixture was stirred at room temperature for 2 hours. It was then diluted with DCM, washed with saturated aqueous NaHCO$_3$ and brine, dried and concentrated to dryness. The crude product was purified by chromatography on silica gel (DCM/MeOH 98:2) to give 25 mg (30%) of N-[3-(7-pyridin-4-yl-pyrazolo[5,1-b]thiazol-6-yl)-phenyl]-2-(4-trifluoromethyl-phenyl)-acetamideas off-white solid.

HPLC (254 nm): $R_t$: 6.36 min.

$^1$H-NMR (401 MHz, DMSO-$d_6$) δ=10.34 (s, 1 H), 8.51 (d, J=6.0 Hz, 2 H), 8.38 (d, J=4.1 Hz, 1 H), 7.83 (t, J=1.8 Hz, 1 H), 7.65-7.73 (m, 3 H), 7.51-7.57 (m, 3 H), 7.38 (t, J=7.9 Hz, 1 H), 7.18-7.22 (m, 2 H), 7.16 (dt, J=1.2, 7.8 Hz, 1 H), 3.77 (s, 2 H).

HRMS (ESI) calcd for C25H18F3N6O2S [M+H]$^+$ 479.1148 found 479.1149.

Example 16

Preparation of 7-pyridin-4-yl-6-{3-[3-(4-trifluoromethyl-phenyl)-ureido]-phenyl}-pyrazolo[5,1-b]thiazole-3-carboxylic acid amide [(I)C, X=CH, R', R2, R3, R4, R5, Y=H, W=CHCCONH2, R6=4-trifluoromethylphenyl] (Cpd no 16)

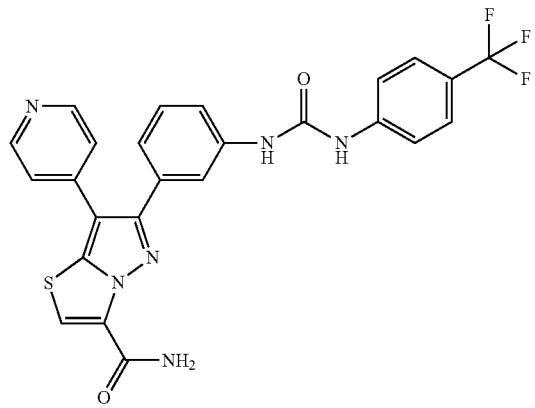 [SMILES: NC(=O)c1csc2c(-c3ccncc3)c(-c3cccc(NC(=O)Nc4ccc(C(F)(F)F)cc4)c3)nn12]

Method B
Step b

3-hydroxy-6-(3-nitrophenyl)-7-pyridin-4-yl-2,3-dihydro-pyrazolo[5,1b]thiazole-3-carboxylic acid ethyl ester 5-(3-Nitro-phenyl)-4-pyridin-4-yl-2H-pyrazole-3-thiol (prepared as described in Example 1) (100 mg, 0.335 mmol) was dissolved in dry dioxane (2 mL) under nitrogen atmosphere. Ethyl bromopyruvate (0.050 mL, 0.358 mmol, 1.07 eq) was added and the mixture was allowed to stir at room temperature for 1 h. The mixture was then diluted with ethylacetate and washed with saturated aqueous $NaHCO_3$ and brine, dried and evaporated to dryness. The crude product was purified by chromatography on silica gel (DCM/EtOH 97:3) to give 88 mg (64%) of 3-hydroxy-6-(3-nitrophenyl)-7-pyridin-4-yl-2,3-dihydro-pyrazolo[5,1b]thiazole-3-carboxylic acid ethyl ester.

HPLC (254 nm): $R_t$: 5.66 min.
$^1$H-NMR (401 MHz, DMSO-$d_6$) δ=8.54 (dd, J=1.6, 4.5 Hz, 2 H), 8.27 (dt, J=1.2, 8.2 Hz, 1 H), 8.24 (t, J=1.8 Hz, 1H), 7.80 (ddd, J=1.2, 1.4, 7.9 Hz, 1 H), 7.70 (t, J=8.1 Hz, 1 H), 7.12-7.17 (m, 2 H), 4.41 (d, J=12.3 Hz, 1 H), 4.30 (q, J=7.1 Hz, 2 H), 4.15 (br. s., 1 H), 3.96 (d, J=12.3 Hz, 1 H), 1.26 (t, J=7.1 Hz, 3 H).

HRMS (ESI) calcd for C25H18F3N6O2S [M+H]$^+$ 413.0914, found 413.0911.

Method B
Step c

6-(3-nitrophenyl)-7-pyridin-4-yl-pyrazolo[5,1-b]thiazole-3-carboxylic acid ethyl ester 3-Hydroxy-6-(3-nitrophenyl)-7-pyridin-4-yl-2,3-dihydro-pyrazolo[5,1b]thiazole-3-carboxylic acid ethyl ester (306 mg, 0.743 mmol) was dissolved in phosphorous oxichloride (15 mL) under nitrogen atmosphere and refluxed for 9 hours. Volatiles were distilled under reduced pressure and the residue was taken up with DCM and washed with saturated aqueous $NaHCO_3$ and brine, dried and evaporated to dryness. The crude product was used without further purification in the following step.

MS (ESI): 395 [M+H]$^+$.

Method E
Step a

6-(3-amino-phenyl)-7-pyridin-4-yl-pyrazolo[5,1-b]thiazole-3-carboxylic acid ethyl ester 6-(3-Nitrophenyl)-7-pyridin-4-yl-pyrazolo[5,1-b]thiazole-3-carboxylic acid ethyl ester (200 mg, 0.508 mmol) was dissolved in a 5:1 dioxane/water mixture (3 mL). Zinc powder (133 mg, 2.03 mmol, 4 eq) and ammonium chloride (271 mg, 5.08 mmol, 10 eq) were added and the mixture was stirred at 100° C. After 4 hours an addition of Zinc powder was made (37 mg) and heating was continued for 1.5 more hours. It was then diluted with water, made basic by addition of saturated aqueous $NaHCO_3$ and extracted with ethyl acetate (3×20 mL). Combined organic layers were washed with sat. aq. $NaHCO_3$ and brine, dried over $Na_2SO_4$ and concentrated under reduced pressure. 82 mg of 6-(3-amino-phenyl)-7-pyridin-4-yl-pyrazolo[5,1-b]thiazole-3-carboxylic acid ethyl ester were obtained as off-white solid, which was used without purification in the following step.

MS (ESI): 365 [M+H]$^+$.

Method E
Step e

7-pyridin-4-yl-6-{3-[3-(4-trifluoromethyl-phenyl)-ureido]-phenyl}-pyrazolo[5,1-b]thiazole-3-carboxylic acid ethyl ester 6-(3-Amino-phenyl)-7-pyridin-4-yl-pyrazolo[5,1-b]thiazole-3-carboxylic acid ethyl ester (33 mg, 0.091 mmol) was dissolved in dry DCM (0.5 mL) under nitrogen atmosphere. p-Trifluoromethylphenylisocyanate (0.014 mL, 0.100 mmol, 1.1 eq) was added and the mixture was stirred at room temperature for 1 hour. The solution was evaporated to dryness and the crude product was purified by chromatography on silica gel (DCM/MeOH 97:3) to give 31 mg (61%) of 7-pyridin-4-yl-6-{3-[3-(4-trifluoromethyl-phenyl)-ureido]-phenyl}-pyrazolo[5,1-b]thiazole-3-carboxylic acid ethyl ester.

MS (ESI): 552 [M+H]$^+$.

7-Pyridin-4-yl-6-{3-[3-(4-trifluoromethyl-phenyl)-ureido]-phenyl}-pyrazolo[5,1-b]thiazole-3-carboxylic acid amide 7-Pyridin-4-yl-6-{3-[3-(4-trifluoromethyl-phenyl)-ureido]-phenyl}-pyrazolo[5,1-b]-thiazole-3-carboxylic acid ethyl ester (31 mg, 0.056 mmol) was suspended a 7 N ammonia solution in methanol (1.5 mL) in a screw cap Pyrex tube. The mixture was stirred at 60° C. for 32 hours and then allowed to cool slowly to room temperature during the night. The suspended solid was filtered, washed with DCM and dried at 50° C. under high vacuum to give 13 mg of 7-pyridin-4-yl-6-{3-[3-(4-trifluoromethyl-phenyl)-ureido]-phenyl}-pyrazolo[5,1-b]thiazole-3-carboxylic acid amide (46%) as off-white solid.

HPLC (254 nm): $R_t$: 5.22 min.
$^1$H-NMR (401 MHz, DMSO-$d_6$) δ=9.10 (s, 1 H), 8.98 (s, 1 H), 8.56 (dd, J=1.6, 4.6 Hz, 2 H), 8.46 (s, 1 H), 8.40 (br. s., 1 H), 8.22 (s, 1 H), 7.68 (t, J=1.7 Hz, 1 H), 7.60-7.66 (m, 5 H), 7.40 (t, J=7.9 Hz, 1 H), 7.21-7.31 (m, 2 H), 7.17 (dt, J=1.0, 7.0 Hz, 1 H).

HRMS (ESI) calcd for C25H18F3N6O2S [M+H]$^+$ 523.1159, found 523.1161.

Example 17

Preparation of 6-[3-(2,5-difluoro-benzenesulfonylamino)-phenyl]-7-pyridin-4-yl-pyrazolo[5,1-b]thiazole-3-carboxylic acid amide [(I)A, X=CH, R',R2, R3,R4,R5=H, W=CHCCONH2, R'6=2,5-difluorophenyl] (Cpd. no 17)

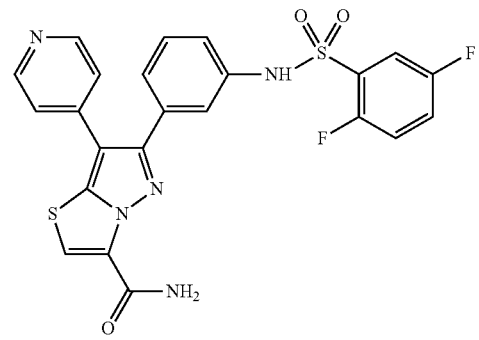 [SMILES: NC(=O)c1csc2c(-c3ccncc3)c(-c3cccc(NS(=O)(=O)c4cc(F)ccc4F)c3)nn12]

Method E

Step c

6-[3-(2,5-difluoro-benzenesulfonylamino)-phenyl]-7-pyridin-4-yl-pyrazolo[5,1-b]thiazole-3-carboxylic acid ethyl ester 6-(3-Amino-phenyl)-7-pyridin-4-yl-pyrazolo[5,1-b]thiazole-3-carboxylic acid ethyl ester (33 mg, 0.091 mmol) (prepared as described in Example 16) was dissolved in dry pyridine (0.5 mL) under nitrogen atmosphere. Difluorobenzenesulfonylchloride (0.013 mL, 0.100 mmol, 1.1 eq) was added and the solution was stirred at room temperature for 1 hours. The mixture was then concentrated under reduced pressure, taken up with ethyl acetate and washed with saturated aqueous NaHCO$_3$ and brine, dried and evaporated to dryness. The crude product was purified by chromatography on silica gel (DCM/MeOH 97:3) to give 30 mg (61%) of the desired product.

MS (ESI): 541 [M+H]$^+$.

6-[3-(2,5-Difluoro-benzenesulfonylamino)-phenyl]-7-pyridin-4-yl-pyrazolo[5,1-b]thiazole-3-carboxylic acid amide 6-[3-(2,5-Difluoro-benzenesulfonylamino)-phenyl]-7-pyridin-4-yl-pyrazolo[5,1-b]thiazole-3-carboxylic acid ethyl ester (30 mg, 0.055 mmol) was suspended a 7 N ammonia solution in methanol (1 mL) at 0° C. and stirred at this temperature for 18 hours. The mixture was evaporated to dryness and taken up with DCM and evaporated to dryness three times. The beige solid was dried under vacuum at room temperature to give 26 mg (93%) of 6-[3-(2,5-difluoro-benzenesulfonylamino)-phenyl]-7-pyridin-4-yl-pyrazolo[5,1-b]thiazole-3-carboxylic acid amide.

HPLC (254 nm): R$_t$: 4.44 min.

$^1$H-NMR (401 MHz, DMSO-d$_6$) δ=10.89 (s, 1 H), 8.51 (br. s., 2 H), 8.39 (br. s., 1 H), 8.37 (br. s., 1 H), 8.21 (s, 1 H), 7.46-7.62 (m, 3 H), 7.38 (t, J=7.8 Hz, 1 H), 7.28 (d, J=1.2 Hz, 1 H), 7.25 (dt, J=1.5, 6.0 Hz, 1 H), 7.23 (dd, J=1.1, 2.2 Hz, 1 H), 7.11-7.18 (m, 2 H).

HRMS (ESI) calcd for C23H16F2N5O3S2 [M+H]$^+$ 512.0657, found 512.0656.

Example 18

Preparation of 3-(7-pyridin-4-yl-pyrazolo[5,1-b]thiazol-6-yl)-phenol [(I)P, X=CH, R', R2, R3, R4, R5, W=CHCH] (Cpd. no 20)

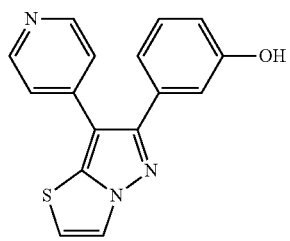 [SMILES: Oc1cccc(-c2nn3ccsc3c2-c2ccncc2)c1]

Method B

Step b

6-(3-methoxy-phenyl)-7-pyridin-4-yl-2,3-dihydropyrazolo[5,1-b]thiazol-3-ol 5-(3-Methoxy-phenyl)-4-pyridin-4-yl-2H-pyrazole-3-thiol prepared as described in Example 8 (115 mg, 0.406 mmol) was dissolved in a 1:1 THF/water mixture (3 mL). A 55% aqueous solution of chloroacetaldehyde (0.071 mL, 0.609 mmol, 1.5 eq) was added and the mixture was stirred at room temperature for 2 hours. It was then diluted with ethylacetate and washed with saturated aqueous NaHCO$_3$ and brine, dried over Na$_2$SO$_4$ and evaporated to dryness to give 123 mg (93%) of crude product, which was used without further purification in the following step.

MS (ESI): 326 [M+H]$^+$.

Method b

Step c

6-(3-methoxy-phenyl)-7-pyridin-4-yl-pyrazolo[5,1-b]thiazole

Crude 6-(3-methoxy-phenyl)-7-pyridin-4-yl-2,3-dihydropyrazolo[5,1-b]thiazol-3-ol (120 mg, 0.369 mmol) was dissolved in dry dimethoxyethane (2 mL) under nitrogen. Trifluoroacetic anhydride (0.200 mL, 1.416 mmol, 3.8 eq) and triethylamine (0.100 mL, 0.718 mmol, 2 eq) were added and the mixture was stirred at room temperature for 20 hours. The solution was then diluted with ethyl acetate and washed with saturated aqueous NaHCO$_3$ and brine, dried and evaporated to dryness. The crude product was purified by chromatography on silica gel (eluant: DCM/MeOH 97:3) to give 69 mg (61%) of 6-(3-methoxy-phenyl)-7-pyridin-4-yl-pyrazolo[5,1-b]thiazole as white solid.

HPLC (254 nm): R$_t$: 5.62 min.

$^1$H-NMR (401 MHz, DMSO-d$_6$) δ=8.52 (d, J=5.6 Hz, 2 H), 8.39 (d, J=4.2 Hz, 1 H), 7.55 (d, J=4.2 Hz, 1 H), 7.37 (t, J=8.1 Hz, 1 H), 7.19-7.22 (m, 2 H), 7.05-7.09 (m, 2 H), 7.03 (ddd, J=8.2, 2.6, 1.0 Hz, 1 H); 3.74 (s, 3 H).

HRMS (ESI) calcd for C17H14N3OS [M+H]$^+$ 308.0852, found 308.0851.

Method I

3-(7-pyridin-4-yl-pyrazolo[5,1-b]thiazol-6-yl)-phenol 6-(3-Methoxy-phenyl)-7-pyridin-4-yl-pyrazolo[5,1-b]thiazole (65 mg, 0.212 mmol) was dissolved in dry DCM (2 mL) and cooled to 0° C. A 1 M solution of boron tribromide in DCM (0.850 mL, 0.848 mmol, 4 eq) was added dropwise and the mixture was allowed to warm to room temperature and stirred for 1 hours. Ice was then added to the reaction mixture, followed by saturated aqueous NaHCO$_3$ until pH 6. The aqueous phase was extracted with DCM and the organic layer was dried and evaporated to dryness. An insoluble solid formed during extraction and it was filtered and combined with the organic layer. The crude product was taken up with toluene and concentrated to dryness three times and the same treatment was repeated with DCM. 50 mg of 3-(7-pyridin-4-yl-pyrazolo[5,1-b]thiazol-6-yl)-phenol (80%) were obtained as pale yellow solid.

HPLC (254 nm): R$_t$: 5.02 min.

$^1$H NMR (401 MHz, DMSO-d$_6$) δ=9.57 (s, 1 H), 8.51 (d, J=5.9 Hz, 2 H), 8.37 (d, J=4.0 Hz, 1 H), 7.54 (d, J=4.1 Hz, 1 H), 7.25 (t, J=7.9 Hz, 1 H), 7.18-7.22 (m, 2 H), 6.88-6.95 (m, 2 H), 6.84 (ddd, J=1.0, 2.4, 8.1 Hz, 1 H).

HRMS (ESI) calcd for C16H12N3OS [M+H]$^+$ 294.0696, found 294.0690.

Example 19

Preparation of 2,4,6-tribromo-3-(7-pyridin-4-yl-pyrazolo[5,1-b]thiazol-6-yl)-phenol [(I)P, X=CH, R', R3=H, R3, R4, R5=Br, W=CHCH]

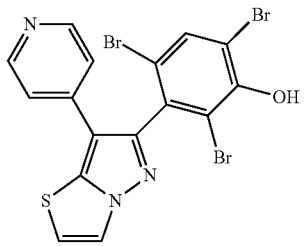 [SMILES: Oc1c(Br)cc(Br)c(-c2nn3ccsc3c2-c2ccncc2)c1Br]

3-(7-Pyridin-4-yl-pyrazolo[5,1-b]thiazol-6-yl)-phenol prepared as described in Example 18 (50 mg, 0.171 mmol) was suspended in dry DCM (1 mL) under nitrogen atmosphere and diisopropylamine (0.007 mL, 0.050 mmol, 0.3 eq) was added. A solution of N-bromosuccinimide (61 mg, 0.342 mmol, 2 eq) in DCM (2 mL) was then slowly added in about 30 minutes and stirring was continued for 2 hours. DMF was then added (2 mL) to afford complete dissolution, followed by a second aliquot of NBS (25 mg, 0.171 mmol, 1 eq) and stirring was continued for 2 more hours. The mixture was then diluted with ethyl acetate and washed with brine, dried over $Na_2SO_4$ and concentrated to dryness. The crude product was purified by chromatography on silica gel (DCM/MeOH 96:4) and then treated with ethyl ether to give 52 mg (67%) of 2,4,6-tribromo-3-(7-pyridin-4-yl-pyrazolo[5,1-b]thiazol-6-yl)-phenol as yellow solid.

HPLC (254 nm): $R_t$: 5.53 min.

$^1$H NMR (401 MHz, DMSO-$d_6$) δ=10.5 (br. s., 1 H), 8.51 (d, J=5.9 Hz, 2 H), 8.48 (d, J=4.2 Hz, 1 H), 8.06 (s, 1 H), 7.67 (d, J=4.1 Hz, 1 H), 6.91-7.09 (m, 2 H).

HRMS (ESI) calcd for C16H9Br3N3OS [M+H]$^+$ 527.8011, found 527,7997.

Example 20

Preparation of N-[2,4-difluoro-3-(7-pyridin-4-yl-2,3-dihydro-pyrazolo[5,1-b]thiazol-6-yl)-phenyl]-2,5-difluoro-benzenesulfonamide [(I)A, X=CH, R', R3, R4=H, R2, R5,=F, W=CH$_2$CH$_2$, R'6=2,5-difluoro-phenyl] (Cpd. no 23)

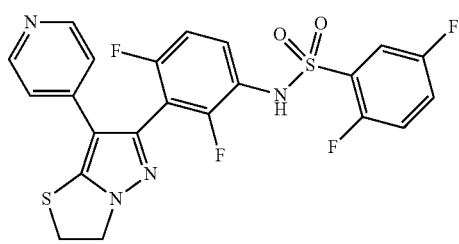 [SMILES: O=S(=O)(Nc1ccc(F)c(-c2nn3c(c2-c2ccncc2)SCC3)c1F)c1cc(F)ccc1F]

3-Dibenzylamino-2,6-difluoro-benzoic acid benzyl ester (8)

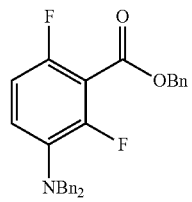

To 2,4-difluoro-phenylamine (a, 2.0 g, 15.5 mmol) in N,N-dimethylformamide (20 mL) potassium carbonate (6.0 g, 45 mmol) and benzyl bromide (5.49 mL, 35 mmol) were added. The reaction was stirred at room temperature overnight. The reaction was poured into water and extracted with ethyl acetate. The organic layer was washed with brine, dried over anhydrous sodium sulfate and filtered. The filtrate was concentrated under reduced pressure and purified by silica gel column chromatography eluting with hexane to give dibenzyl-(2,4-difluoro-phenyl)-amine as colourless oil (4.34 g, 90%).

To dibenzyl-(2,4-difluoro-phenyl)-amine (3.097 g, 10.02 mmol) in tetrahydrofuran (45 mL), under nitrogen atmosphere, cooled at −78° C. acetone/dry in ice bath, n-butyl-lithium (1.6 M in hexane, 6.88 mL, 11.02 mmol) was added slowly. The reaction was stirred for 1 hour, benzyl chloroformate (1.54 mL, 11.02 mmol) was added and the reaction was allowed to warm to room temperature during 2 hours. The reaction was poured into water and extracted with ethyl acetate. The organic layer was washed with brine, dried over anhydrous sodium sulfate and filtered. The filtrate was concentrated and purified by silica gel column chromatography eluting with 5% ethyl acetate in hexane grading to 10% acetate to provide the title compound as colourless oil (4.0 g, 90%).

HPLC (254 nm): $R_t$: 8.67 min.

1H NMR (401 MHz ,DMSO-d6) δ=7.20-7.46 (m, 15 H), 7.15 (m, 1 H), 6.98 (td, J=1.5, 9.2 Hz, 1 H), 5.39 (s, 2 H), 4.27 (s, 4 H).

HRMS (ESI) calcd for C28H23F2NO2 [M+H]+ 444.1770, found 444.1771.

Method A
Step e

1-(3-dibenzylamino-2,6-difluoro-phenyl)-2-pyridin-4-yl-ethanone

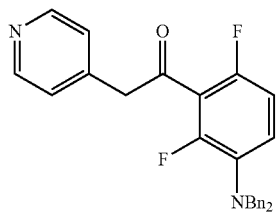

To 4-methyl-pyridine (806 μL, 8.33 mmol) in anhydrous tetrahydrofuran (35 mL) was added at 0° C. sodium hexamethyldisilazide 1 M in tetrahydrofuran (16.66 mL, 16.66 mmol) and the reaction was stirred for 20 minutes. 3-Dibenzylamino-2,6-difluoro-benzoic acid benzyl ester (3.691 g, 8.33 mmol) was dissolved in tetrahydrofuran (5 mL) and added dropwise to the solution with 4-methyl-pyridine, the reaction was stirred at 0° C. for one hour. The reaction was poured into saturated ammonium chloride solution and extracted with ethyl acetate. The organic layer was washed with brine, dried over anhydrous sodium sulfate, filtrate and concentrated under reduced pressure. The crude was purified by silica gel column chromatography eluting with ethyl acetate 30% in hexane to give the title compound (1.775 g, 50%).

MS (ESI): 429 [M+H]+.
Method A
Step f 1-(3-dibenzylamino-2,6-difluoro-phenyl)-2-[1,3]dithietan-2-ylidene-2-pyridin-4-yl-ethanone

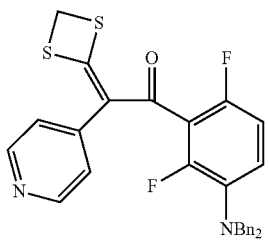

To a solution of 1-(3-Dibenzylamino-2,6-difluoro-phenyl)-2-pyridin-4-yl-ethanone (2.14 g, 4.994 mmol) in dry DMSO (22 mL) under nitrogen atmosphere solid potassium carbonate (2.07 g, 15 mmol, 3 eq) was added at room temperature, followed by carbon disulfide (0.9 mL, 15 mmol, 3 eq) and dibromomethane (1.05 mL, 15 mmol, 3 eq). The reaction mixture was stirred at room temperature for 3 hour and then poured into stirred iced water (150 mL). The aqueous phase was extracted with ethyl acetate (3 x 70 mL) and the combined organic layers were washed with water, dried and concentrated under reduced pressure. The crude product was purified by silica gel chromatography (n-hexane/ethyl acetate 7:3 to 6:4) to obtain 1.26 g of 1-(3-dibenzylamino-2,6-difluoro-phenyl)-2-[1,3]dithietan-2-ylidene-2-pyridin-4-yl-ethanone as yellow solid (49%).

MS (ESI): 517 [M+H]+.
Method A
Step g 5-(3-dibenzylamino-2,6-difluoro-phenyl)-4-pyridin-4-yl-2H-pyrazole-3-thiol

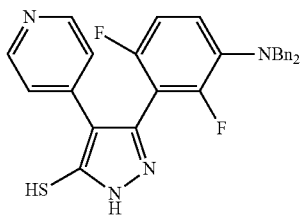

1-(3-Dibenzylamino-2,6-difluoro-phenyl)-2-[1,3]dithietan-2-ylidene-2-pyridin-4-yl-ethanone (1.26 g, 2.44 mmol) was suspended in absolute ethanol (10 mL). Hydrazine monohydrate (0.473 mL, 9.755 mmol, 4 eq) was added dropwise and the mixture was stirred at 60° C. for 2 hours. The suspension was concentrated under reduced pressure, taken up with toluene (2×20 mL) and evaporated to dryness. The crude product (1.35 g) was used in the following step without further purification.

MS (ESI): 485 [M+H]+.
Method B
Step a dibenzyl-[2,4-difluoro-3-(7-pyridin-4-yl-2,3-dihydro-pyrazolo[5,1-b]thiazol-6-yl)-phenyl]-amine

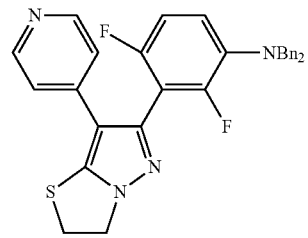

5-(3-Dibenzylamino-2,6-difluoro-phenyl)-4-pyridin-4-yl-2H-pyrazole-3-thiol (1.26 g, 2.6 mmol) was dissolved in dry DMF (33 mL) under nitrogen atmosphere. Solid potassium carbonate (1.8 g, 13 mmol, 5 eq) was added followed by 1,2-dibromoethane (0.252 mL, 2.86 mmol, 1.1 eq) and the suspension was stirred at room temperature for 4 hours. DMF was then removed under reduced pressure and the residue was partitioned between saturated aqueous NaHCO3 and ethyl acetate. The organic phase was washed with brine, dried over Na2SO4 and evaporated to dryness. 537 mg of dibenzyl-[2,4-difluoro-3-(7-pyridin-4-yl-2,3-dihydro-pyrazolo[5,1-b]thiazol-6-yl)-phenyl]-amine were obtained as white solid (47% over 2 steps).

MS (ESI): 511 [M+H]+.
Method E
Step b 2,4-difluoro-3-(7-pyridin-4-yl-2,3-dihydro-pyrazolo[5,1-b]thiazol-6-yl)-phenylamine

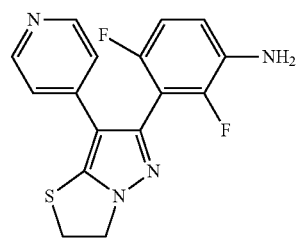 [SMILES: Nc1ccc(F)c(-c2nn3c(c2-c2ccncc2)SCC3)c1F]

To dibenzyl-[2,4-difluoro-3-(7-pyridin-4-yl-2,3-dihydro-pyrazolo[5,1-b]thiazol-6-yl)-phenyl]-amine (180 mg, 0.34 mmol) in toluene (2 mL) was added trifluoro-methanesulfonic acid (3.5 mL) in a sealable vial under nitrogen atmosphere. The mixture was stirred under microwave irradiation at 120° C. for ten minutes. The crude was diluted with ethyl acetate and washed with NaHCO3 saturated solution twice. The organic layer was dried over anhydrous sodium sulfate, filtered and the solvent was removed under reduced pressure. The product was isolated by column chromatography eluting with ethyl acetate: hexane (1: 1) (115 mg).

MS (ESI): 331 [M+H]+.

Method E
Step c

N-[2,4-difluoro-3-(7-pyridin-4-yl-2,3-dihydro-pyrazolo[5,1-b]thiazol-6-yl)-phenyl]-2,5-difluoro-benzenesulfonamide To 2,4-difluoro-3-(7-pyridin-4-yl-2,3-dihydro-pyrazolo[5,1-b]thiazol-6-yl)phenylamine (115 mg, 0.54 mmol) in pyridine (3 mL) was added 2,5-difluoro-benzenesulfonyl chloride (88 μL, 0.81 mmol) and the mixture was stirred under nitrogen atmosphere for one hour. The mixture was diluted with ethyl acetate and washed with NaHCO$_3$ saturated solution and with brine. The organic layer was dried over anhydrous sodium sulfate, filtered and dried. The solvent was removed under reduce pressure to give a mixture of mono and bis-sulfonamide. The crude was dissolved in THF (4 mL). A 1 M KOH solution (4 mL) was added and the mixture was stirred at 70° C. overnight. The solvent was removed under reduced pressure and the crude was dissolved in ethyl acetate and washed with NaHCO$_3$ saturated solution twice. The organic layer was dried over sodium sulphate, filtered and the solvent was removed under reduced pressure. N-[2,4-Difluoro-3-(7-pyridin-4-yl-2,3-dihydro-pyrazolo[5,1-b]thiazol-6-yl)-phenyl]-2,5-difluoro-benzenesulfonamide (64 mg, 37%) was isolated by silica gel chromatography column eluting with ethyl acetate 5% in hexane.

HPLC (254 nm): R$_t$: 5.58 min.

$^1$H NMR (401 MHz, DMSO-d$_6$) δ=10.71 (br. s., 1 H), 8.40-8.43 (m, 2 H), 7.51-7.60 (m, 1 H), 7.41-7.50 (m, 3 H), 7.22 (td, J=1.4, 8.8 Hz, 1 H), 6.78-6.83 (m, 2 H), 4.48 (t, J=7.6 Hz, 2 H), 4.04 (t, J=7.6 Hz, 2 H).

HRMS (ESI) calcd for C22H15F4N4O2S2 [M+H]$^+$ 507.0567, found 507.0575.

The invention claimed is:
1. A compound of formula (I):

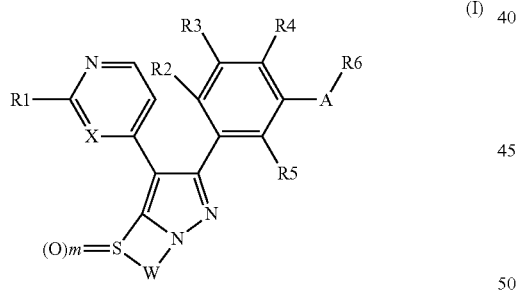

wherein:
X is CH or N;
R1 is hydrogen, halogen, NR7R8, NHCOR9, SR10 or SO$_2$R10, wherein:
  R7 and R8 are, each independently one from the other, hydrogen, or a group optionally substituted selected from straight or branched (C$_1$-C$_8$) alkyl, (C$_3$-C$_8$) cycloalkyl,
  heterocyclyl, aryl and heteroaryl, or R7 and R8 taken together may form a phthalyl group,
  R9 is OR10, NR11R12 or a group optionally substituted selected from straight or branched (C$_1$-C$_8$) alkyl, (C$_2$-C$_8$) alkenyl or (C$_2$-C$_8$) alkynyl, (C$_3$-C$_8$) cycloalkyl, heterocyclyl, aryl and heteroaryl,
  R10 is a group optionally substituted selected from straight or branched (C$_1$-C$_8$) alkyl, (C$_3$-C$_8$) cycloalkyl, heterocyclyl, aryl and heteroaryl, R11 and R12 are, each independently one from the other, hydrogen or a group optionally substituted selected from straight or branched (C$_1$-C$_8$) alkyl, (C$_3$-C$_8$) cycloalkyl, heterocyclyl, aryl and heteroaryl, or taken together with the nitrogen atom to which they are bonded R11 and R12 may form an optionally substituted 3 to 8 membered heterocyclyl or heteroaryl, optionally containing one additional heteroatom or heteroatomic group selected from S, O, N or NH;
R2, R3, R4 and R5 are, each independently one from the other, hydrogen, halogen, trifluoromethyl, trichloromethyl, cyano, OR13 or a group optionally substituted selected from straight or branched (C$_1$-C$_8$) alkyl, and (C$_3$-C$_8$) cycloalkyl, wherein:
R13 is hydrogen or a group optionally substituted selected from straight or branched (C$_1$-C$_8$) alkyl and (C$_3$-C$_8$) cycloalkyl;
A is —O—, —CON(Y)—, —CON(Y)O—, —CON(Y)N(Y)—, —CON(Y)SO$_2$—, —SO$_2$N(Y)—, —SO$_2$N(Y)O—, —SO$_2$N(Y)N(Y)—, —SO$_2$N(Y)CO—, —SO$_2$N(Y)CON(Y)—, —SO$_2$N(Y)SO$_2$—, —N(Y)CO—, —N(Y)SO$_2$—, —N(Y)CON(Y)—, —N(Y)CSN(Y)—, —N(Y)CON(Y)N(Y)—, —N(Y)COO—, —N(Y)CON(Y)SO$_2$—, —N(Y)SO$_2$N(Y)—, —C(R'R")CON(Y)—, —C(R'R")CSN(Y)—, —C(R'R")CON(Y)O—, —C(R' R")CON(Y)N(Y)—, —C(R'R")CON(Y)SO$_2$—, —C(R'R")SO$_2$N(Y)—, —C(R'R")SO$_2$N(Y)O—, —C(R'R")SO$_2$N(Y)N(Y)—, —C(R'R")SO$_2$N(Y)CO—, —C(R'R")SO$_2$N(Y)SO$_2$—, —C(R'R")N(Y)CO, —C(R'R")N(Y)SO$_2$—, —C(R'R")N(Y)CON(Y)—, —C(R'R")N(Y)CSN(Y)—, C(R'R")N(Y)COO— or —C(R'R")N(Y)SO$_2$N(Y)—, wherein:
Y is hydrogen or an optionally substituted straight or branched (C$_1$-C$_3$) alkyl;
and R' and R" are, each independently one from the other, hydrogen or an optionally further substituted straight or branched (C$_1$-C$_6$) alkyl, or taken together with the carbon atom to which they are bonded R' and R" may form an optionally substituted (C$_3$-C$_8$) cycloalkyl;
R6 is hydrogen or an optionally substituted group selected from straight or branched (C$_1$-C$_8$) alkyl, (C$_2$-C$_8$) alkenyl, (C$_2$-C$_8$) alkynyl , (C$_3$-C$_8$) cycloalkyl, heterocyclyl, aryl and heteroaryl;
m is an integer from 0 to 2;
W is (CH$_2$)n, wherein n is an integer from 2 to 4, CH(R14)-CH(R15) or C(R14)=C(R15), wherein
R14 and R15 are, each independently one from the other, hydrogen or a group optionally substituted selected from straight or branched (C$_1$-C$_8$) alkyl, (C$_3$-C$_8$) cycloalkyl, heterocyclyl, aryl and heteroaryl, or R14 is hydrogen and R15 is COR16, or R15 is hydrogen and R14 is COR16, wherein:
R16 is OR17, NR18R19 or a group optionally substituted selected from straight or branched (C$_1$-C$_8$) alkyl, (C$_2$-C$_8$) alkenyl or (C$_2$-C$_8$) alkynyl, (C$_3$-C$_8$) cycloalkyl, heterocyclyl, aryl and heteroaryl, wherein:
R17 is hydrogen or a group optionally substituted selected from straight or branched (C$_1$-C$_8$) alkyl, (C$_3$-C$_8$) cycloalkyl, heterocyclyl, aryl and heteroaryl;
R18 and R19 are, each independently one from the other, a hydrogen, a group optionally substituted selected from straight or branched (C$_1$-C$_8$) alkyl, (C$_3$-C$_8$) cycloalkyl, heterocyclyl, aryl and heteroaryl, or taken together with the nitrogen atom to which they are bonded R18 and R19 may form an optionally substituted 3 to 8 membered heterocyclyl or heteroaryl, optionally containing one additional heteroatom or heteroatomic group selected from S, O, N or NH; and pharmaceutically acceptable salts thereof.

2. The compound according to claim 1 wherein:
A is —O—, —CON(Y)—, —CON(Y)O—, —CON(Y)N(Y)—, —CON(Y)SO$_2$—, —SO$_2$N(Y)—, —N(Y)CO—, —N(Y)SO$_2$—, —N(Y)CON(Y)—, —N(Y)CSN(Y)—, —N(Y)COO—, —C(R'R")CON(Y)—, —C(R'R")N(Y)CO or —C(R'R")N(Y)CON(Y)—,
wherein:
Y, R' and R" are as defined in claim 1.

3. The compound according to claim 1 wherein:
A is —O—, —CON(Y)—, —CON(Y)SO$_2$—, —SO$_2$N(Y)—, —N(Y)CO—, —N(Y)SO$_2$—, —N(Y)CON(Y)—, —N(Y)CSN(Y)—,
wherein:
Y, R' and R" are as defined in claim 1.

4. The compound according to claim 1, wherein:
R1 is hydrogen or NR7R8, wherein:
R7 and R8 are, each independently one from the other, hydrogen or a group optionally substituted selected from straight or branched (C$_1$-C$_8$) alkyl, (C$_3$-C$_8$) cycloalkyl, heterocyclyl, aryl and heteroaryl.

5. The compound according to claim 1 wherein:
R2, R3, R4 and R5 are, each independently one from the other, hydrogen, halogen, trifluoromethyl, trichloromethyl or cyano.

6. The compound according to claim 1 wherein:
R6 is an optionally substituted group selected from straight or branched (C$_1$-C$_8$) alkyl, (C$_3$-C$_8$) cylcoalkyl, heterocyclyl, aryl and heteroaryl.

7. The compound according to claim 1 or a pharmaceutically acceptable salt thereof selected from the group consisting of:
1-(4-chloro-phenyl)-3-[3-(3-pyridin-4-yl-6,7-dihydro-5H-pyrazolo[5,1-b][1,3]thiazin-2-yl)-phenyl]-urea,
1-[3-(3-pyridin-4-yl-6,7-dihydro-5H-pyrazolo[5,1-b][1,3]thiazin-2-yl)-phenyl]-3-p-tolyl-urea,
1-[3-(3-pyridin-4-yl-6,7-dihydro-5H-pyrazolo[5,1-b][1,3]thiazin-2-yl)-phenyl]-3-(4-trifluoromethyl-phenyl)-urea,
3-fluoro-N-[3-(3-pyridin-4-yl-6,7-dihydro-5H-pyrazolo[5,1-b][1,3]thiazin-2-yl)-phenyl]-benzenesulfonamide,
1-[3-(7-pyridin-4-yl-2,3-dihydro-pyrazolo[5,1-b]thiazol-6-yl)-phenyl]-3-(4-trifluoromethyl-phenyl)-urea,
1-(4-chloro-phenyl)-3-[3-(7-pyridin-4-yl-2,3-dihydro-pyrazolo[5,1-b]thiazol-6-yl)-phenyl]-urea,
3-(7-pyridin-4-yl-2,3-dihydro-pyrazolo[5,1-b]thiazol-6-yl)-phenol,
3-(3-pyridin-4-yl-6,7-dihydro-5H-pyrazolo[5,1-b][1,3]thiazin-2-yl)-phenol
2,5-difluoro-N-[3-(3-pyridin-4-yl-6,7-dihydro-5H-pyrazolo[5,1-b][1,3]thiazin-2-yl)-phenyl]-benzenesulfonamide,
3-(1,1-dioxo-7-pyridin-4-yl-2,3-dihydro-pyrazolo[5,1-b]thiazol-6-yl)-phenol,
2,5-difluoro-N-[3-(7-pyridin-4-yl-2,3-dihydro-pyrazolo[5,1-b]thiazol-6-yl)-phenyl]-benzenesulfonamide,
N-[3-(3-pyridin-4-yl-6,7-dihydro-5H-pyrazolo[5,1-b][1,3]thiazin-2-yl)-phenyl]-2-(4-trifluoromethyl-phenyl)-acetamide,
furan-2-sulfonic acid [3-(3-pyridin-4-yl-6,7-dihydro-5H-pyrazolo[5,1-b][1,3]thiazin-2-yl)-phenyl]-amide,
thiophene-3-sulfonic acid [3-(3-pyridin-4-yl-6,7-dihydro-5H-pyrazolo[5,1-b][1,3]thiazin-2-yl)-phenyl]-amide,
N-(4-tert-butyl-phenyl)-3-(7-pyridin-4-yl-2,3-dihydro-pyrazolo[5,1-b]thiazol-6-yl)-benzamide,
7-pyridin-4-yl-6-{3-[3-(4-trifluoromethyl-phenyl)-ureido]-phenyl}-pyrazolo[5,1-b]thiazole-3-carboxylic acid amide,
6-[3-(2,5-difluoro-benzenesulfonylamino)-phenyl]-7-pyridin-4-yl-pyrazolo[5,1-b]thiazole-3-carboxylic acid amide,
1-(4-tert-butyl-phenyl)-3-[3-(7-pyridin-4-yl-2,3-dihydro-pyrazolo[5,1-b]thiazol-6-yl)-phenyl]-urea,
1-[3-(1-oxo-7-pyridin-4-yl-2,3-dihydro-pyrazolo[5,1-b]thiazol-6-yl)-phenyl]-3-(4-trifluoromethyl-phenyl)-urea,
3-(7-pyridin-4-yl-pyrazolo[5,1-b]thiazol-6-yl)-phenol,
2,5-difluoro-N-[3-(7-pyridin-4-yl-pyrazolo[5,1-b]thiazol-6-yl)-phenyl]-benzenesulfonamide,
1-[3-(7-pyridin-4-yl-pyrazolo[5,1-b]thiazol-6-yl)-phenyl]-3-(4-trifluoromethyl-phenyl)-urea,
N-[2,4-difluoro-3-(7-pyridin-4-yl-2,3-dihydro-pyrazolo[5,1-b]thiazol-6-yl)-phenyl]-2,5-difluoro-benzenesulfonamide,
3-(7-pyridin-4-yl-2,3-dihydro-pyrazolo[5,1-b]thiazol-6-yl)-N-(4-trifluoro-methyl-phenyl)-benzamide,
2,6-dibromo-3-(7-pyridin-4-yl-2,3-dihydro-pyrazolo[5,1-b]thiazol-6-yl)-phenol,
N-{4-[6-(3-Hydroxy-phenyl)-pyrazolo[5,1-b]thiazol-7-yl]-pyridin-2-yl}-acetamide,
3-[7-(2-amino-pyrimidin-4-yl)-pyrazolo[5,1-b]thiazol-6-yl]-phenol,
N-[2,4-difluoro-3-(7-pyridin-4-yl-pyrazolo[5,1-b]thiazol-6-yl)-phenyl]-2,5-difluoro-benzenesulfonamide,
N-(4-{6-[3-(2,5-difluoro-benzenesulfonylamino)-phenyl]-2,3-dihydro-pyrazolo[5,1-b]thiazol-7-yl}-pyridin-2-yl)-acetamide,
N-[4-(6-{3-[3-(4-trifluoromethyl-phenyl)-ureido]-phenyl}-2,3-dihydro-pyrazolo[5,1-b]thiazol-7-yl)-pyridin-2-yl]-acetamide,
1-[3-(7-pyrimidin-4-yl-2,3-dihydro-pyrazolo[5,1-b]thiazol-6-yl)-phenyl]-3-(4-trifluoromethyl-phenyl)-urea,
1-{3-[7-(2-amino-pyrimidin-4-yl)-2,3-dihydro-pyrazolo[5,1-b]thiazol-6-yl]-phenyl}-3-(4-trifluoromethyl-phenyl)-urea,
N-(4-{6-[3-(2,5-difluoro-benzenesulfonylamino)-phenyl]-pyrazolo[5,1b]-thiazol-7-yl}-pyridin-2-yl)-acetamide,
N-[4-(6-{3-[3-(4-trifluoromethyl-phenyl)-ureido]-phenyl}-pyrazolo[5,1-b]-thiazol-7-yl)-pyridin-2-yl]-acetamide,
1-[3-(7-pyrimidin-4-yl-pyrazolo[5,1-b]thiazol-6-yl)-phenyl]-3-(4-trifluoro-methyl-phenyl)-urea,
1-{3-[7-(2-amino-pyrimidin-4-yl)-pyrazolo[5,1-b]thiazol-6-yl]-phenyl}-3-(4-trifluoromethyl-phenyl)-urea,
N-(4-{6-[3-(2,5-difluoro-benzenesulfonylamino)-2,6-difluoro-phenyl]-2,3-dihydro-pyrazolo[5,1-b]thiazol-7-yl}-pyridin-2-yl)-acetamide,
N-(4-{6-[3-(2,5-difluoro-benzenesulfonylamino)-2,6-difluoro-phenyl]-pyrazolo[5,1-b]thiazol-7-yl}-pyridin-2-yl)-acetamide,
N-[2,4-difluoro-3-(7-pyrimidin-4-yl-pyrazolo[5,1-b]thiazol-6-yl)-phenyl]-2,5-difluoro-benzenesulfonamide,
N-{3-[7-(2-amino-pyrimidin-4-yl)-pyrazolo[5,1-b]thiazol-6-yl]-2,4-difluoro-phenyl}-2,5-difluoro-benzenesulfonamide,
3-(7-pyridin-4-yl-pyrazolo[5,1-b]thiazol-6-yl)-N-(4-trifluoromethyl-phenyl)-benzamide, 3-(7-pyrimidin-4-yl-pyrazolo[5,1-b]thiazol-6-yl)-N-(4-trifluoromethyl-phenyl)-benzamide, 3-[7-(2-amino-pyrimidin-4-yl)-pyrazolo[5,1-b]thiazol-6-yl]-N-(4-trifluoro-methyl-phenyl)-benzamide and 3-(7-pyrimidin-4-yl-pyrazolo[5,1-b]thiazol-6-yl)-phenol.

8. A process for preparing a compound of formula (I)A:

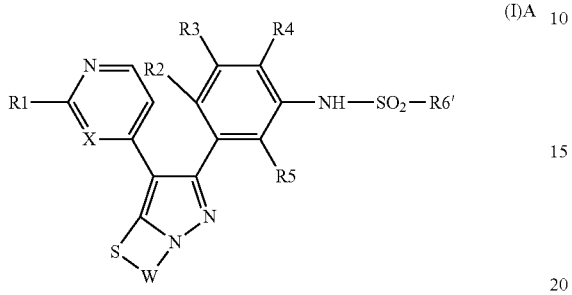

(I)A wherein

R6' is as R6 defined in claim 1 but not hydrogen, and

W, X, R1, R2, R3, R4 and R5 are as defined in claim 1, characterized in that the process comprises the following steps:

a) either reducing a compound of formula (II)1:

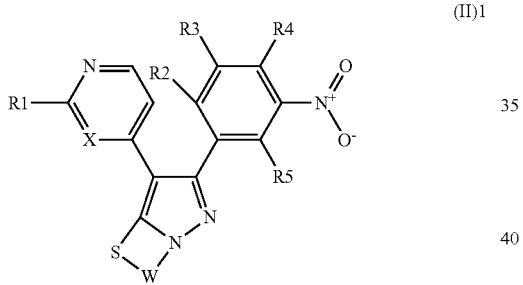

(II)1 wherein W, X, R1, R2, R3, R4 and R5 are as defined above; or b) removing the protecting group from the amino moiety of a compound of formula (II)2:

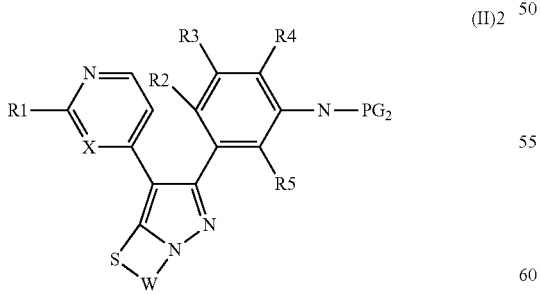

(II)2 wherein PG$_2$ is a suitable protecting group of the amino moiety, such as benzyl, bis-benzyl, p-methoxybenzyl, trityl, phtaloyl, benzyloxycarbonyl, p-nitrobenzyloxycarbonyl, and the like and W, X, R1, R2, R3, R4 and R5 are as defined above;

c) coupling the resultant compound of formula 18:

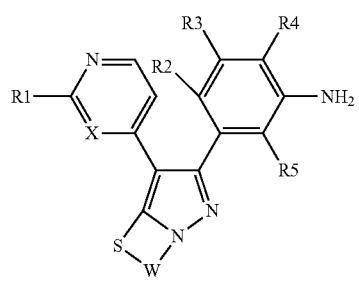

18 wherein W, X, R1, R2, R3, R4 and R5 are as defined above, with a compound of formula R6'SO$_2$Cl, wherein R6' is as defined above, to give a compound of formula (I)A as defined above, optionally separating the resultant compound of formula (I)A into the single isomers, and/or converting it into another derivative of formula (I)A and or into a pharmaceutically acceptable salt.

9. A process for preparing a compound of formula (I)C:

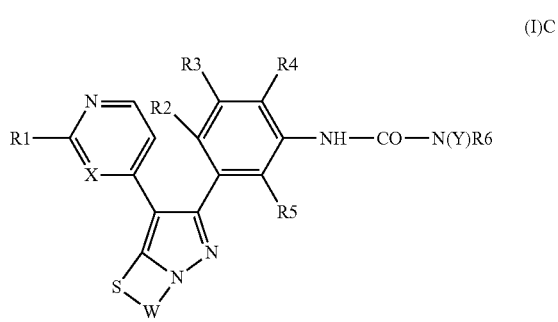

(I)C wherein R6 is as defined in claim 1 except for hydrogen; W, X, R1, R2, R3, R4, and R5 are as defined in claim 1, and Y is hydrogen, characterized in that the process comprises the following steps:

e) coupling the compound of formula 18, as defined in claim 8, with a compound of formula R6'NCO, wherein R6' is as defined in claim 8, to give a compound of formula (I)C as defined above, optionally separating the resultant compound of formula (1)C into the single isomers, and/or converting it into another derivative of formula (I)C and or into a pharmaceutically acceptable salt.

10. A process for preparing a compound of formula (I)I:

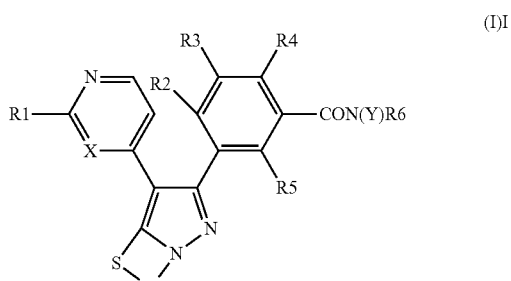

(I)I wherein W, X, R1, R2, R3, R4, R5 and R6 are as defined in claim 1, characterized in that the process comprises the following steps:

a) hydrolyzing a compound of formula (II)4:

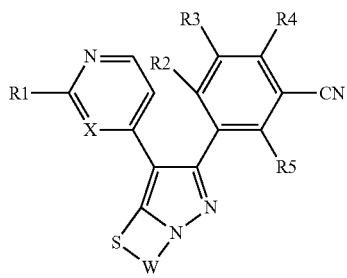

(II)4 wherein W, X, R1, R2, R3, R4 and R5 are as defined above;

b) condensing the resultant compound of formula 27:

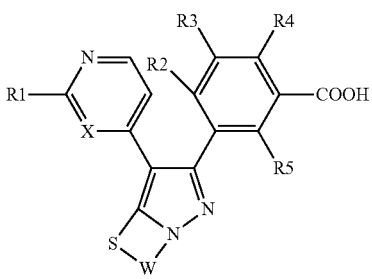

27 wherein W, X, R1, R2, R3, R4 and R5 are as defined above, with a primary or secondary amine of formula R6-N(Y)H, wherein R6 and Y are as defined in claim 1, to give a compound of formula (I)I as defined above, optionally separating the resultant compound of formula (I)I into the single isomers, and/or converting it into another derivative of formula WI and or into a pharmaceutically acceptable salt.

11. A process for preparing a compound of formula (I)P:

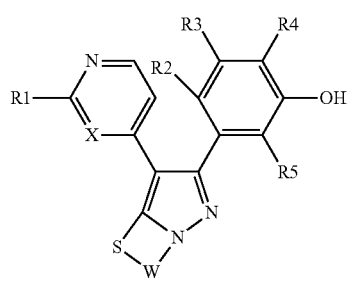

(I)P wherein W, X, R1, R2, R3, R4 and R5 are as defined in claim 1, characterized in that the process comprises the following step:

a) deprotecting the hydroxyl group of a compound of formula (I)P':

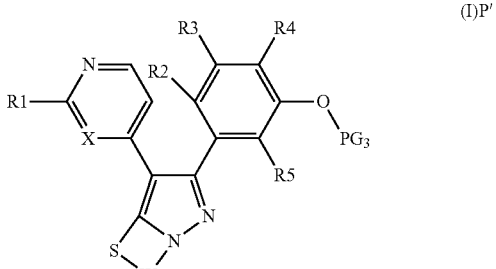

(I)P' wherein X, X, R1, R2, R3, R4 and R5 are as defined above and $PG_3$ is a suitable protecting group of the hydroxyl moiety, such as methyl benzyl, p-methoxybenzyl, trityl and the like, to give a compound of formula (I)P as defined above, optionally separating the resultant compound of formula (I)P into the single isomers, and/or converting it into another derivative of formula (I)P and or into a pharmaceutically acceptable salt.

12. A method for treating a disease selected from the group consisting of melanoma, ovarian cancer and breast cancer which comprises administering to a mammal in need thereof an effective amount of a compound of formula (I) as defined in claim 1.

13. An in vitro method for inhibiting the RAF family activity which comprises contacting the said receptor with an effective amount of a compound as defined in claim 1.

14. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

15. A product or kit comprising a compound of formula (I) or a pharmaceutically acceptable salt thereof, as defined in claim 1, or pharmaceutical compositions thereof as defined in claim 14 and one or more chemotherapeutic agents, as a combined preparation for simultaneous, separate or sequential use in anticancer therapy.

* * * * *